(12) United States Patent
Ekegren et al.

(10) Patent No.: US 7,807,677 B2
(45) Date of Patent: Oct. 5, 2010

(54) HIV PROTEASE INHIBITORS

(75) Inventors: Jenny Ekegren, Huddinge (SE); Anders Hallberg, Huddinge (SE); Hans Wallberg, Huddinge (SE); Bertil Samuelsson, Huddinge (SE); Mahalingam Kannan, Huddinge (SE)

(73) Assignee: Medivir AB, Huddinge (SE)

( * ) Notice: Subject to any disclaimer, the term of this patent is extended or adjusted under 35 U.S.C. 154(b) by 139 days.

(21) Appl. No.: 11/884,224

(22) PCT Filed: Feb. 9, 2006

(86) PCT No.: PCT/EP2006/001135
§ 371 (c)(1),
(2), (4) Date: Mar. 27, 2008

(87) PCT Pub. No.: WO2006/084688
PCT Pub. Date: Aug. 17, 2006

(65) Prior Publication Data
US 2008/0249102 A1 Oct. 9, 2008

(30) Foreign Application Priority Data

| Feb. 10, 2005 | (SE) | ................... 0500307 |
| Oct. 25, 2005 | (SE) | ................... 0502352 |
| Nov. 8, 2005 | (SE) | ................... 0502468 |

(51) Int. Cl.
C07C 271/22 (2006.01)
C07C 275/24 (2006.01)
C07C 311/06 (2006.01)
C07D 213/42 (2006.01)
C07D 241/12 (2006.01)
A61K 31/18 (2006.01)
A61K 31/17 (2006.01)
A61K 31/325 (2006.01)
A61K 31/38 (2006.01)

(52) U.S. Cl. ............... 514/252.1; 514/357; 514/464; 514/443; 514/476; 544/336; 546/332; 549/32; 549/441; 560/24; 560/27

(58) Field of Classification Search ............ None
See application file for complete search history.

(56) References Cited

U.S. PATENT DOCUMENTS 6,291,687 B1 * 9/2001 Classon et al. ............... 506/15
6,489,364 B2 * 12/2002 Classon et al. .............. 514/616

FOREIGN PATENT DOCUMENTS

| EP | 0480 714 A2 | 4/1992 |
| WO | WO 92/15319 | * 9/1992 |
| WO | WO 97/40029 | 10/1997 |
| WO | WO98/45330 | 10/1998 |
| WO | WO 2006/084688 | 8/2006 |

OTHER PUBLICATIONS

Jenny K. Ekegren et al., "A New Class of HIV-1 Protease Inhibitors Containing a Tertiary Alcohol in the Transition-State Mimicking Scaffold", *J. Med. Chem.*: 48, 8098-8102 (2005).
Johanna Wachtmeister et al., , *Tetrahedron* 56: 3219-3225 (2000).
Guido Bold et al. "New Aza-Dipeptide Analogues as Potent and Orally Absorbed HIV-1 Protease Inhibitors: Candidates for Clinical Development," *J.Med. Chem*: 41, 3387-3401 (1998).

* cited by examiner

*Primary Examiner*—Fiona T Powers
(74) *Attorney, Agent, or Firm*—Birch, Stewart, Kolasch & Birch, LLP

(57) ABSTRACT

Compounds of the formula I:

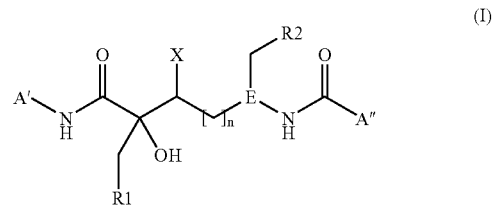

wherein
$R^1$, $R^2$, X and N are as defined in the specification;
E is N, CH;
A' and A" are terminal groups as defined in the specification.

The compounds have utility as HIV-1 protease inhibitors.

63 Claims, No Drawings

HIV PROTEASE INHIBITORS

This application is the National Phase Under 35 U.S.C. §371 of PCT International Application No. PCT/EP06/01135 which has an International filing date of Feb. 9, 2006, which designates the United States of America, and claims priority to Swedish Patent Application No. 0500307-4, which has a filing date of Feb. 10, 2005, Swedish Patent Application No. 0502352-8, which has a filing date of Oct. 25, 2005 and Swedish Patent Application No. 0502468-2, which has a filing date of Oct. 9, 2005, the entire contents of all applications listed above are hereby incorporated by reference.

BACKGROUND TO THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression, which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein, the polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

The genomes of retroviruses encode a protease that is responsible for the proteolytic processing of one or more polyprotein precursors such as the pol and gag gene products. Retroviral proteases most commonly process the gag precursor into the core proteins, and also process the pol precursor into reverse transcriptase and retroviral protease. The correct processing of the precursor polyproteins by the retroviral protease is necessary for the assembly of the infectious virions. It has been shown that in vitro mutagenesis that produces protease-defective virus leads to the production of immature core forms which lack infectivity. Therefore, retroviral protease inhibition provides an attractive target for antiviral therapy.

As evidenced by the protease inhibitors presently marketed and in clinical trials, a wide variety of compounds have been studied as potential HIV protease inhibitors. The first inhibitor of so-called retroviral aspartate protease to be approved for combating the infection was saquinavir. Since then others have followed including indinavir (Merck), ritonavir (Abbott), amprenavir and its prodrug amprenavir phosphate (Vertex/GSK), lopinavir (Abbott), nelfinavir (Aguoron/Pfizer), tipranavir (Pharmacia/Boehringer) and atazanavir (Novartis/BMS).

Each of these prior art compounds has liabilities in the therapeutic context resulting in sub-optimal treatment regimes, side effects such as lipodystrophy and poor patient compliance. In conjunction with the replicative infidelity of the HIV genetic machinery and the very high viral turnover in vivo, the sub-optimal performance and pharmacokinetics of prior art HIV protease inhibitors enable the rapid generation of drug escape mutants. This in turn dramatically limits the effective treatment length of current HIV drugs as HIV quickly becomes resistant and/or patients develop physical or psychological aversions to the drugs themselves or their side effects.

The aim of the present invention is to provide a novel type of compound that is equipped, especially, with a high degree of inhibitory activity against virus replication in cells, high antiviral activity against numerous virus strains, including those which are resistant to known compounds, such as saquinavir, ritonavir and indinavir, and especially advantageous pharmacological properties, for example good pharmacokinetics, such as high bioavailability and high blood levels, and/or high selectivity.

In accordance with the invention, there is provided a compound of the formula I:

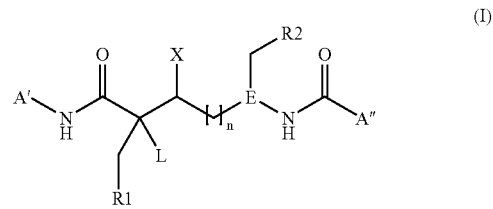

wherein
R$^1$ is —R$^{1'}$, —OR$^{1'}$, —SR$^{1'}$,
R$^{1'}$ is C$_1$-C$_6$Alk, C$_0$-C$_3$alkanediylcarbocyclyl or C$_{0-3}$alkanediylheterocyclyl, any of which is optionally substituted with up to 3 substituents independently selected from R$^{10}$;
R$^2$ is C$_1$-C$_6$Alk, C$_0$-C$_3$alkanediylcarbocyclyl, C$_0$-C$_3$alkanediylheterocyclyl, any of which is optionally substituted with up to 3 substituents independently selected from R$^{10}$;

X is H, F, OH, $C_1$-$C_3$Alk or $C_0$-$C_3$alkanediyl-O—$C_1$-$C_3$alkyl;

L is OH, F, $NH_2$, —$NHC_1$-$C_3$Alk; —$N(C_1$-$C_3Alk)_2$;

n is 0, 1 or 2;

E is N or CH;

A' is a bicyclic ring system comprising a first 5 or 6 membered saturated ring optionally containing an oxygen hetero atom and optionally substituted with hydroxy and/or methyl, having fused thereto a second 5 or 6 membered unsaturated ring optionally containing one or two hetero atoms selected from S, O and N, and optionally substituted with mono- or di-fluoro; or A' is a group of formula (II), (II'), (III) or (IV):

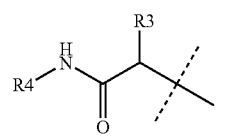
(II)

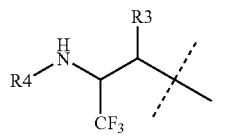
(II')

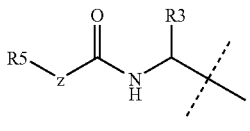
(III)

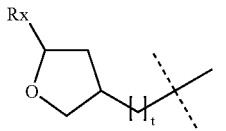
(IV)

wherein, $R^3$ is H; or $R^3$ is $C_1$-$C_6$Alk, $C_0$-$C_3$alkanediylcarbocyclyl, $C_0$-$C_3$alkanediylheterocyclyl, any of which is optionally substituted with up to three substituents independently selected from $R^{11}$;

$R^4$ is $C_1$-$C_6$Alk, $C_0$-$C_3$alkanediylcarbocyclyl, $C_0$-$C_3$alkanediylheterocyclyl, any of which is optionally substituted with up to three substituents independently selected from $R^{10}$;

$R^5$ is $C_1$-$C_6$Alk, $C_0$-$C_3$alkanediylcarbocyclyl, $C_0$-$C_3$alkanediylheterocyclyl, any of which is optionally substituted with up to three substituents independently selected from $R^{10}$;

Z is a bond, —NH— or —O—;

Rx is H, $C_1$-$C_3$alkyloxy, $C_1$-$C_3$ straight or branched alkyl optionally substituted with halo, hydroxy, $C_1$-$C_3$alkyloxy; or Rx, together with the adjacent carbon atom, defines a fused furanyl or pyranyl ring which is optionally substituted with halo or $C_1$-$C_3$Alk;

t is 0 or 1;

A" is a group of formula (V), (VI) (VII) or (VIII);

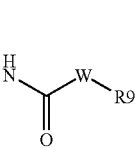
(V)

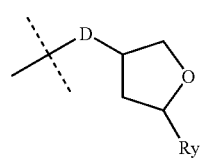
(VI)

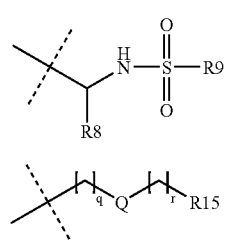
(VII)

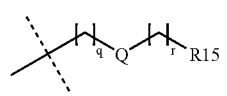
(VIII)

wherein;

$R^8$ is H; or $R^8$ is $C_1$-$C_6$Alk, $C_0$-$C_3$alkanediylcarbocyclyl, $C_0$-$C_3$alkanediylheterocyclyl, any which is optionally substituted with up to three substituents independently selected from $R^{11}$ $R^9$ is $C_1$-$C_6$Alk, $C_0$-$C_3$alkanediylcarbocyclyl, $C_0$-$C_3$alkanediylheterocyclyl, any of which is optionally substituted with up to three substituents independently selected from $R^{10}$;

W is a bond, —$NR^{13}$— or —O—;

$R^{13}$ is H, $C_1$-$C_6$Alk or $R^{13}$ and $R^9$ together with the N atom to which they are attached define a saturated, partially saturated or aromatic N-containing ring containing 5 or 6 ring atoms, which is optionally substituted with up to three substituents selected from $R^{10}$;

D is O or NH;

Ry is H or Ry, together with the adjacent C atom defines a fused furan or pyran ring;

Q is O, $CHR^8$ or a bond;

$R^{15}$ is carbocyclyl or heterocyclyl, any of which is optionally substituted with up to three substituents independently selected from $C_1$-$C_3$Alk, hydroxy, oxo, halo;

r and q are independently 0 or 1;

$R^{10}$ is halo, oxo, cyano, azido, nitro, $C_1$-$C_6$Alk, $C_0$-$C_3$alkanediylcarbocyclyl, $C_0$-$C_3$alkanediylheterocyclyl, Y—NRaRb, Y—O—Rb, Y—C(=O)Rb, Y—(C=O)NRaRb, Y—NRaC(=O)Rb, Y—$NHSO_p$Rb, Y—$S(=O)_p$Rb, Y—$S(=O)_p$NRaRb, Y—C(=O)ORb or Y—NRaC(=O)ORb; wherein;

Y is a bond or $C_1$-$C_3$alkanediyl;

Ra is H or $C_1$-$C_3$Alk;

Rb is H or $C_1$-$C_6$Alk, $C_0$-$C_3$alkanediylcarbocyclyl or $C_0$-$C_3$alkanediylheterocyclyl;

p is 1 or 2;

$R^{11}$ is halo, oxo, cyano, azido, nitro, $C_1$-$C_3$Alk, Y—NRaRa', Y—O—Ra; wherein;

Ra' is H or $C_1$-$C_3$Alk; or Ra and Ra' and the nitrogen atom to which they are attached define pyrrolidine, morpholine, piperidine or piperazine which is optionally 4-substituted with methyl or acetyl;

and pharmaceutically acceptable salts thereof.

A further aspect of the invention embraces a pharmaceutical composition comprising a compound as defined above and a pharmaceutically acceptable carrier or diluent therefore. A still further aspect of the invention envisages the use of a compound as defined above in the manufacture of a medicament for the prophylaxis or treatment of HIV infection. An additional aspect of the invention provides a method of medical treatment or prophylaxis for HIV infection comprising the administration of an effective amount of a compound as defined in above to an individual infected or threatened with HIV infection.

Without in any way wishing to be bound by theory, or the ascription of tentative binding modes for specific variables, the notional concepts P1, P1', P2 and P2' as used herein are provided for convenience only and have substantially their conventional meanings, as illustrated by Schechter & Berger, (1976) Biochem Biophys Res Comm 27 157-162, and denote those portions of the inhibitor believed to fill the S1, S1', S2 and S2' subsites respectively of the enzyme, where S1 is adjacent and S2 remote from the cleavage site on one side and S1' is adjacent and S2' remote from the cleavage site on the other side. Regardless of binding mode, the compounds defined by Formula I are intended to be within the scope of the invention. It is conceivable that $R^1$ and $R^2$ respectively fill the S1 and S1' subsites, whereas A' and A" interact with the S2 and S2', but also conceivable with the inverse arrangement.

Conveniently, the compounds of the invention display at least 75%, preferably at least 90%, such as in excess of 95%, enantiomeric purity around the carbon shared by the hydroxyl group and the $R^1$ methylene function depicted in formula I. It is currently preferred that the compounds exhibit a high degree of enantiomeric purity of the steroisomeres as shown in the partial structure:

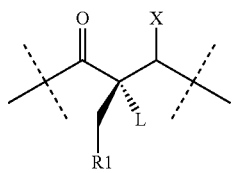

Group X can be either R or S stereochemistry.

As defined above X is H, OH, $C_1$-$C_3$Alk or $C_0$-$C_3$alkanediyl-O—$C_1$-$C_3$alkyl. Convenient values for X include OH and $C_0$-$C_3$alkanediyl-O—$C_1$-$C_3$alkyl especially methoxy (i.e. $C_0$) and hydroxymethyl. A currently favoured value for X is H or OH.

As recited above, L is OH, F, $NH_2$, $NHC_1$-$C_3$Alk, $N(C_1$-$C_3$Alk$)_2$, wherein the $NHC_1$-$C_3$Alk and $N(C_1$-$C_3$Alk$)_2$ preferably are NHMe and NHMe$_2$ respectively. A currently preferred value for L is fluoro and a more preferred value is OH.

The compounds of the invention can have 2 chain atoms between the carbonyl depicted in formula I and function E (i.e. n is 0). Other embodiments of the invention comprise 3 or 4 chain atoms between the carbonyl and function E, i.e. n is 1 or 2 respectively. In favoured embodiments of the invention the compounds have 3 chain atoms between the carbonyl and function E, i.e. n is 1.

Conveniently, the compounds of the invention comprise a hydrazide function, that is E is N, as it is believed that this configuration pitches the $R^2$-methylene side chain at an advantageous angle relative to the S1' (or S1) pocket of HIV protease, for example when A" is according to formula V. However the optimal angle will, of course depend on other interactions along the backbone, side chains and termini of the compounds and thus additional embodiments of the invention comprise CH at function E.

As defined above, $R^1$ is $R^{1'}$, $OR^{1'}$ or $SR^{1'}$ wherein $R^{1'}$ is $C_1$-$C_6$allyl, but is especially $C_0$-$C_3$alkanediylcarbocyclyl or $C_0$-$_3$alkanediylheterocyclyl. Typical examples of such species are recited below. Any of these species is optionally substituted with up to 3 substituents independently selected from $R^{10}$ as defined above. Convenient optional substituents to $R^{1'}$ include one or two substituents selected from halo, oxo, cyano, $C_1$-$C_6$Alk, $C_0$-$C_3$alkanediylcarbocyclyl, $C_0$-$C_3$alkanediylheterocyclyl, Y—NRaRb, Y—O—Rb; where Y is a bond or $C_1$-$C_3$Alk, Ra is H or $C_1$-$C_3$Alk and Rb is H or $C_1$-$C_3$Alk. Particularly preferred substituents include fluoro, $C_1$-$C_3$Alk, $C_0$-$C_1$alkanediylcarbocyclyl, $C_0$-$C_1$alkanediylheterocyclyl.

Conveniently, the $C_0$-$C_3$alkanediyl linker moiety of such $C_0$-$C_3$alkanediylcarbocyclyl or $C_0$-$_3$alkanediylheterocyclyl species as $R^1$ or the optional substituent thereto defines methylene or even more preferably a bond, i.e. $R^{1'}$ or the substituent is simply an optionally substituted carbocyclyl or heterocyclyl, such as optionally substituted phenyl or optionally substituted pyridyl, pyrazinyl, pyrimidinyl or pyridazinyl.

Preferably $R^1$ is $R^{1'}$ or $OR^{1'}$.

In one embodiment of the present invention the $R^{10}$ substituent of $R^1$ is Y—O—Rb where Y is a bond and Rb is an optionally substituted $C_0$-$C_3$alkanediylaryl or $C_0$-$C_3$alkanediylheteroaryl. The optional substituent is preferably $C_1$-$C_3$Alk, such as methyl Preferred structures for $R^1$ according to this embodiment include:

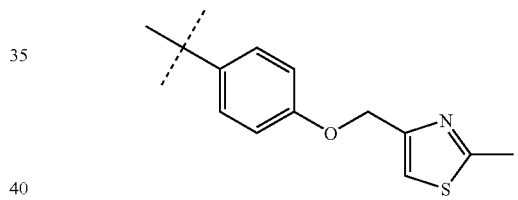

According, other suitable values for $R^1$ include phenyl, pyrid-2-yl, pyrid-3-yl, pyrid-4-yl, pyrimidin-2-yl, pyrimidinyl-4-, pyrazin-2-yl, pyrazin-3-ylyl or pyridazin-3-yl, pyridazin-4-yl or triazinyl; or mono- or di-halo substituted phenyl, such mono- or di-fluoro substituted phenyl.

As defined above, $R^2$ is $C_1$-$C_6$Alk, but especially $C_0$-$C_3$alkanediylcarbocyclyl, $C_0$-$_3$alkanediylheterocyclyl, any of which species can be substituted with up to 3 substituents independently selected from $R^{10}$. The optional substituent is preferably one or two members chosen from halo, oxo, cyano, $C_1$-$C_6$Alk, $C_0$-$C_3$alkanediylcarbocyclyl, $C_0$-$C_3$alkanediylheterocyclyl, Y—NRaRb, Y—O—Rb; where Y is a bond or $C_1$-$C_3$Alk, Ra is H or $C_1$-$C_3$Alk and Rb is H or $C_1$-$C_3$Alk. Currently favoured substituents include fluoro, $C_1$-$C_3$Alk, methylenecarbocyclyl or methyleneheterocyclyl, but especially a substituent such as optionally substituted carbocyclyl or heterocyclyl, for example in the para position of the R cyclic group.

Conveniently, the $C_0$-$C_3$alkanediyl linker moiety of such $C_0$-$C_3$alkanediylcarbocyclyl or $C_0$-$C_3$alkanediylheterocyclyl species as $R^2$ or the optional substituent thereto defines methylene or even more preferably a bond, i.e. $R^2$ or the substituent is simply an optionally substituted carbocyclyl or heterocyclyl, such as optionally substituted phenyl or optionally substituted pyridyl, pyrazinyl, pyrimidinyl or pyridazinyl Accordingly suitable values for $R^2$ include phenyl, pyrid-2-yl, pyrid-3-yl, pyrid-4-yl, pyrimidin-2-yl, pyrimidiny-4-yl, pyrazin-2-yl, pyrazin-3-ylyl or pyridazin-3-yl, pyridazin-4-yl or triazinyl; or phenyl substituted, especially in the para position with an aryl carbocyclic ring such as phenyl or heterocyclic ring, such as heteroarylic group as defined below, for example pyrid-2-yl, pyrid-3-yl or pyrid-4-yl.

Turning now to the terminal amide A', one convenient embodiment comprises a bicyclic ring system comprising a first 5 or 6 membered saturated ring optionally containing an oxygen hetero atom, and optionally substituted with hydroxy or methyl, having fused thereto a second 5 or 6 membered unsaturated ring optionally containing one or two hetero atoms selected from S, O and N, and optionally mono- or di-fluoro substituted.

Conveniently in this embodiment the bond to the amide and rest of the molecule extends from carbon 1 of said saturated ring. Suitably the optional hydroxy substitutent in this embodiment is at carbon 2 of said saturated ring. Alternatively an oxygen hetero atom is provided, typically at position 3 of a 5 membered saturated ring or position 4 of a 6 membered saturated ring.

The second ring in this embodiment of A' is conveniently 5-membered and comprises a sulphur hetero atom or an oxygen hetero atom. Alternatively, the said second ring is typically a fused pyridyl as described in WO9845330 or an optionally substituted phenyl, for example a fused phenyl wherein the substituent is mono- or di-fluoro.

Representative A' groups in this embodiment of the invention include:

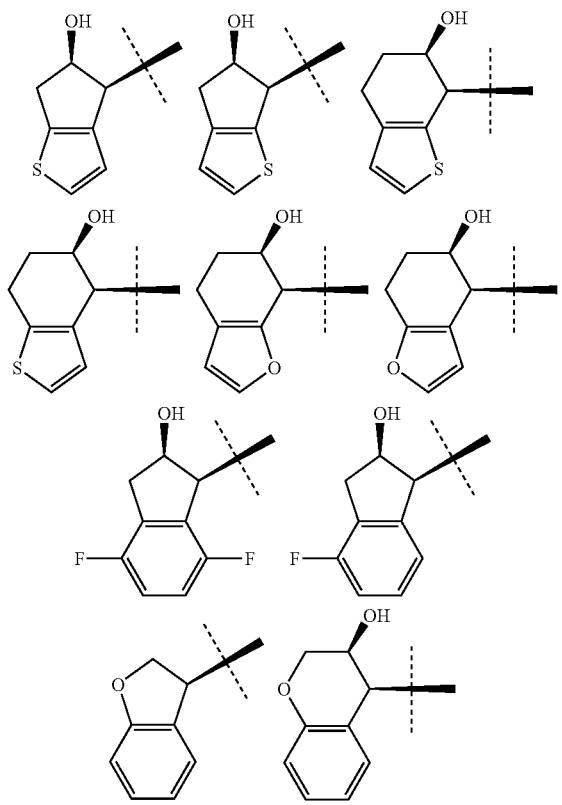
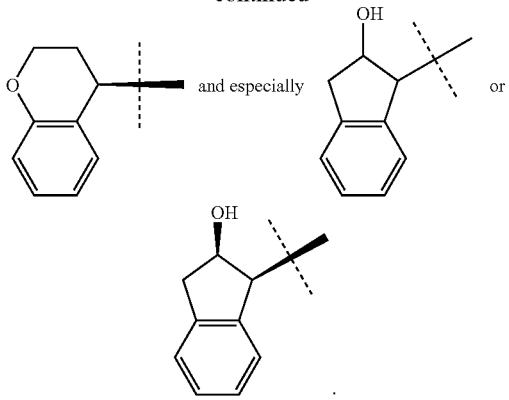

An alternative embodiment of the compounds of the invention includes those wherein A' is a group of formula (II), thereby defining a compound of the formula:

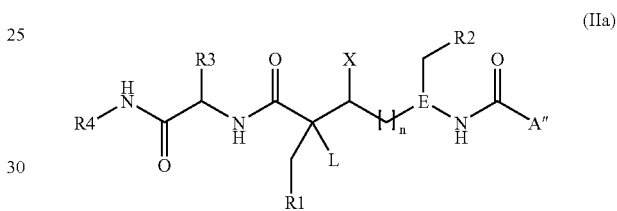

(IIa)

A further alternative embodiment of the compounds of the invention includes those wherein A' is a group of formula (II'), thereby defining a compound of the formula:

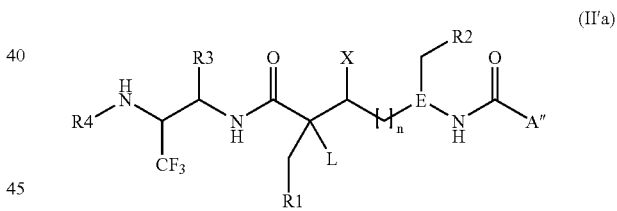

(II'a)

As recited above $R^3$ is H; or $R^3$ is $C_1$-$C_6$Alk, $C_0$-$C_3$alkanediylcarbocyclyl, $C_{0-3}$alkanediylheterocyclyl, any of which is optionally substituted with up to three substituents independently selected from $R^{11}$. Convenient values for $R^3$ include optionally substituted $C_0$-$C_3$alkylheterocycylyl and especially H or optionally substituted $C_1$-$C_6$Alk. Favoured $R^3$ values include $C_1$-$C_6$Alk such as isopropyl or t-butyl optionally substituted with hydroxy or methoxy or halo, such as fluoro.

Preferred values for $R^3$ are isopropyl, t-butyl, 2-fluoro-1-methylethyl, 2-hydroxy-1-methylethyl, 2-methoxy-1-methylethyl, 2-fluoro-1,1-dimethylethyl, 2-hydroxy-1,1-dimethylethyl and 2-methoxy-1,1-dimethylethyl.

The optional substituent to $R^3$ is as defined above. Representative values include oxo, cyano or especially halo or Y—O—Ra, where Y is a bond or $C_1$-$C_3$Alk and Ra is H or $C_1$-$C_3$Alk.

As recited above $R^4$ in Formulae I, IIa and II'a is $C_1$-$C_6$Alk, $C_0$-$C_3$alkanediylcarbocyclyl or $C_0$-$C_3$alkanediylheterocyclyl, any of which is optionally substituted with up to three substituents independently selected from $R^{10}$. Favoured values of $R^4$ include optionally substituted $C_1$-$C_6$Alk, especially methyl or ethyl or optionally substituted methyl or ethyl.

Convenient optional substituents to $R^4$ include halo, oxo, cyano, azido, nitro, $C_1$-$C_6$Alk, $C_0$-$C_3$alkanediylcarbocyclyl, $C_0$-$C_3$alkanediylheterocyclyl, Y—NRaRb or Y—O—Rb wherein;

Y is a bond or $C_1$-$C_3$Alk;
Ra is H or $C_1$-$C_3$Alk;
Rb is H or $C_1$-$C_6$Alk, $C_0$-$C_3$alkanediylcarbocyclyl or $C_0$-$C_3$alkanediylheterocyclyl.

Preferred values for $R^4$ are fluoroethyl, difluoroethyl, trifluoroethyl and methoxyethyl.

Preferred optional substituents to $R^4$ include halo, oxo, $C_1$-$C_6$Alk, $C_0$-$C_3$alkanediylcarbocyclyl, $C_0$-$C_3$alkanediylheterocyclyl or Y—O—Rb, especially halo or Y—O—Rb.

Formula II may comprise the S or R stereochemistry at the chiral centre to which $R^3$ is attached, or a racemate thereof, but it is currently preferred that it has the stereochemistry shown in the partial structure:

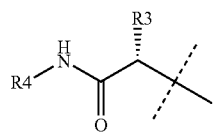

(II)

Alternatively A' may comprise the substructure:

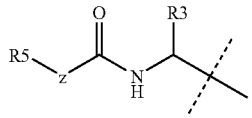

(III)

where $R^3$ is H; or $R^3$ is $C_1$-$C_6$Alk, $C_0$-$C_3$alkanediylcarbocyclyl, $C_{0-3}$alkanediylheterocyclyl, any of which is optionally substituted with up to three substituents independently selected from $R^{11}$; $R^5$ is $C_1$-$C_6$Alk, $C_0$-$C_3$alkanediylcarbocyclyl, $C_{0-3}$alkanediylheterocyclyl, any of which is optionally substituted with up to three substituents independently selected from $R^{10}$; and Z is bond, —NH—, —O—; Preferred values for $R^3$ are as defined above in respect of formula II.

Formula III may comprise the S or R stereochemistry at the chiral centre to which $R^3$ is attached, or a racemate thereof, but it is currently preferred that it has the stereochemistry shown in the partial structure:

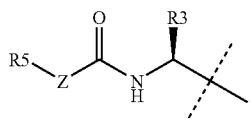

(III)

Currently preferred values for Z is O. Favoured values of $R^5$ include optionally substituted $C_1$-$C_6$Alk, especially methyl or optionally substituted methyl.

A favoured value for A' is formula IV, thus defining a compound of the formula

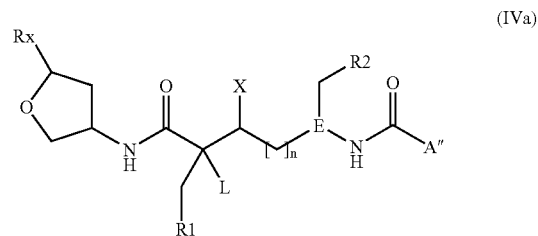

(IVa)

Representative values for formula IV include monocyclic furans where Rx is H, $C_1$-$C_3$alkyloxy, $C_1$-$C_3$ straight or branched alkyl optionally substituted with halo, hydroxy, $C_1$-$C_3$alkyloxy. Representative values within this series include those wherein Rx is H, or wherein Rx is $C_1$-$C_3$Alk substituted at chain carbon 1 with halo, hydroxy or $C_1$-$C_2$Alk. Favoured values include those wherein Rx is hydroxymethyl, 1-hydroxyethyl, 1-hydroxypropyl, fluoromethyl, 1-fluoroethyl or 1-fluoropropyl and those wherein Rx is methoxymethyl, ethoxymethyl, 1-methoxyethyl, 1-ethoxyethyl, 1-methoxypropyl or 1-ethoxypropyl. Specially preferred compounds according to formula IVa are those wherein n is 1 and/or L is OH.

Alternatively Rx defines a further furanyl or pyranyl ring fused to the depicted furan and optionally substituted with halo or $C_1$-$C_3$Alk. Representative examples include those wherein the heterocyclic oxygen is located as follows:

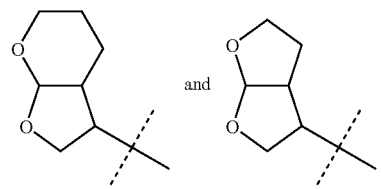

and

Turning now to the order other terminal amide A", as defined above, this is selected from formula V, VI, VII or VIII.

Representative values for formula VI, especially when A' is of formula II, IV or a bicyclic ring system, include those of the formula:

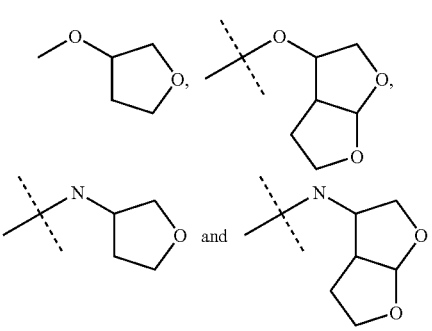

and

Favoured compounds according to this embodiment include compounds according to formulae VIa and VIb:

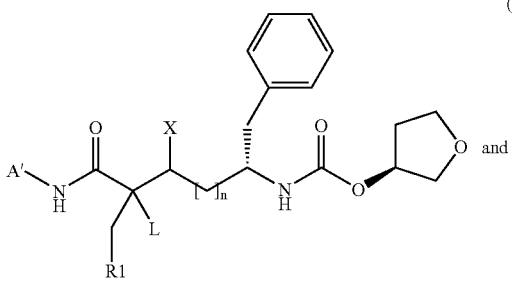

(VIa)

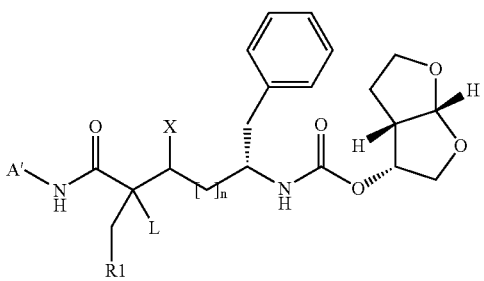

(VIb)

Further favoured compounds according to this embodiment include compounds according to formulae VIc and VId:

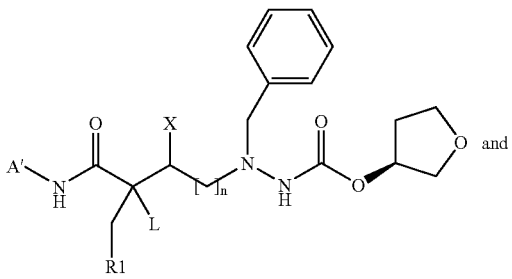

(VIc)

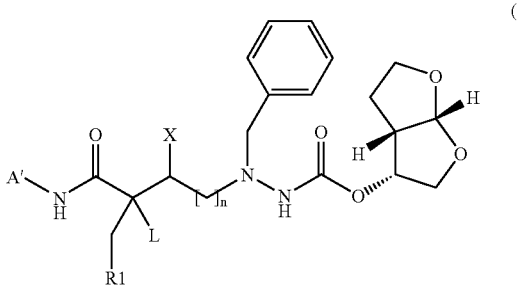

(VId)

Specially preferred compounds according to formula VIa, VIb, VIc and VId are those wherein n is 1, $R^1$ is phenyl and/or L is OH.

Suitable building blocks for the preparation of compounds according to this embodiment of the invention are described herein and in WO99/48885 and WO94/05639.

Conveniently A" is of formula V, thus defining a compound of the formula:

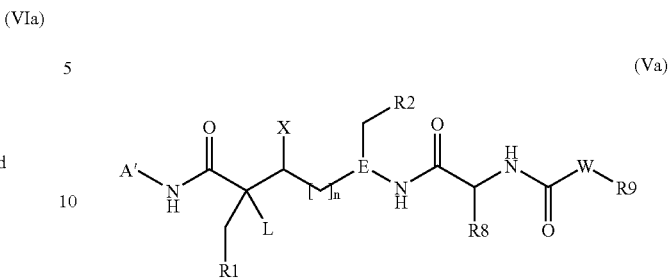

(Va)

As recited above, $R^8$ is H; or $R^8$ is $C_1$-$C_6$Alk, $C_0$-$C_3$alkanediylcarbocyclyl, $C_{0-3}$alkanediylheterocyclyl, any which is optionally substituted with up to three substituents independently selected from $R^{11}$. Conveniently $R^8$ is H, optionally substituted $C_1$-$C_6$Alk or optionally substituted $C_0$-$C_3$alkanediylcarbocyclyl. Currently favoured values for $R^8$ include H or optionally substituted $C_1$-$C_6$Alk, especially i-propyl or t-butyl.

$R^8$ is optionally substituted with 1 to 3 members independently selected from $R^{11}$. Representative optional substituents include oxo, cyano, $C_1$-$C_3$Alk or especially halo or Y—O—Ra, where Y is a bond or $C_1$-$C_3$Alk and Ra is H or $C_1$-$C_3$Alk.

As recited above, $R^9$ is $C_1$-$C_6$Alk, $C_0$-$C_3$alkanediylcarbocyclyl, $C_{0-3}$alkanediylheterocyclyl, any of which is optionally substituted with up to three substituents independently selected from $R^{10}$; and W is a bond, —NH— or —O—. Conveniently, $R^9$ is optionally substituted $C_1$-$C_6$Alk or $C_0$-$C_3$alkanediylcarbocyclyl, especially optionally substituted methyl, or unsubstituted methyl.

Representative optional substituents to $R^9$ include halo, oxo, cyano, azido, nitro, $C_1$-$C_6$Alk, $C_0$-$C_3$alkanediylcarbocyclyl, $C_0$-$C_3$alkanediylheterocyclyl, Y—NRaRb or Y—O—Rb where Y is a bond or $C_1$-$C_3$Alk, Ra is H or $C_1$-$C_3$Alk and Rb is H or $C_1$-$C_6$Alk, $C_0$-$C_3$alkanediylcarbocyclyl or $C_0$-$C_3$alkanediylheterocyclyl. Particularly preferred optional substituents, for example when $R^9$ is methyl include halo, oxo, $C_1$-$C_6$Alk, $C_0$-$C_3$alkanediylcarbocyclyl, $C_0$-$C_3$alkanediylheterocyclyl or Y—O—Rb.

When A" is of formula V, it is currently preferred that W is —O—.

Formula V may comprise the S or R stereochemistry at the chiral centre to which $R^8$ is attached, or a racemate thereof, but it is currently preferred that it has the stereochemistry shown in the partial structure:

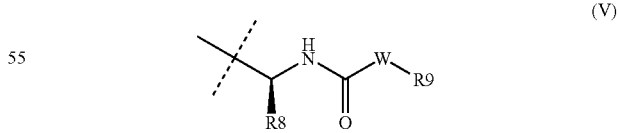

(V)

One embodiment when A" is according to formula V includes compounds wherein $R^9$ is an optionally substituted heterocyclyl either directly bonded to W, (i.e. $C_0$) or bonded to W via an $C_1$-$C_3$alkanediyl chain for example a methylene chain (i.e. $C_1$).

Preferred compounds according to this embodiment include those having the structure according to formulae Va and Vb:

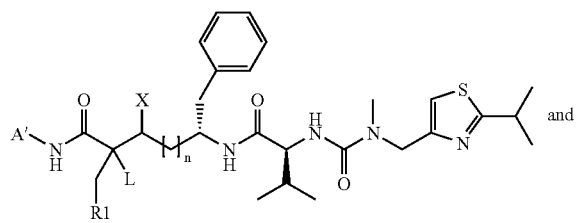

(Va)

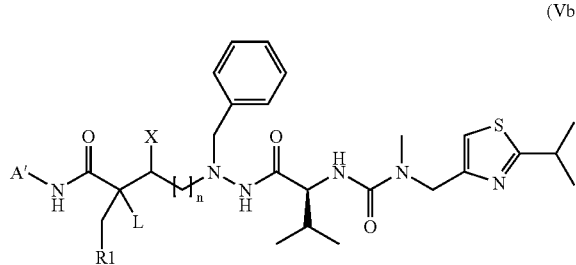

(Vb)

Specially preferred compounds according to formulae Va and Vb are those wherein n is 1, $R^1$ is phenyl and/or L is OH.

Suitable building blocks for the preparation of compounds according to this embodiment of the invention are described herein and in WO98/00410 and WO96/039398.

Another embodiment when A" is according to formula V includes compounds wherein W is a bond and $R^9$ is $C_0$-$C_3$alkanediylcarbocyclyl or $C_0$-$C_3$alkanediylheterocyclyl, the carbocyclyl and heterocyclyl being optionally substituted.

Preferred compounds according to this embodiment include those having the structure according to formulae Vc and Vd:

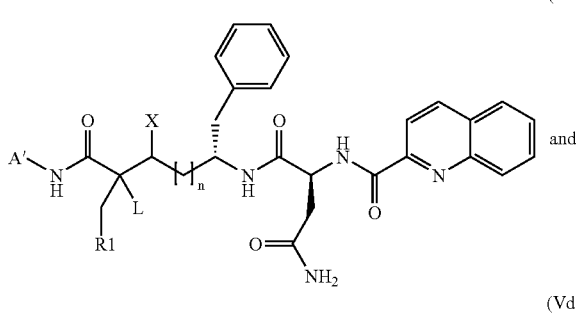

(Vc)

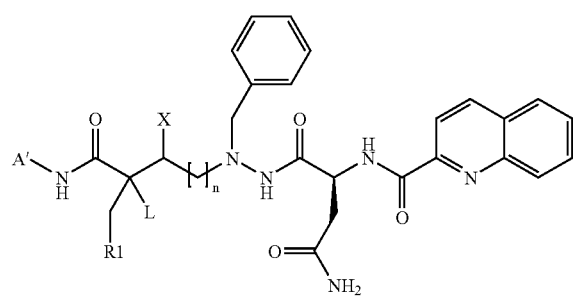

(Vd)

Specially preferred compounds according to formula Vc and Vd are those wherein n is 1, $R^1$ phenyl and/or L is OH Suitable building blocks for the preparation of compounds according to this embodiment of the invention are described herein and in U.S. Pat. No. 5,196,438.

When A" is of formula VII, it is currently preferred that $R^8$ is as described above and $R^9$ is $C_1$-$C_6$Alk such as methyl.

Conveniently A" is of formula VIII, thus defining compounds of formula VIIIa:

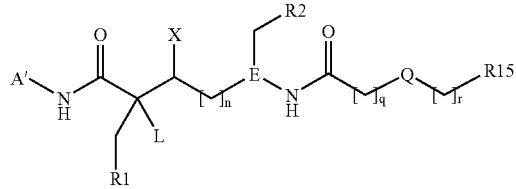

(VIIIa)

As recited above, $R^{15}$ is carbocyclyl or heterocyclyl, any of which is optionally substituted with up to three substituents independently selected from $C_1$-$C_3$Alk, hydroxy, oxo, halo, Q is O, $NR^8$ or a bond and r and q are independently 0 or 1.

Representative values for $R^{15}$ are 5 to 6 membered, optionally substituted, aromatic rings containing 0 to 2 heteroatoms, the heteroatoms being independently selected from N, O and S.

Convenient optional substituents to $R^{15}$ include $C_1$-$C_3$Alk, such as methyl, ethyl, propyl or isopropyl.

Representative compounds in this embodiment of the invention are those wherein Q is a bond and r and q are both zero.

Preferred compounds according to this embodiment are those with the structures according to formulae VIIIb and VIIIc:

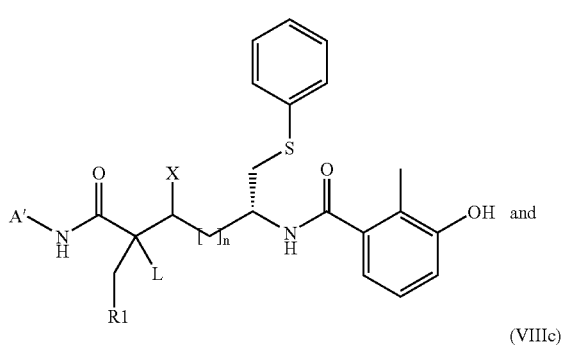

(VIIIb)

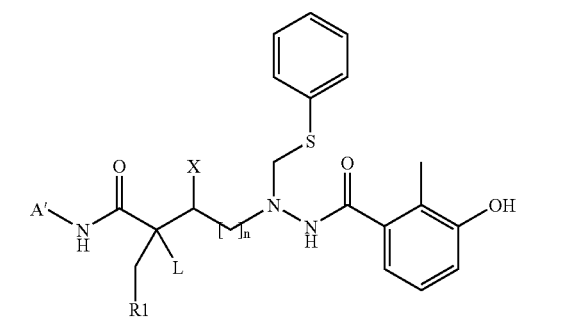

(VIIIc)

Specially preferred compounds according to formula VIIIb and VIIIc are those wherein n is 1, $R^1$ is phenyl and/or L is OH.

Suitable building blocks for the preparation of compounds according to this embodiment of the invention are described herein and in U.S. Pat. No. 5,484,926 and U.S. Pat. No. 5,952,343.

Further favoured compounds wherein A" is according to formula VIII are those wherein Q is O.

Preferred compounds according to this embodiment include those having the structures according to formulae VIIId, VIIIe, VIIIf and VIIIg:

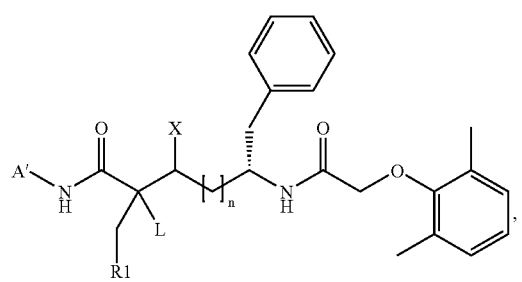
(VIIId)

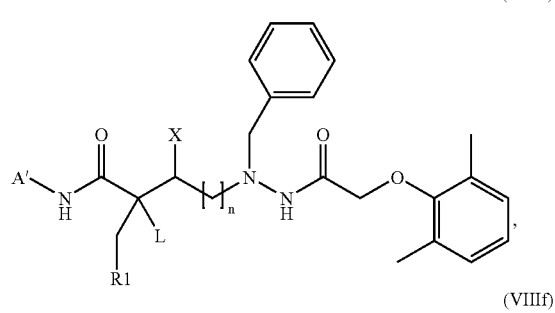
(VIIIe)

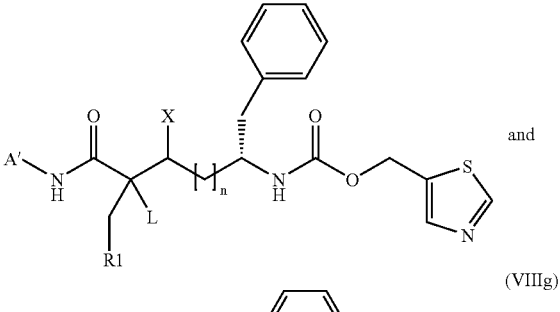
(VIIIf)

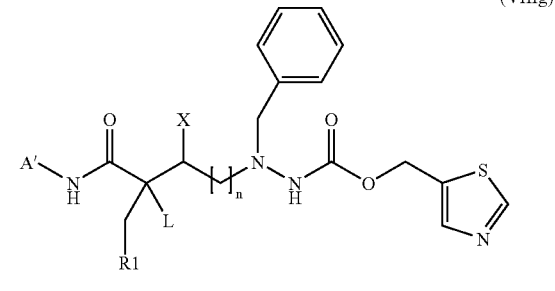
(VIIIg)

Specially preferred compounds according to formula VIIId, VIIIe, VIIIf and VIIIg are those wherein n is 1, $R^1$ is phenyl and/or L is OH.

Suitable building blocks for the preparation of compounds according to this embodiment of the invention are described herein and in WO98/00410 and WO96/39398.

Further favoured compounds wherein A" is according to formula VIII are those wherein Q is $CR^8$.

Preferred compounds according to this embodiment include those having the structure according to formulae VIIIh and VIIIi:

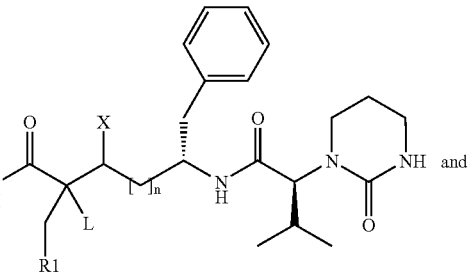
(VIIIh)

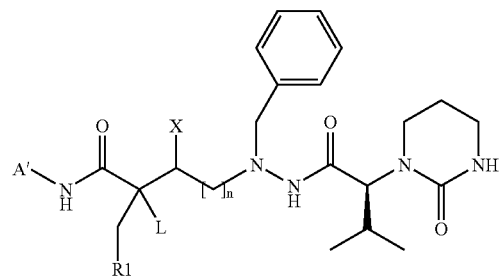
(VIIIi)

Specially preferred compounds according to formula VIIIh and VIIIi are those wherein n is 1, $R^1$ is phenyl and/or L is OH.

Suitable building blocks for the preparation of compounds according to this embodiment of the invention are described herein and in U.S. Pat. No. 6,372,905 and WO97/21685.

Convenient intermediates specially useful for the synthesis of compounds of formula (I) wherein n is 0, include epoxides having the general structure depicted below:

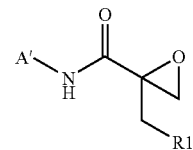

wherein A' and $R^1$ are as defined above.

Further intermediates, specially useful for the synthesis of compounds of formula (I) wherein n is 1, include epoxides and alcohols having the structures shown below:

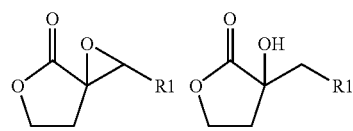

wherein $R^1$ is as defined above.

'$C_0$-$C_3$alkanediyl-O—$C_1$-$C_3$alkyl' as applied herein is meant to include $C_1$-$C_3$alkoxy groups such as methoxy, ethoxy, n-propoxy, isopropoxy directly bonded (i.e. $C_0$) or through an intermediate methylene, ethanediyl, 1,3-propanediyl or 1,3-propanediyl chain.

'$C_1$-$C_6$Alk' as applied herein is meant to include straight and branched aliphatic carbon chain substituents containing from 1 to 6 carbon atoms, such as methyl, ethyl, n-propyl, isopropyl, n-butyl, isobutyl, t-butyl, pentyl, isopentyl and hexyl and any simple isomers thereof. The Alk group may have an unsaturated bond. Additionally, any C atom in $C_1$-$C_6$Alk may optionally be substituted by one, two or where valence permits three halogens and/or a heteroatom S, O, NH. If the heteroatom is located at a chain terminus then it is appropriately substituted with one or 2 hydrogen atoms, such as OH or $NH_2$. Preferably the $C_1$-$C_6$Alk is small, saturated and unsubstituted or substituted with halo such as fluoro. $C_1$-$C_4$Alk and $C_1$-$C_5$Alk have the corresponding meaning to $C_1$-$C_6$Alk adjusted as necessary for the carbon number. Me denotes a methyl group.

'$C_1$-$C_3$Alk' as applied herein is meant to include methyl, ethyl, propyl, isopropyl, cyclopropyl, any of which may be optionally substituted as described in the paragraph above or in the case of $C_2$ or $C_3$, bear an unsaturated bond such as $CH=CH_2$.

'$C_0$-$C_3$alkanediyl' as applied herein is meant to include bivalent straight and branched aliphatic carbon chains such as methylene, ethanediyl, 1,3-propanediyl, 1,2-propanediyl.

'Amino' includes $NH_2$, $NHC_1$-$C_3$Alk or $N(C_1$-$C_3Alk)_2$.

'Halo' or halogen as applied herein is meant to include F, Cl, Br, I, particularly chloro and preferably fluoro.

'$C_0$-$C_3$alkanediylaryl' as applied herein is meant to include a phenyl, naphthyl or phenyl fused to $C_3$-$C_7$cyclopropyl such as indanyl, which aryl is directly bonded (i.e. $C_0$) or through an intermediate methylene, ethanediylyl, 1,2-propanediyl, or 1,3-propanediyl group as defined for $C_0$-$C_3$alkanediyl above. Unless otherwise indicated the aryl and/or its fused cycloalkyl moiety is optionally substituted with 1-3 substituents selected from halo, hydroxy, nitro, cyano, carboxy, $C_1$-$C_6$Alk, $C_1$-$C_6$alkoxy, $C_1$-$C_6$alkoxy-$C_1$-$C_6$Alk, $C_1$-$C_6$alkanoyl, amino, azido, oxo, mercapto, nitro $C_0$-$C_3$alkanediylcarbocyclyl, $C_0$-$C_3$alkanediylheterocyclyl. "Aryl" has the corresponding meaning.

'$C_0$-$C_3$alkanediylcarbocyclyl' as applied herein is meant to include $C_0$-$C_3$alkanediylaryl and $C_0$-$C_3$alkanediylC$_3$-$C_7$cycloalkyl. Unless otherwise indicated the aryl or cycloalkyl group is optionally substituted with 1-3 substituents selected from halo, hydroxy, nitro, cyano, carboxy, $C_1$-$C_6$Alk, $C_1$-$C_6$alkoxy, $C_1$-$C_6$alkoxyC$_1$-$C_6$Alk, $C_1$-$C_6$alkanoyl, amino, azido, oxo, mercapto, nitro, $C_0$-$C_3$alkanediylcarbocyclyl and/or $C_0$-$C_3$alkanediylheterocyclyl. "Carbocyclyl" has the corresponding meaning, i.e. where the $C_0$-$C_3$alkanediyl linkage is absent '$C_0$-$C_3$alkanediylheterocycylyl' as applied herein is meant to include a monocyclic, saturated or unsaturated, heteroatom-containing ring such as piperidinyl, morpholinyl, piperazinyl, pyrazolyl, imidazolyl, oxazolyl, isoxazolyl, thiazinolyl, isothiazinolyl, thiazolyl, oxadiazolyl, 1,2,3-triazolyl, 1,2,4-triazolyl, tetrazolyl, furanyl, thienyl, pyridyl, pyrimidinyl, pyridazinyl, pyrazinyl, pyrazolyl, or any of such groups fused to a phenyl ring, such as quinolinyl, benzimidazolyl, benzoxazolyl, benzisoxazolyl, benzothiazinolyl, benzisothiazinolyl, benzothiazolyl, benzoxadiazolyl, benzo-1,2,3-triazolyl, benzo-1,2,4-triazolyl, benzotetrazolyl, benzofuranyl, benzothienyl, benzopyridyl, benzopyrimidinyl, benzopyridazinyl, benzopyrazinyl, benzopyrazolyl etc, which ring is bonded directly i.e. ($C_0$), or through an intermediate methyl, ethyl, propyl, or isopropyl group as defined for $C_0$-$C_3$alkanediyl above. Any such non-saturated rings having an aromatic character may be referred to as heteroaryl herein. Unless otherwise indicated the hetero ring and/or its fused phenyl moiety is optionally substituted with 1-3 substituents selected from halo, hydroxy, nitro, cyano, carboxy, $C_1$-$C_6$Alk, $C_1$-$C_6$alkoxy, $C_1$-$C_6$alkoxyC$_1$-$C_6$Alk, $C_1$-$C_6$alkanoyl, amino, azido, oxo, mercapto, nitro, $C_0$-$C_3$-carbocyclyl, $C_0$-$C_3$heterocyclyl. "Heterocyclyl" and "Heteroaryl" has the corresponding meaning, i.e. where the $C_0$-$C_3$alkanediyl linkage is absent.

Typically the terms 'optionally substituted $C_0$-$C_3$alkanediylcarbocyclyl' and 'optionally substituted $C_0$-$C_3$alkanediylheterocyclyl' refers preferably to substitution of the carbocyclic or heterocyclic ring.

Typically heterocyclyl and carbocyclyl groups are thus a monocyclic ring with 5 or especially 6 ring atoms, or a bicyclic ring structure comprising a 6 membered ring fused to a 4, 5 or 6 membered ring.

Typical such groups include $C_3$-$C_8$cycloalkyl, phenyl, benzyl, tetrahydronaphthyl, indenyl, indanyl, heterocyclyl such as from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, any of which may be optionally substituted as defined herein.

The saturated heterocycle thus includes radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidinylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione, whereas the unsaturated heterocycle include radicals with an aromatic character such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl. In each case the heterocycle may be condensed with a phenyl ring to form a bicyclic ring system.

The compounds of the invention can form salts which form an additional aspect of the invention. Appropriate pharmaceutically acceptable salts of the compounds of Formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. The compounds of Formula I may in some cases be isolated as the hydrate.

It will be appreciated that the invention extends to prodrugs, solvates, complexes and other forms releasing a compound of formula I in vivo.

While it is possible for the active agent to be administered alone, it is preferable to present it as part of a pharmaceutical formulation. Such a formulation will comprise the above defined active agent together with one or more acceptable carriers/excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

The appropriate dosage will depend upon the indications and the patient, and is readily determined by conventional animal drug metabolism and pharmacokinetics (DMPK) or clinical trials and in silico prediction software.

In treating HIV, the compounds of formula I are typically administered in an amount to achieve a plasma level of around 100 to 5000 nM, such as 300 to 2000 nM. This corresponds to a dosage rate, depending on the bioavailability of the formulation, of the order 0.01 to 10 mg/kg/day, preferably 0.1 to 2 mg/kg/day. A typical dosage rate for a normal adult will be around 0.05 to 5 g per day, preferably 0.1 to 2 g such as 500-750 mg, in one to four dosage units per day. As with all pharmaceuticals, dosage rates will vary with the size and metabolic condition of the patient as well as the severity of the infection and may need to be adjusted for concomitant medications.

In general dosages of from about 3 mg to approximately 1.6 grams per person per day, divided into 1 to 3 single doses, are suitable. A typical dosage for adult patients is 50-800, more preferably 400-600 twice, or most preferably once daily. As elaborated below HIV inhibitors are typically co-administered in a unit dosage form with other HIV inhibitors or metabolism modifying agents and the dosage regime (QQ, BiD TiD, fast/with food etc) for such co-administered drugs will of course necessitate concomitant adjustment of the dosage regime for formula I As is good prescribing practice with antiviral therapy, the compounds of formula I are typically co-administered with other HCV therapies to avoid the generation of drug escape mutants. However, certain antifectives can induce a synergistic response, allowing one or both of the active ingredients to be administered at a lower dose that the corresponding monotherapy. For example in drugs prone to rapid metabolism by Cyp3A4, co-dosing with the HIV protease inhibitor ritonavir can allow lower dosage regimes to be administered. The compound of the invention and the or each further antiviral agent are typically co-administered at molar ratios reflecting their respective activities and bioavailabilities. Generally such ratio will be of the order of 25:1 to 1:25, relative to the compound of formula I, but may be lower, for instance in the case of cytochrome antagonists such as ritonavir.

Representative HIV antivirals include NRTI such as alovudine (FLT), zudovudine (AZT, ZDV), stavudine (d4T, Zerit), zalcitabine (ddC), didanosine (ddI, Videx), abacavir, (ABC, Ziagen), lamivudine (3TC, Epivir), emtricitabine (FTC, Emtriva), racevir (racemic FTC), adefovir (ADV), entacavir (BMS 200475), alovudine (FLT), tenofovir disoproxil fumarate (TNF, Viread), amdoxavir (DAPD), D-d4FC (DPC-817), -dOTC (Shire SPD754), elvucitabine (Achillion ACH-126443), BCH 10681 (Shire), SPD-756, racivir, MIV-606 (Medivir), D-FDOC, GS7340, INK-20 (thioether phospholipid AZT, Kucera), 2'3'-dideoxy-3'-fluoroguanosine (FLG) & its prodrugs such as MIV-210, reverset (RVT, D-D4FC, Pharmasset DPC-817).

Representative NNRTI include delavirdine (Rescriptor), efavirenz (DMP-266, Sustiva), nevirapine (BIRG-587, Viramune), (+)calanolide A and B (Advanced Life Sciences), capravirine (AG1549f S-1153; Pfizer), GW-695634 (GW-8248; GSK), MIV-150 (Medivir), MV026048 (R-1495;

Medivir AB/Roche), NV-05 2 2 (Idenix Pharm.), R-278474 (Johnson & Johnson), RS-1588 (Idenix Pharm.), TMC-120/125 (Johnson & Johnson), TMC-125 (R-165335; Johnson & Johnson), UC-781 (Biosyn Inc.) and YM215389 (Yamanoushi).

Representative HIV protease inhibitors include PA-457 (Panacos), KPC-2 (Kucera Pharm.), 5 HGTV-43 (Enzo Biochem), amprenavir (VX-478, Agenerase), atazanavir (Reyataz), indinavir sulfate (MK-639, Crixivan), Lexiva (fos-amprenavir calcium, GW-433908 or 908, VX-175), ritonavir (Norvir), lopinavir+ritonavir (ABT-378, Kaletra), tipranavir, nelfinavir mesylate (Viracept), saquinavir (Invirase, Fortovase), AG1776 (JE-2147, KNI-764; Nippon Mining Holdings), AG-1859 (Pfizer), DPC-681/684 (BMS), GS224338 (Gilead Sciences), KNI-272 (Nippon Mining Holdings), Nar-DG-35 (Narhex), P(PL)-100 (P-1946; Procyon Biopharma), P-1946 (Procyon Biopharma), R-944 (Hoffmann-LaRoche), RO-0334649 (Hoffmann-LaRoche), TMC-114 (Johnson & Johnson), VX-385 (GW640385; GSK/Vertex), VX-478 (Vertex/GSK).

Other HIV antivirals include entry inhibitors, including fusion inhibitors, inhibitors of the CD4 receptor, inhibitors of the CCR5 co-receptor and inhibitors of the CXCR4 coreceptor, or a pharmaceutically acceptable salt or prodrug thereof. Examples of entry inhibitors are AMD-070 (AMD 11070; AnorMed), BlockAide/CR (ADVENTRX Pharm.), BMS 806 (BMS-378806; BMS), Enfurvirtide (T-20, R698, Fuzeon), KRH1636 (Kureha Pharmaceuticals), ONO-4128 (GW-873140, AK-602, E-913; ONO Pharmaceuticals), PRO-140 (Progenics Pharm), PRO-542 (Progenics Pharm.), SCH-D (SCH-417690; Schering-Plough), T-1249 (R724; Roche/Trimeris), TAK-220 (Takeda Chem. Ind.), TNX-355 (Tanox) and UK-427,857 (Pfizer). Examples of integrase inhibitors are L-870810 (Merck & Co.), c-2507 (Merck & Co.) and S(RSC)-1838 (shionogi/GSK).

Many HIV patients are co-infected, or prone to superinfection, with other infectious diseases. Accordingly, a further aspect of the invention provides combination therapies comprising the compound of the invention co-formulated in the same dosage unit or co-packaged with at least one further anti-infective pharmaceutical. The compound of the invention and the at least one further antinfective are administered simultaneously or sequentially, typically at doses corresponding to the monotherapy dose for the agent concerned.

Typical coinfections or superinfections include hepatitis B virus (HBV) or Hepatitis C virus (HCV). Accordingly the compound of the invention is advantageously co-administered (either in the same dosage unit, co-packaged or separately prescribed dosage unit) with at least one HCV antiviral and/or at least one HBV antiviral.

Accordingly the compound of the invention is advantageously co-administered (either in the same dosage unit, co-packaged or separately prescribed dosage unit) with at least one HCV antiviral and/or at least one HBV antiviral.

Examples of HBV antivirals include lamivudine and 2'3'-dideoxy-3'-fluoroguanosine (FLG) & its prodrugs such as the 5'-O-lacytlvalyl prodrug MIV-210. These HBV antivirals are particularly convenient as they are simultaneously active against both HBV and HIV.

Examples of HCV antiviral for co-administration with formula I include immune modifiers such as ribavirin or interferons, nucleoside HCV polymerase inhibitors or HCV protease inhibitors, many of which are currently under development.

The compounds of the invention are believed to counteract elevated LDL-cholesterol and/or triglyceride levels often appearing as a side effect of prior art HIV protease inhibitors. Accordingly the compounds of the invention are useful for replacing such prior art inhibitors in the ongoing dosage regimes of patients. Typically such patient has been or is undergoing antiretroviral therapy with one or more conventional HIV protease inhibitors and exhibits elevated plasma LDL-cholesterol and/or triglyceride levels. Such other HIV protease inhibitor(s) may be given as monotherapy or as part of an antiretroviral therapy which also includes one or more other antiretroviral drugs such as reverse transcriptase inhibitors or nonnucleoside reverse transcriptase inhibitors. Such candidates, although they may exhibit satisfactory viral suppression, may be of increased risk for hyperlipidemia and premature cardiovascular events.

The term "elevated plasma LDL-cholesterol and triglyceride levels" as used herein is based on the National Cholesterol Education Program (NCEP) clinical practice guidelines for the prevention and management of high cholesterol in adults.

In the latest guidelines issued in 2001, plasma levels of >130 mg/dL of LDLcholesterol and >150 mg/dL of triglycerides are considered elevated or "high". The process of the present invention is particularly useful for those patients having plasma triglyceride levels of >200 mg/dL and for those patients with no risk factors or previous cardiovascular events having LDL-cholesterol levels of >160 mg/dL.

The definition of "elevated" LDL-cholesterol and triglyceride levels may, of course, change in the future as the NCEP continues to evaluate heart attack risk factors. It is intended, then, that the term "elevated LDL-cholesterol and triglyceride levels" as used will be consistent with current NCEP guidelines.

In one of its aspects, the present invention involves discontinuing the offending (the drug responsible for the elevated plasma LDL-cholesterol and/or triglyceride levels) HIV protease inhibitor from the above regimen and substituting therefore an amount of the compound of formula I which is effective to inhibit HIV and to reduce plasma LDL-cholesterol and/or triglyceride levels.

The dose of the compound of the invention to be employed depends on such factors as the body weight, age and individual condition of the patient to be treated and the mode of administration.

It is believed that the compounds according to some embodiments of the invention can in certain formulations interact favourably with cytochrome P450 monooxygenase and can improve the pharmacokinetics of drugs metabolized by this enzyme, including particularly other HIV protease inhibitors such as saquinavir, indinavir, nelfinavir, araprenavir, tipanavir and lopinavir. Thus, it may act in a similar way to ritonavir described in U.S. Pat. No. 6,037,157 to increase blood levels of the coadministered HIV protease inhibitor. Conveniently and in contradistinction to ritonavir it is believed that the compound of the invention may be employed in combination therapy with other HIV protease inhibitors at its normal therapeutic dose level instead of the sub-therapeutic dose levels used with ritonavir. Any such potentiating effect on other HIV protease inhibitors which are metabolized by cytochrome P450 monooxygenase, may allow the use of the compounds of the invention concomitantly with such other HIV protease inhibitors thereby allowing reduced dosages of such other HIV protease inhibitors to be used while maintaining the same degree of viral suppression. Conceivably the compound of the invention can be used in combination with other HIV protease inhibitors to reduce LDL-cholesterol and triglyceride levels in AIDS patients undergoing protease inhibitor therapy while still maintaining the desired level of viral suppression.

The appropriate dose of the HIV protease inhibitor being combined with the compounds of the invention can be determined by the following method which was used for the atazanavir/saquinavir combination, as disclosed in WO03020206. Atazanavir is a moderate inhibitor of the cytochrome P450 3A enzyme comparable to nelfinavir and indinavir, with a Ki of 2.4 μM. The latter two compounds increase the exposure of saquinavir (dosed at 1200 mg thrice-daily (TID) by 392 and 364%, respectively, at steady-state. A multiple-dose pharmacology study was completed to evaluate if a similar increase could be expected for the combination of atazanavir and saquinavir. This study showed a greater than 3-fold increase in exposure, due to combination with atazanavir, supporting a 1200 mg once-daily saquinavir dosing, was equivalent to the currently marketed saquinavir regimen of 1200 mg TID. Using a constant dose of atazanavir the range of saquinavir doses were studied to target the saquinavir exposure (AUC (area under the curve) and CMIN (minimum concentration)) similar to those in the literature. Similarly, appropriate dosing of other HIV protease inhibitors to be used in combination with the compound of the invention can be calculated.

Compounds of the invention are typically synthesized outlined below.

A method to prepare compounds according to the present invention wherein E is N and n is 0 is by reacting a suitable epoxide with a desired hydrazide derivative as illustrated in scheme 1.

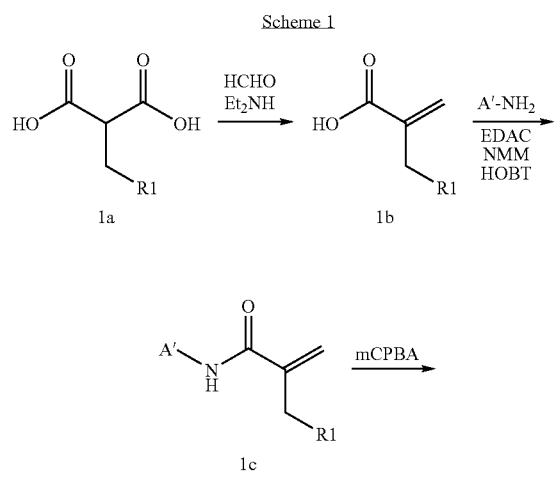

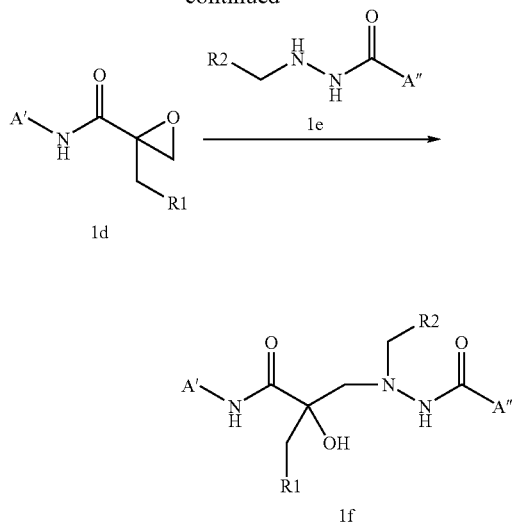

A suitable derivative of malonic acid (1a) where $R^1$ is as described above, can be transformed into an acrylic acid derivative (1b) by way of a Mannich reaction followed by in situ decarboxylation. Various derivatives of malonic acid are available commercially or they are easily prepared by the skilled person according to literature procedures. The acrylic acid can then be coupled to a desired amine A'-$NH_2$, where A' is as defined above, using standard peptide coupling conditions for example by using 1-(3-dimethylaminopropyl)-3-ethylcarbodiimide hydrochloride (EDAC), N-methylmorpholine (NMM) and 1-hydroxybenzotriazole (HOBT) or any other suitable conditions that are known by the skilled person, to give the acrylamide derivative (1c). Epoxidation of the double bond by any suitable method like using a peroxide for instance 3-chloroperoxybenzoic acid (mCPBA) provides the corresponding epoxide (1d). Subsequent opening of the formed epoxide by a suitable hydrazide (1e) optionally in the presence of titanium(IV) isopropoxide as described in JOC, 50, 1985 p. 1557 yields the tertiary alcohol (1f). If desired, the afforded hydroxy group can then be converted to a fluoride or a primary or secondary amine thus providing compounds according to general formula I wherein n is 0, X is H, E is N and L is F, $NHC_1$-$C_3$alkyl or $N(C_1$-$C_3$alkyl$)_2$, as shown in scheme 2 below.

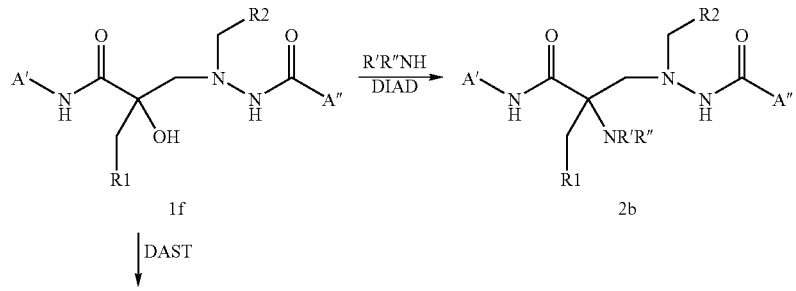

-continued

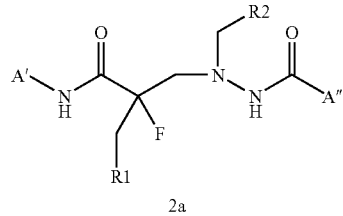
2a

R' is H or $C_1$-$C_3$alkyl
R" is H or $C_1$-$C_3$alkyl

Reaction of the alcohol (1f) with a suitable fluorinating agent such as DAST or Deoxofluor or the like in a solvent like dichloromethane as described e.g. by Singh, R. P. and Shreve, J. M. in Synthesis, 17, 1999, p. 2561-2578, yields the corresponding fluoro compound (2a). Alternatively, the hydroxy group of the alcohol (1f) can be transferred to an amine using any convenient method described in the literature. For example the Mitsunobu procedure can be used, i.e. reaction of the alcohol (1f) with an azodicarboxylate such as DIAD or the like in the presence of triphenylphosphine followed by displacement with a desired amine to provide the corresponding amino derivative (2b). An alternative route to the amine (2b) is by transformation of the hydroxy group into a leaving group such as a derivative of sulphonic acid like a mesylate, triflate, tosylate or the like by treatment with the appropriate sulphonylating agent in a solvent like for instance pyridine or dichloromethane optionally in the presence of triethylamine or the like, followed by displacement of the leaving group with a desired primary or secondary amine $NH_2C_1$-$C_3$alkyl or $NH(C_1$-$C_3$alkyl$)_2$. Alternatively, the leaving group can be displaced with azide, or the hydroxy group can be converted directly to an azide by use of an azide transfer agent like diphenyl phosphoryl azide (DPPA), subsequent reduction of the introduced azide to an amine, by for example triphenylphosphine optionally in the presence of a base like triethylamine provides compounds wherein L is $NH_2$ whereas a reductive amination of the afforded amine with a desired aldehyde or ketone provides secondary or tertiary amines.

The above described intermediates, for example the epoxide 1d, wherein A' and $R^1$ are as defined above are novel compounds and constitute a further aspect of the invention.

Various amines, A'-$NH_2$, used in scheme 1 are available commercially or alternatively they can be prepared according to literature procedures. For example, amines wherein A' is according to formula (IV) can be prepared as described by B. Samuelsson et al. in Bioorg. Med. Chem., 11, 2003, p. 1107-1115. Alternatively, they can be prepared from the corresponding alcohols A'-OH by transforming the hydroxy group to an amino group. This transformation can be effected by any suitable method known by the skilled person, for instance by converting the hydroxy group to a leaving group such as a halide like a bromide, chloride or iodide or to a derivative of sulphonic acid such as a mesylate, triflate or tosylate, followed by a nucleophilic displacement reaction with azide and finally reduction of the azide to the amine using any suitable reduction method such as catalytic hydrogenation. Suitable alcohols are described for example by A. K. Gosh et al. in J. Med. Chem., 1996, 39, 3278-3290.

A further alternative to prepare amines, A'-$NH_2$, wherein A' is according to formula (IV) is illustrated in scheme 3.

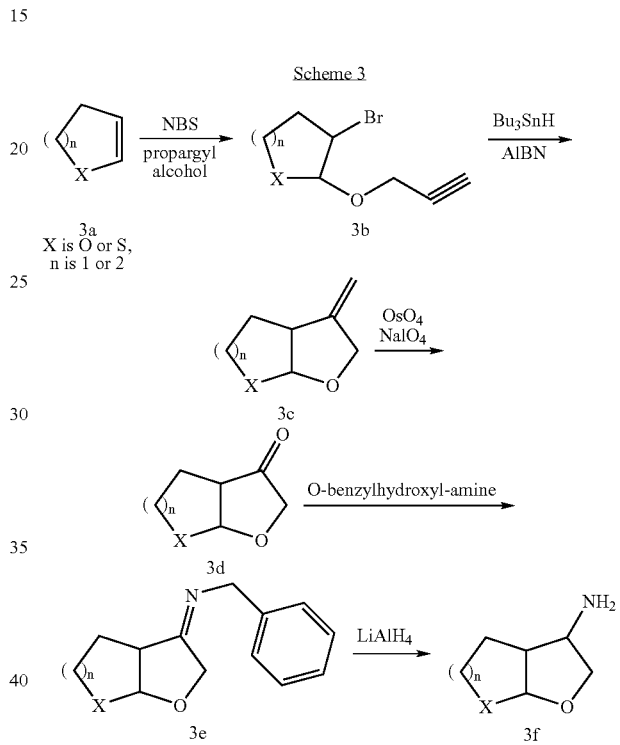

Addition of a bromide and a propargyloxy group to the double bond of the unsaturated ring (3a) effected for instance by reaction with N-bromosuccinimide and propargyl alcohol followed by a reductive ring closure reaction promoted by tri-n-butyltin hydride in the presence of a radical initiator for example 1,1'-azobis(isobutyronitrile) or the like yields bicyclic olefin (3c). The exocyclic double bond can then be cleaved oxidatively by subjecting the olefinic compound to the appropriate oxidation conditions such as treatment with osmium tertoxide in combination with sodium periodate which gives the keto derivative (3d). Reaction of the formed keto group with O-benzylhydroxylamine followed by reduction with a reducing agent like lithium aluminium hydride gives the corresponding amine (3f) as a racemic mixture. The racemic mixture can thereafter be separated according to procedures known in the art. For example, a diastereomeric mixture which can be separated by chromatographic methods, can be prepared by coupling of a chiral auxiliary compound such as a chiral amino acid for example Boc-L-phenylalanine, using standard peptide coupling methods. Separation of the mixture and thereafter cleavage of the auxiliary amino acid then provides the pure diastereomers of the desired amine (3f).

An example of the preparation of amine derivatives A'-NH$_2$ used i.a. in scheme 1 wherein A' is according to formula (II) is shown in scheme 4 below.

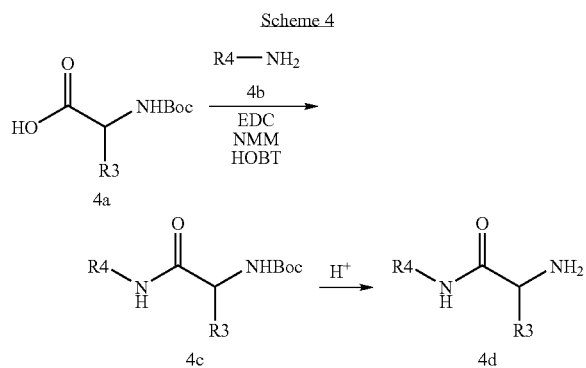

Coupling of a suitably N-protected, for example Boc protected, amino acid (4a), carrying the desired side chain R$^3$ to an amino derivative (4b), where R$^3$ and R$^4$ are as defined above, using standard peptide coupling conditions, like using coupling reagents such as EDAC, NMM and HOBT in an inert solvent like dimethylformamide gives the amide (2Bc). Removal of the N-protecting group, by acidic treatment in the case of a Boc protecting group, for example by using trifluoroacetic acid in dichloromethane, gives the amine (4d). Amino acids (4a) used in the above scheme are commercially available or they can be prepared according to literature procedures. A method to prepare amino acids carrying a branched side chain is exemplified in Scheme 4A.

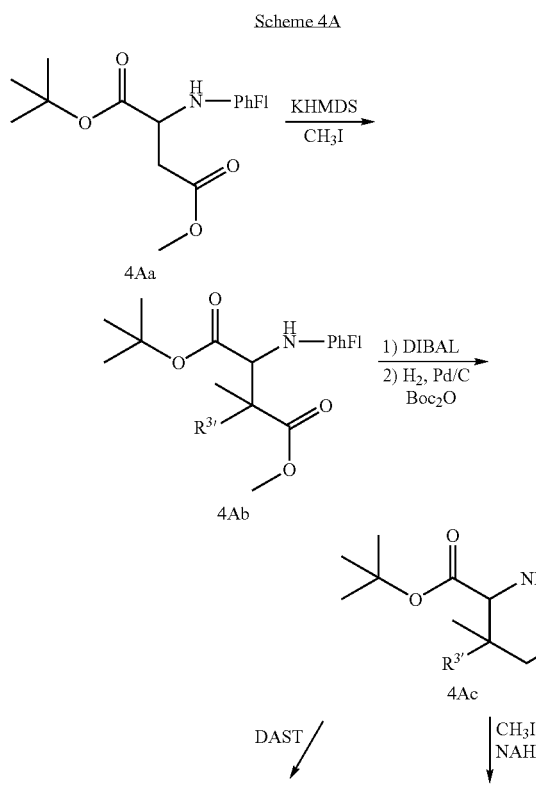

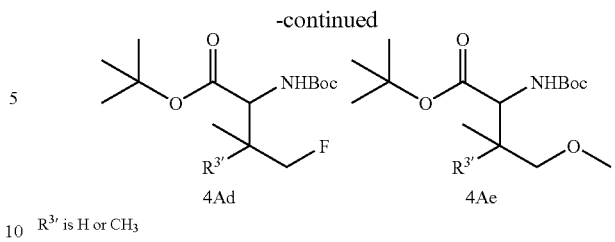

R$^{3'}$ is H or CH$_3$

Treatment of the amino acid (4Aa), achieved as described by Rapoport et al. in J. Org. Chem., 55, (1990) p. 5017-5025, with one or two successive additions of a base such as potassium bis-(trimethylsilyl) amide (KHMDS) and methyl iodide provides mono or dimethylated amino acid (4Ab) respectively. Reduction of the side chain ester using a reagent like DIBAL followed by interchanging of the PhFl group for a Boc group effected by catalytic hydrogenation in the presence of Boc$_2$O and a catalyst like Pd/C, provides the alcohol (4Ac). If desired, the hydroxy group of the afforded alcohol can subsequently be methylated for instance by treatment with a suitable methylating agent such as methyl iodide and a base like NaH which gives the methoxy compound (4Ae). Alternatively, the alcohol can be converted to the corresponding fluorocompound (4Ad) by treatment with a fluorinating agent such as DAST or the like, or any other suitable fluorinating method described herein or elsewhere can be used.

Amines, A'-NH$_2$, wherein A' is according to formula (III) can be prepared as exemplified in scheme 5.

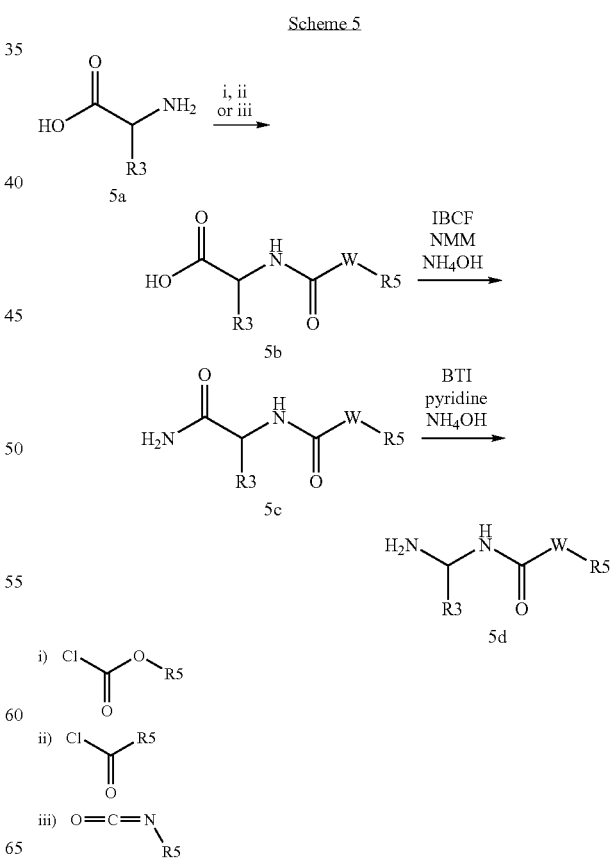

Reaction of a natural or non-natural amino acid (5a) carrying the appropriate side chain $R^3$ defined as above, with a desired acylating agent; a chloroformate (i) for the formation of compounds wherein W is O, an acid chloride (ii) for the formation of compounds wherein W is a bond or an isocyanate (iii) for the formation of compounds wherein W is NH, provides the acid (5b). The amine A'-$NH_2$ (5d) can then be achieved by transforming the acid (5b) to the corresponding primary amide (5c) for example by treatment with an ammonia solution in the presence of isobutyl chloroformate and N-methylmorpholine in a solvent like dimethoxy ethane, followed by a rearrangement reaction brought about by treatment with [bis(trifluoroacetoxy)iodo]benzene optionally in the presence of pyridine as described e.g. by J-A. Fehreentz in J. Med. Chem., 2003, 46, 1191-1203.

Hydrazide derivatives (1e) used in scheme 1 can be prepared by reaction of an acid A"COOH or a derivative thereof, for instance an acid chloride or an acid anhydride, with a hydrazine $R^2CH_2NHNH_2$ under standard peptide coupling conditions. Scheme 6 shows an example wherein A" in the acid, A"COOH is according to formula (V) as defined above.

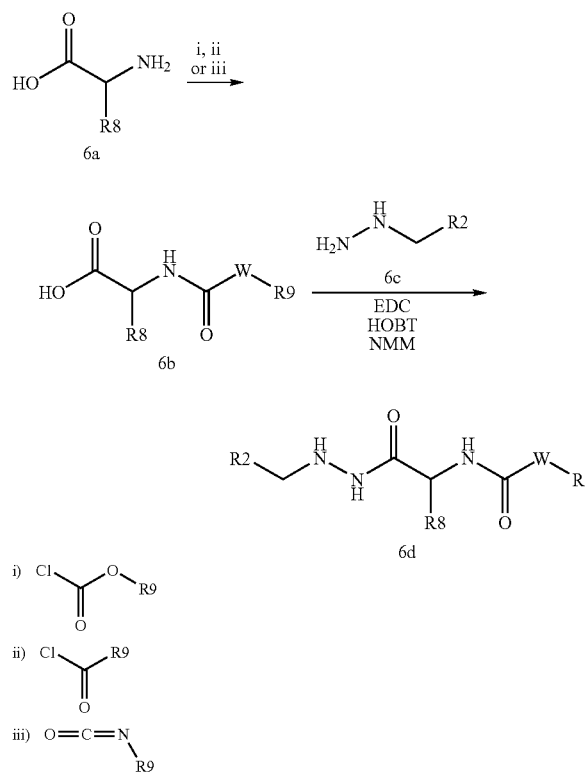

Reaction of a natural or non-natural amino acid (6a) carrying the appropriate side chain $R^8$ defined as above, with a desired acylating agent as described in scheme 3 provides the acid (6b). The hydrazide derivative (6d) can then be achieved by coupling of a hydrazine derivative (6c) which is available either commercially or in the literature, using standard peptide coupling conditions as described above.

Compounds wherein A" is according to formula (VII) can conveniently be prepared according to the above described route but with the use of a suitable sulphonylating agent like alkylsulphonyl chloride, $R^9$—S(=O)$_2$Cl, in the presence of a base like sodium hydroxide, instead of any of the depicted acylating agents i, ii or iii, in the reaction with amino acid 3a.

Hydrazides (1e) wherein A" is according to formula (VI) can be prepared by reaction of an appropriate electrophilic carbonyl compound such as a chloroformate or an activated carbonate with the hydrazine derivative $R^2CH_2NHNH_2$ as illustrated in scheme 7.

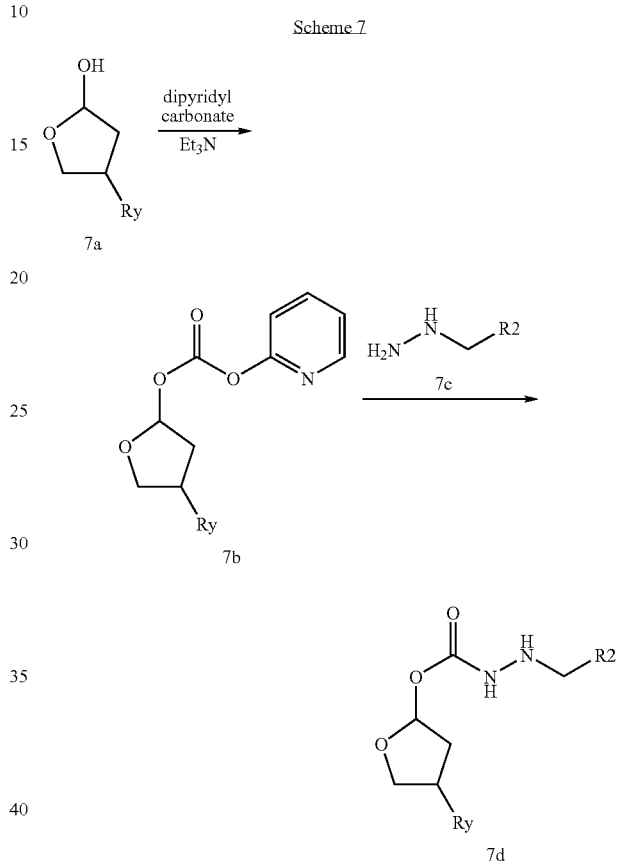

The alcohol (7a) can be converted to the corresponding activated carbonate (7b) or chloroformate by reaction of the hydroxy group with a suitable acylating agent like a carbonate such as dipyridyl carbonate or para-nitrophenyl chloroformate optionally in the presence of a base such as triethylamine or imidazole, or to a chloroformate by reaction with phosgene optionally in the presence of base like sodium hydrogen carbonate. The afforded electrophilic compound can then be reacted with a desired hydrazine derivative (7c) to give the corresponding hydrazide (7d). Alcohol (7a) is either commercially available or can be prepared for example as described by A. K. Ghosh et al. in J. Med. Chem., 1996, 39, 3278-3290.

The procedure described in scheme 7 can also be applied to other alcohols for instance optionally substituted carbocyclylmethanol, optionally substituted heterocyclylmethanol, optionally substituted carbocycloalcohol or optionally substituted heterocyclalcohol thus providing hydrazides wherein A" is according to formula (VIII) as defined above.

A route to compounds according to general formula I wherein E is N and n is 1 is depicted in scheme 8.

Scheme 8

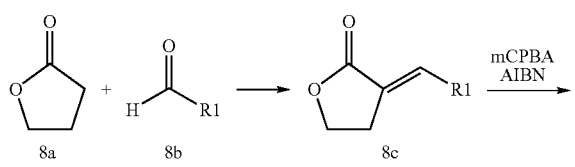

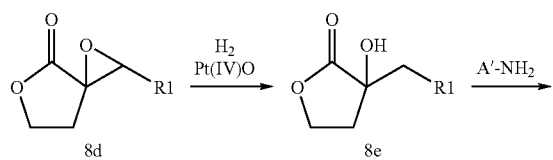

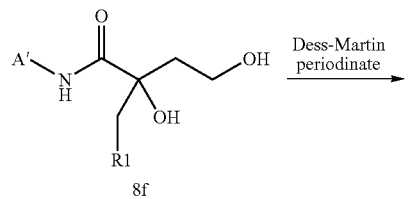

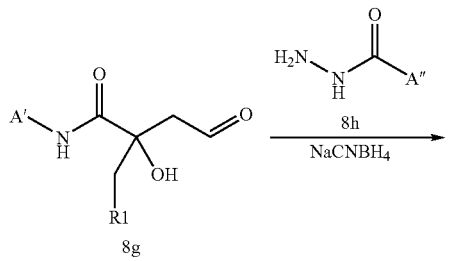

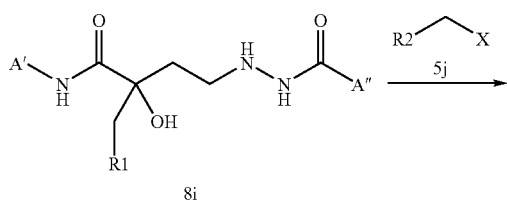

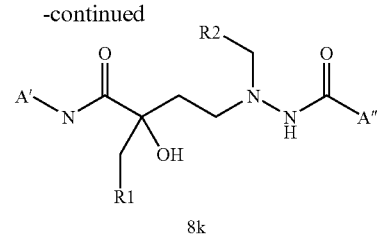

Condensation of γ-butyrolactone (8a) with a suitable aldehyde (8b) in the presence of a base like potassium t-butoxide in an inert solvent like benzene, dichloromethane or the like provides the olefinic compound (8c). Epoxidation of the double bond can then be effected for example by using mCPBA in the presence of a catalytic amount of a radical initiator such as AIBN or the like which gives the epoxide (8d). Reductive opening of the epoxide by for instance catalytic hydrogenation in the presence of a catalyst like Pt(IV)O or the like, followed by ring opening of the lactone with a desired amine, A'-NH$_2$, gives the diol (8f). Oxidation of the primary alcohol by any suitable oxidation method like for example using Dess-Martin periodinate provides the aldehyde (8 g) which subsequently can be reacted with a suitable hydrazide derivative (8 h) in a reductive amination reaction, using a reduction agent like NaCNBH$_4$, to give the hydrazide (8i). The N-substituent CH$_2$—R$^2$ can then be introduced by alkylation of the β-nitrogen of the hydrazide with a desired alkylating agent (8j) wherein R$^2$ is as defined above and X is a leaving group such as a halide like chloride, bromide or iodide or a derivative of sulphonic acid such as a triflate, mesylate or tosylate, thus providing the N-alkylated compound (8k). The above synthetic route can also be carried out starting from β-propiolactone thus giving compounds of general formula I wherein n is 0. The N-alkylated hydrazide (8k) can also be prepared more directly by reacting the aldehyde (8 g) with an already N-alkylated hydrazine derivative like compound 3d from scheme 3.

The intermediates above, such as the epoxide 8d and alcohol 8e where R$^1$ is as defined above are novel compounds and constitute another aspect of the invention.

If desired the hydroxy group of compound (8k) can be converted to a fluoride or a primary or secondary amine thus providing compounds according to general formula I wherein n is 1, X is H, E is N and L is F, NHC$_1$-C$_3$alkyl or N(C$_1$-C$_3$alkyl)$_2$, as shown in scheme 9 below.

Scheme 9

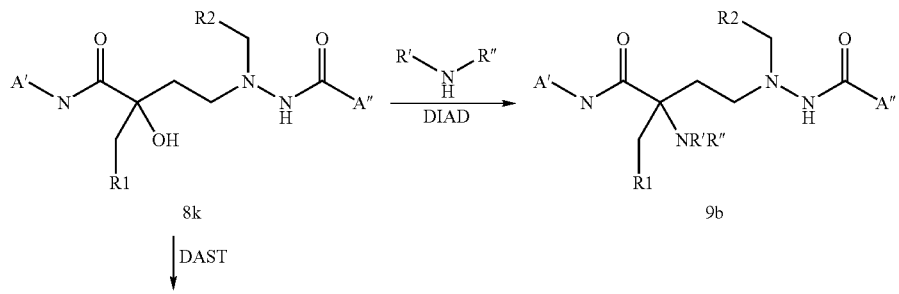

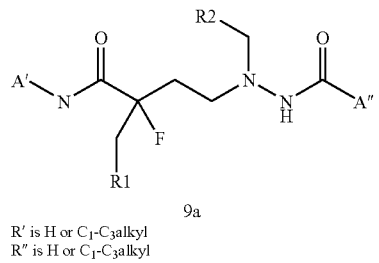

9a

R' is H or C$_1$-C$_3$alkyl
R" is H or C$_1$-C$_3$alkyl

Reaction of alcohol 8k with a suitable fluorinating agent such as DAST or Deoxofluor or the like in a solvent like dichloromethane as described e.g. by Singh, R. P. and Shreve, J. M. in Synthesis, 17, 1999, p. 2561-2578, yields the corresponding fluoro compound 9a. Alternatively, the hydroxy group of compound 8k can be transferred to an amine using any convenient method described in the literature. For example the Mitsunobu procedure can be used, i.e. reaction of the alcohol (8k) with an azodicarboxylate such as DIAD or the like in the presence of triphenylphosphine followed by displacement with a desired amine which provides the corresponding amino derivative (9b). An alternative route to the amine (9b) is by transformation of the hydroxy group into a leaving group such as a derivative of sulphonic acid like a mesylate, triflate, tosylate or the like by treatment with the appropriate sulphonylating agent in a solvent like for instance pyridine or dichloromethane optionally in the presence of triethylamine or the like, followed by displacement of the leaving group with a desired primary or secondary amine $NH_2C_1$-$C_3$alkyl or $NH(C_1$-$C_3$alkyl$)_2$. Alternatively, the leaving group can be displaced with azide, or the hydroxy group can be converted directly to an azide by use of an azide transfer agent like diphenyl phosphoryl azide (DPPA), subsequent reduction of the introduced azide to an amine, by for example triphenylphosphine optionally in the presence of a base like triethylamine provides compounds wherein L is $NH_2$ whereas a reductive amination of the afforded amine with a desired aldehyde or ketone provides secondary or tertiary amines.

Dihydroxylated or difluorinated compounds wherein n is 1, E is N and X=L=OH or F in general formula I can be prepared as depicted in scheme 10.

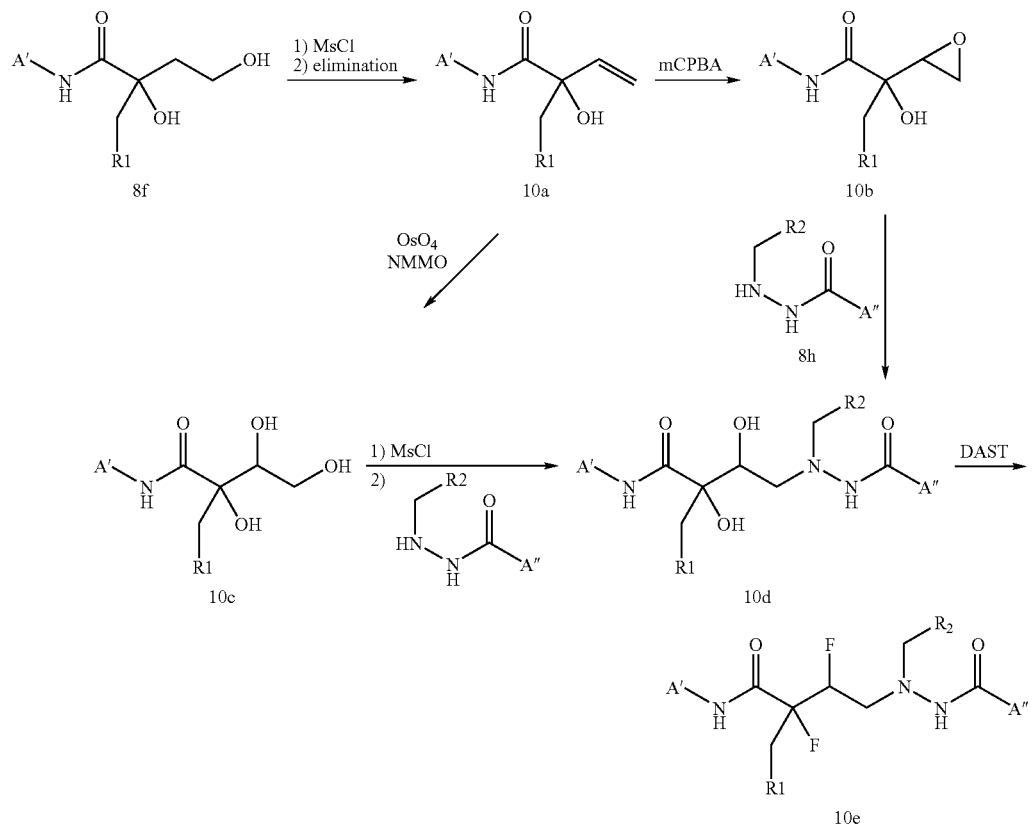

scheme 10

The olefine derivative (10a) can be achieved from the alcohol (8f), prepared as described in scheme 8, by transforming the primary alcohol to a leaving group such as a mesylate or the like followed by an elimination reaction brought about for example by treatment with a base such as t.BuOK or DBU in a solvent like DMSO, DMF or dichloromethane optionally in the presence of a crown ether. The afforded unsaturated compound (10a) can then be epoxidized by treatment with a suitable oxidizing reagent such as mCPBA or BuOOK or the like in a solvent like dichloromethane to give the epoxide (10b). Opening of the epoxide with a desired hydrazide derivative as described in scheme 1 then yields the diol (10d). Alternatively, a dihydroxylation of the double bond in the olefin (10a) can be performed for example by treatment with an oxidizing system such as $OsO_4$ and NMMO or the like which gives the triol (10c). Transformation of the primary alcohol into a leaving group as described above followed by a substitution reaction with the desired hydrazide derivative provides the dihydroxy hydrazide (10d). If desired, the two hydroxy groups can then be converted to fluorides by fluorination procedures known in the art for instance by using a fluorinating reagent such as DAST, Deoxofluor or the like as described by Rajendra et al. in Synthesis 17, 2002, p. 2561-2578, to give the difluorohydrazide (10e).

Compounds according to general formula I wherein n is 1, E is N, X is OH and L is F, $NH(C_1-C_3alkyl)$ or $N(C_1-C_3alkyl)_2$ can be prepared as exemplified in scheme 11.

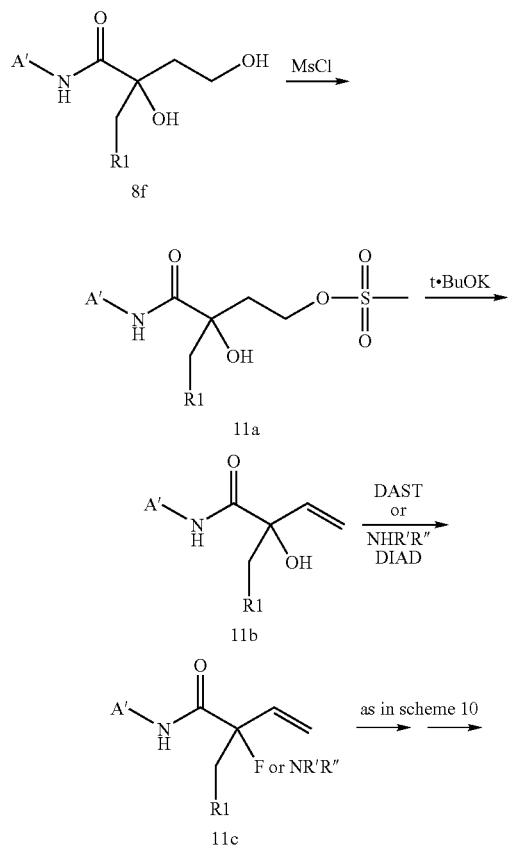

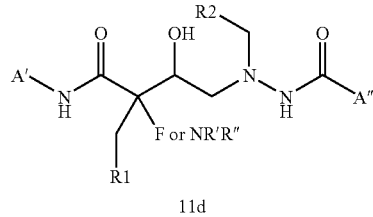

R′ is H or $C_1-C_3$alkyl
R″ is H or $C_1-C_3$alkyl

Transformation of the primary alcohol 8f, prepared as described in scheme 8, to a leaving group such as a derivative of sulphonic acid like a mesylate, triflate, tosylate or the like by treatment with the appropriate sulphonylating agent in a solvent like for instance pyridine or dichloromethane optionally in the presence of triethylamine or the like, followed by an elimination reaction brought about for instance by treatment with a base such as t.BuOK or DBU in a solvent like DMSO, DMF or dichloromethane optionally in the presence of a crown ether, or any other suitable elimination conditions. The hydroxy group of the afforded unsaturated compound (11b) can then be converted to a fluoride for example by reaction with a suitable fluorinating agent such as DAST or Deoxofluor or the like in a solvent like dichloromethane as described e.g. by Singh, R. P. and Shreve, J. M. in Synthesis, 17, 1999, p. 2561-2578, which yields the corresponding fluoro compound (11c). Alternatively, the hydroxy group of compound (11b) can be transferred to an amine using any convenient method described in the literature. For example the Mitsunobu procedure can be used, i.e. reaction of the alcohol (11b) with an azodicarboxylate such as DIAD or the like in the presence of triphenylphosphine followed by displacement with a desired amine which provides the corresponding amino derivative (11c). An alternative route to the amine (11c) is by transformation of the hydroxy group into a leaving group such as a derivative of sulphonic acid like a mesylate, triflate, tosylate or the like by treatment with the appropriate sulphonylating agent in a solvent like for instance pyridine or dichloromethane optionally in the presence of triethylamine or the like, followed by displacement of the leaving group with a desired primary or secondary amine $NH_2C_1-C_3alkyl$ or $NH(C_1-C_3alkyl)_2$. Alternatively, the leaving group can be displaced with azide, or the hydroxy group can be converted directly to an azide by use of an azide transfer agent like diphenyl phosphoryl azide (DPPA), subsequent reduction of the introduced azide to an amine, by for example triphenylphosphine optionally in the presence of a base like triethylamine provides compounds wherein L is $NH_2$ whereas a reductive amination of the afforded amine with a desired aldehyde or ketone provides secondary or tertiary amines.

Further treatment of the olefinic compound (11c) as described for compound 10a in scheme 10, i.e. either epoxidation of the double bond followed by reaction with the desired hydrazide derivative or dihydroxylation of the double bond followed by mesylation, substitution and finally reaction with the desired hydrazide derivative, provides the hydrazide derivative (11d). If desired, the hydroxy group of compound 11d can be converted to a fluoride by treatment with DAST or the like, as previously described thus providing compounds according to general formula I wherein X is F.

A route to compounds according to general formula I wherein n is 1, E is N, X is F and L is OH, F, NH(C$_1$-C$_3$alkyl) or N(C$_1$-C$_3$alkyl)$_2$ is illustrated in scheme 12.

Compounds according to general formula I wherein L is F, X is C$_1$-C$_3$alkyl, n is 1 and E is N can be prepared as illustrated in scheme 13.

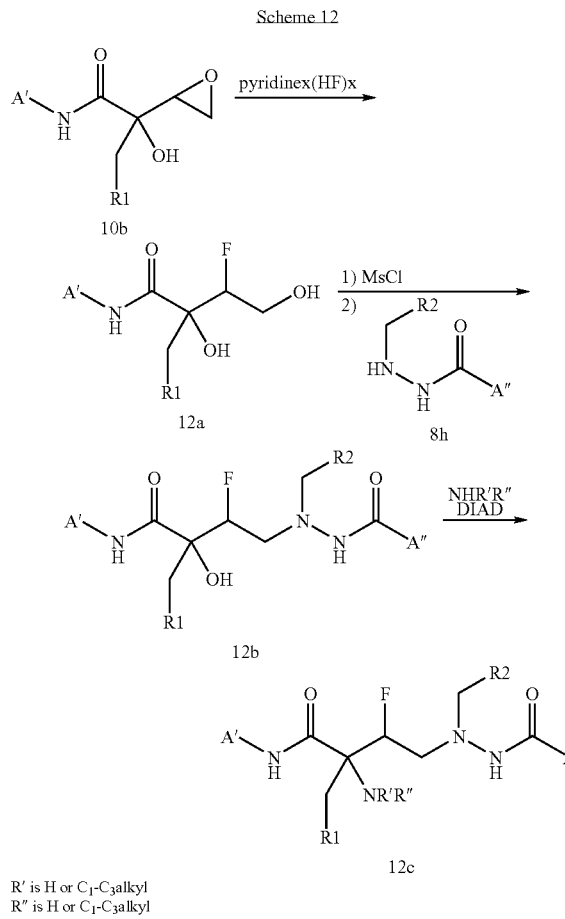

R' is H or C$_1$-C$_3$alkyl
R" is H or C$_1$-C$_3$alkyl

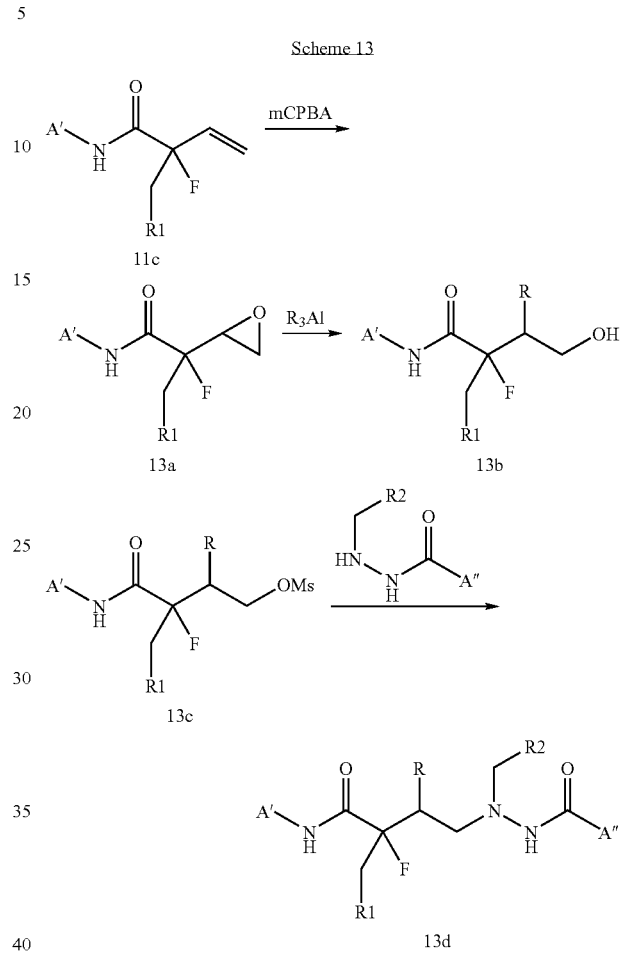

Opening of the epoxide (10b) by use of a fluorinating agent such as (HF)$_x$/pyridine as described i.a. by Baklouti, A. et al. in Synthesis 1999, p. 85-89, or (i-PrO)$_2$TiF$_2$-ET$_4$NF-nHF as described by Hara, S. et al. in Tetrahedron 55, 1999, p. 4947-4954 or any other suitable fluorinating agent provides the fluorohydrine (12a). Transformation of the primary hydroxy group into a leaving group such as a derivative of sulphonic acid like a mesylate, triflate, tosylate or the like by treatment with the appropriate sulphonylating agent in a solvent like for instance pyridine or dichloromethane optionally in the presence of triethylamine or the like, followed by reaction with a desired hydrazide derivative then gives the hydrazide (12b). If desired, the hydroxy group of the hydrazide (12b) can be converted to a fluoride by treatment with DAST or the like thus providing compounds according to general formula I wherein L is F, or the hydroxy group can be converted to an amine for example by way of a Mitsunobu reaction by treatment with the desired amine in the presence of DIAD or the like or by transformation of the hydroxy group to an azide followed by reduction of the azide to an amine, thus providing compound according to general formula I wherein L is NH$_2$ or the afforded amine can be reacted in a reductive amination with a desired aldehyde or ketone as previously described, thus providing compounds according to general formula I wherein L a substituted amine.

Epoxidation of the olefinic compound (11c), prepared as described in scheme 11, by reaction with a suitable oxidizing agent such as mCPBA or t.BuOOK or the like in a solvent like dichloromethane provides epoxide (13a). The alkylated compound (13b) can the be achieved by regioselective opening of the epoxide effected for example by using an aluminium reagent such as (alkyl)$_2$AlOAlalkyl or (alkyl)$_3$Al in the presence of water in a solvent like dichloromethane as described i.a. by Maruoka, K. et al. in Tetrahedron Lett., 40, 1999, p. 5369-5372 or by using an alkyltitanium reagent as described by Tanaka, T. et al. in Tetrahedron Lett. 45, 2004, p. 75-78. Conversion of the formed primary alcohol to a leaving group such as a halide like chlorine, bromine or iodine or to a derivative of sulphonic acid such as a mesylate, triflate, tosylate or the like by treatment with the appropriate sulphonylating agent in a solvent like for instance pyridine or dichloromethane optionally in the presence of triethylamine or the like, followed by reaction with a desired hydrazide derivative optionally in the presence of a base like Et$_3$N, t.BuOK or the like then gives the hydrazide (13d).

The synthesis of hydrazides (8 h) are described in the literature, se for example J. Med. Chem. 1998, 41, p. 3387, a general example thereof is shown in scheme 14.

Scheme 14

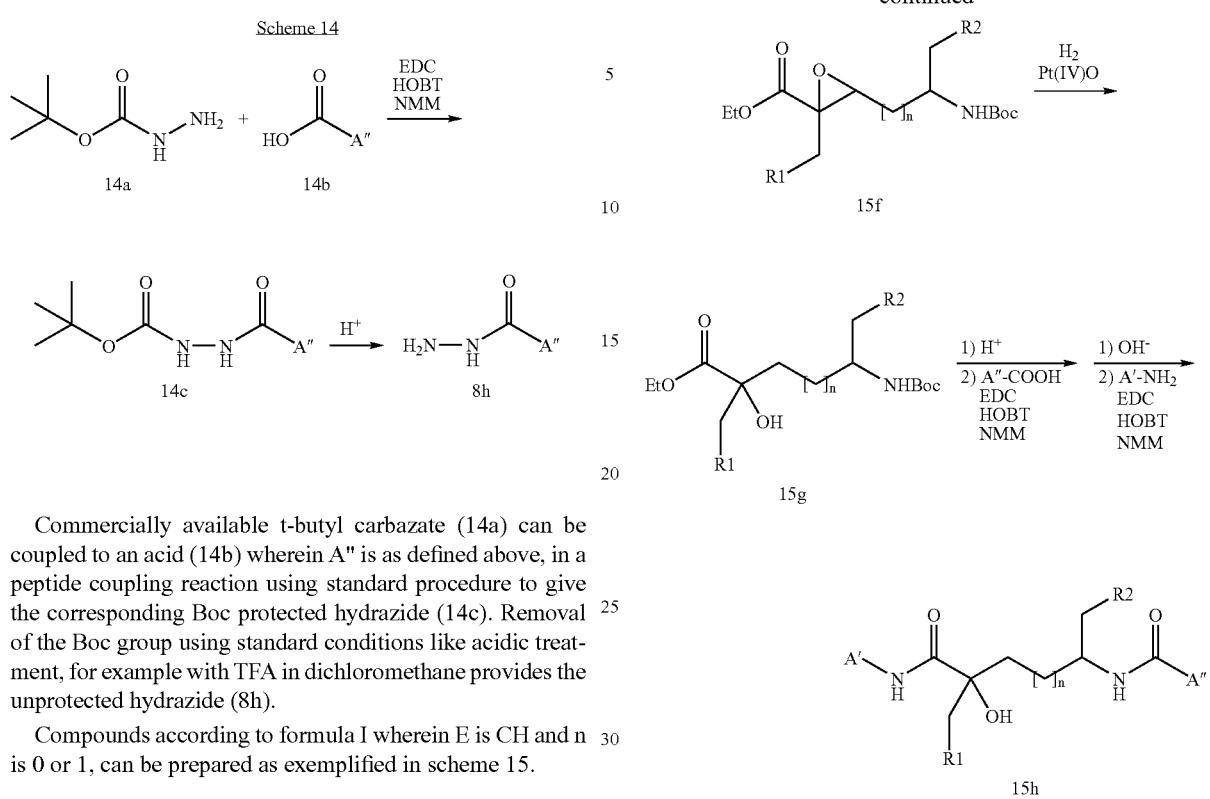

Commercially available t-butyl carbazate (14a) can be coupled to an acid (14b) wherein A″ is as defined above, in a peptide coupling reaction using standard procedure to give the corresponding Boc protected hydrazide (14c). Removal of the Boc group using standard conditions like acidic treatment, for example with TFA in dichloromethane provides the unprotected hydrazide (8h).

Compounds according to formula I wherein E is CH and n is 0 or 1, can be prepared as exemplified in scheme 15.

Scheme 15

The aldehyde (15b) can be prepared by subjecting a desired amino acid or homo amino acid derivative (15a) to N,O-dimethylhydroxylamine under peptide coupling conditions such as in the presences of EDAC, HOBT, triethylamine or the like, followed by reduction of the formed Weinreb amide with a reducing agent like LiAlH$_4$. Coupling of the formed aldehyde with a phosphonate (15c) in a Horner-Emmons reaction as described for example by A. Nadine et al. in Bioorg. Med. Chem. Lett., 2003, 13, 37-41, provides alkene (15e). The double bond can then be epoxidized using for instance mCPBA and the formed epoxide (15f) opened reductively by hydrogenation in the presence of a catalyst like Pt(IV)O as described in scheme 8. Subsequent coupling of the remaining fragments, A″ and A′ defined as for general formula I, using standard peptide coupling methods, i.e. removal of the boc group, coupling of the acid A″COOH followed by hydrolysis of the ester group and coupling of the amine A′-NH$_2$ yields the amide (15h). Compounds wherein A″ is according to formula (VI) are conveniently prepared by reacting the N-unprotected derivative of (15g) with an activated carbonate or chloroformate of the desired derivative, prepared as described in scheme 4, instead of with the acid A″-COOH.

The hydroxy group of compound (15h) can be converted to a fluoride or a primary or secondary amine thus providing compounds according to general formula I wherein X is H, E is CH and L is F, NHC$_1$-C$_3$alkyl or N(C$_1$-C$_3$alkyl)$_2$, as shown in scheme 16 below.

Scheme 16

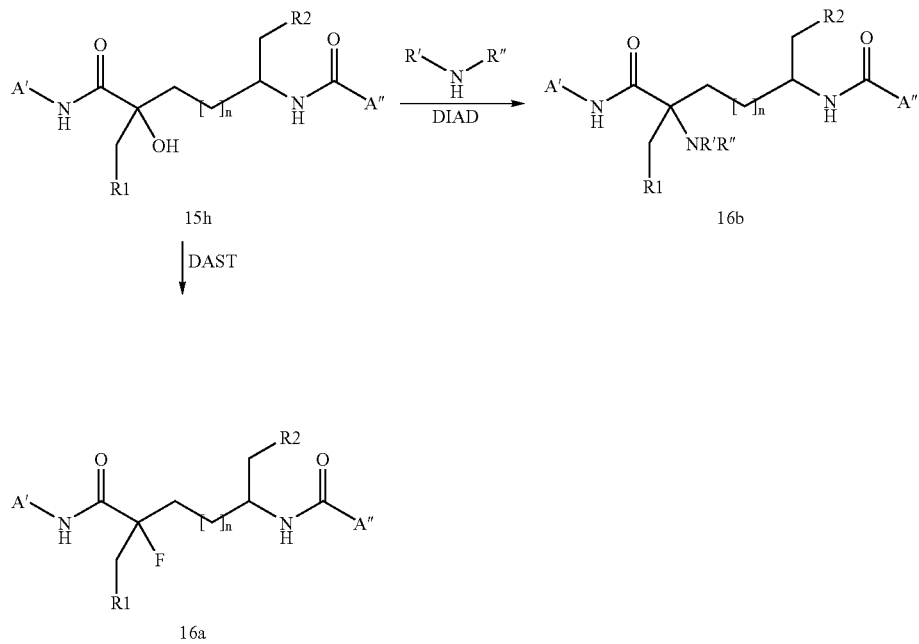

R′ is H or $C_1$-$C_3$alkyl
R″ is H or $C_1$-$C_3$alkyl
n is 0 or 1

Reaction of alcohol (15h) with a suitable fluorinating agent such as DAST or Deoxofluor or the like in a solvent like dichloromethane as described e.g. by Singh, R. P. and Shreve, J. M. in Synthesis, 17, 1999, p. 2561-2578, yields the corresponding fluoro compound (16a). Alternatively, the hydroxy group of compound 15h can be transferred to an amine using any convenient method described in the literature. For example the Mitsunobu procedure can be used, i.e. reaction of the alcohol (15h) with an azodicarboxylate such as DIAD or the like in the presence of triphenylphosphine followed by displacement with a desired amine which provides the corresponding amino derivative (16b). An alternative route to the amine (16b) is by transformation of the hydroxy group into a leaving group such as a derivative of sulphonic acid like a mesylate, triflate, tosylate or the like by treatment with the appropriate sulphonylating agent in a solvent like for instance pyridine or dichloromethane optionally in the presence of triethylamine or the like, followed by displacement of the leaving group with a desired primary or secondary amine $NH_2C_1$-$C_3$alkyl or $NH(C_1$-$C_3$alkyl$)_2$. Alternatively, the leaving group can be displaced with azide, or the hydroxy group can be converted directly to an azide by use of an azide transfer agent like diphenyl phosphoryl azide (DPPA), subsequent reduction of the introduced azide to an amine, by for example triphenylphosphine optionally in the presence of a base like triethylamine provides compounds wherein L is $NH_2$ whereas a reductive amination of the afforded amine with a desired aldehyde or ketone provides secondary or tertiary amines.

Dihydroxylated or difluorinated compounds wherein E is CH and X=L=OH or F and n is 0 or 1 in general formula I can be prepared as depicted in scheme 17.

Hydrolysis of the epoxide (15f) obtained from scheme 15 can be performed by using any convenient procedure known in the art, like for example subjection of the epoxide to acidic conditions such as treatment with a protic acid for example diluted perchloric acid, sulphuric acid or formic acid or with a Lewis acid such as BiCl$_3$ in a solvent like tetrahydrofuran or the like, which gives the diol (17a). Subsequent coupling of the acid A"-COOH and the amine A'-NH$_2$ as described in scheme 15 gives the dihydroxy amid (17b). If desired, the two hydroxy groups can then be converted to fluorides by using a fluorinating reagent such as DAST, Deoxofluor or the like to give the difluorohydrazide (17c).

A route to compounds according to general formula I wherein E is CH, X is OH, L is F and n is 0 or 1 is illustrated in scheme 18.

Compounds according to general formula I wherein E is CH, L is OH, F, NHC$_1$-C$_3$alkyl or N(C$_1$-C$_3$alkyl)$_2$, X is C$_1$-C$_3$alkyl and n is 0 or 1 can be prepared as illustrated in scheme 19.

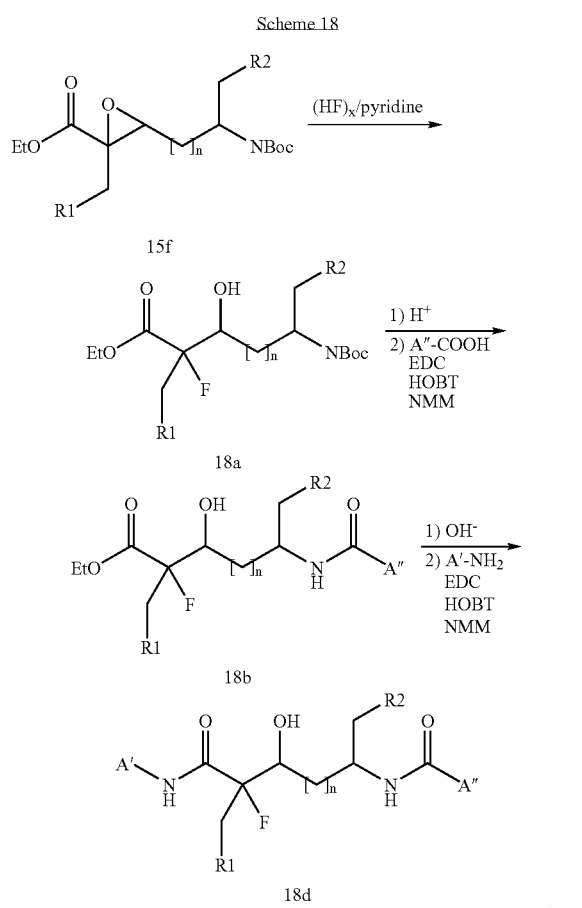

Opening of the epoxide (15f) by use of a fluorinating agent such as (HF)$_x$/pyridine as described i.a. by Baklouti, A. et al. in Synthesis 1999, p. 85-89 or (i-PrO)$_2$TiF$_2$-ET$_4$NF-nHF as described by Hara, S. et al. in Tetrahedron 55, 1999, p. 4947-4954 or any other suitable fluorinating agent provides the fluorohydrine (18a). Subsequent coupling, in any suitable order, of the acid A"-COOH and the amine A'-NH$_2$ as described in scheme 7 gives the fluorohydrine (18d). If desired, the hydroxy group of any of compounds 18a, 18b or 18c can be converted to a fluoride by treatment with DAST or the like, as previously described, thus providing an alternative route to compounds according to general formula I wherein X and L are F.

Alkylation of the epoxide (15f) prepared ad described in scheme 15, using an organocopper reagent such as a lithium dialkylcuprate in a solvent like diethyl ether or THF or the like provides the alkylated compound (19a). Coupling of the acid A"-COOH and the amine A'-NH$_2$, in any suitable order, as described in scheme 15 then gives the hydrazide derivative (19b). If desired, the hydroxy group of compound 19b can be converted to a fluoride by treatment with DAST or the like thus providing compounds according to general formula I wherein L is F, or the hydroxy group can be converted to an amine for example by way of a Mitsunobu reaction by treatment with the desired amine in the presence of DIAD or the like or by transformation of the hydroxy group to an azide followed by reduction of the azide to an amine, thus providing compounds according to general formula I wherein L is NH$_2$ or the afforded amine can be reacted in a reductive amination with a desired aldehyde or ketone as previously described, thus providing compounds according to general formula I wherein L a substituted amine.

An alternative route to compounds wherein E is CH and n is 1 is shown in scheme 20.

Scheme 20

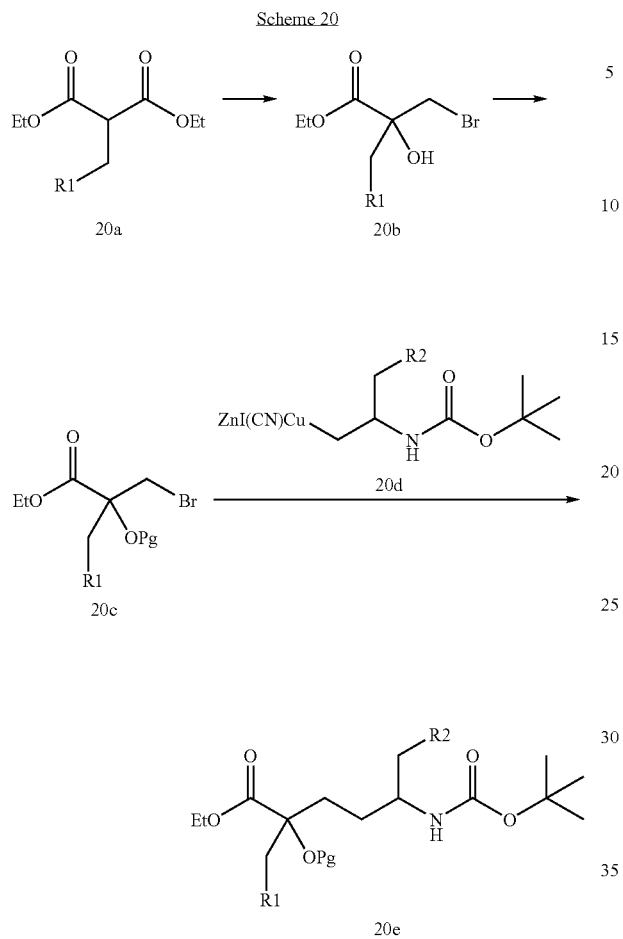

Scheme 21

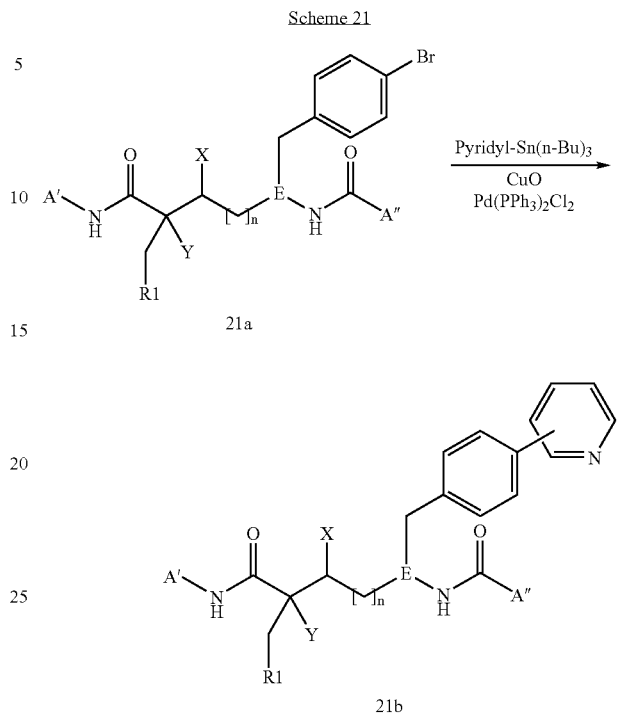

The aryl group of compound (21a) can be substituted with for example an aryl or heteroaryl group such as a pyridyl group by reacting the tri-n-butyltin derivative of the desired substituent in a coupling reaction using a palladium(0) reagent such as $Pd(PPh_3)_2Cl_2$ or the like in the presence of CuO in a solvent like dimethylformamide at an elevated temperature effected for instance by heating with microwaves.

It should be recognized that the strategy described in scheme 21 is not restricted only to pyridyl groups but is also applicable to other, optionally substituted, alkyl, aryl or heteroaryl groups. It should also be recognized that other methods, many of which are extensively described in the literature, may be used for the substitution of the $R^2$-group.

A general route to compounds according to formula I wherein n is 2 and E is N is shown in scheme 22.

Bromoderivative (20b) can be prepared from a suitable alkylated malonate derivative (20a), by a hydrolysation-reduction procedure followed by transformation of the formed primary alcohol to a bromide as described by Jew et al. in Heterocycles, 46, 1997, p. 65-70. Alkylated malonate derivatives are available either commercially or by alkylation of diethyl malonate with a desired alkylating agent according to literature procedures well known by the skilled person. The tertiary alcohol of the afforded bromoderivative (20b) can optionally be protected for instance as an acetate effected by treatment with acetic anhydride in pyridine or the like and subsequently coupled to a copper-zinc reagent (20d) prepared from a natural or non-natural amino acid, as described by Dudu et al. in Tetrahedron 50, 1994, p. 2415-2432 to give (20e). The remaining fragments, A" and A' defined as for general formula I, can then be introduced as described in scheme 15.

Substitution of the $R^2$ group of any of the above described compounds with a desired group using any suitable method known from the literature can be performed at any convenient stage of the synthesis. A method wherein a heteroaryl group is added to an aryl group is exemplified in scheme 21.

Scheme 22

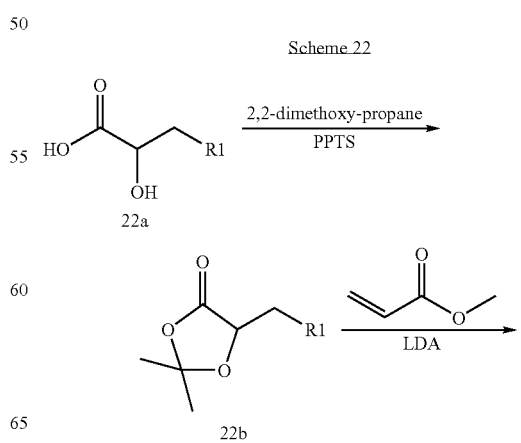

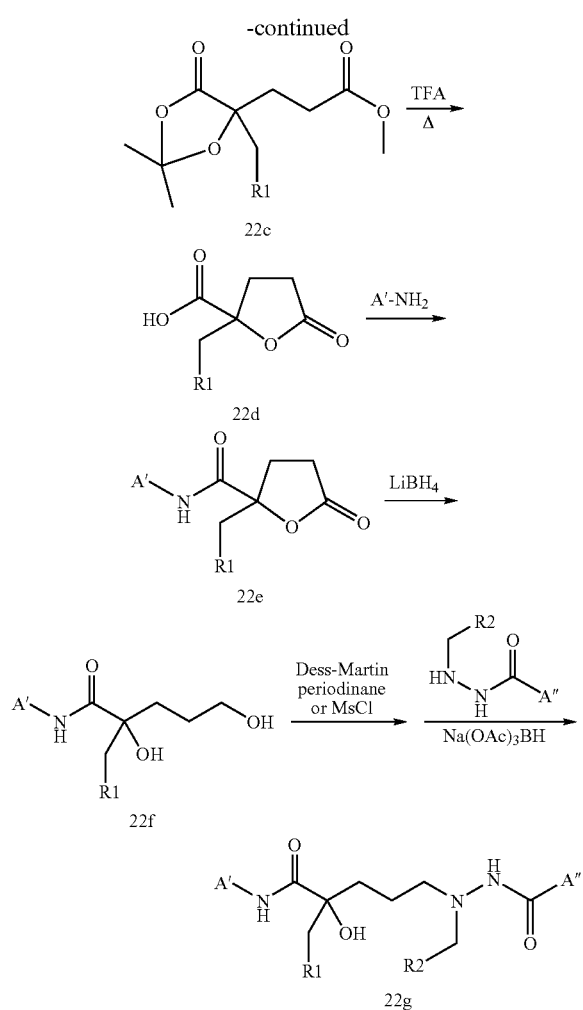

The two hydroxy groups of a desired 3-substituted 2-hydroxypropionic acid (22a) can be protected as a cyclic acetal by reacting the acid with a suitable acetalisation reagent such as 2,2-dimethoxypropane or 2-methoxypropene under acidic conditions achieved for example by the presence of a catalytic amount of pyridinium tosylate (PPTS), pTS, CSA or the like, which gives the cyclic acetal (22b). A subsequent Michael addition of methyl acrylate to the afforded acetal in the presence of a base such as LDA or the like then gives the α-alkylated compound (22c). Hydrolysation of the acetal and ring closure of the afforded intermediate alcohol, effected by treatment with an acid such as TFA at an elevated temperature gives the lactone (22d). Coupling of the amine A'-NH$_2$ using standard peptide coupling conditions, such as using reagents like EDAC, HOBt and optionally a base such as triethylamine or the like and subsequent reductive opening of the lactone using a reducing agent such as LiBH$_4$ or the like provides the diol (22f). The hydrazide derivative (22g) can then be achieved by using any of the methods previously described. For example the oxidation-reductive amination sequence described i.a. in scheme 8 can be used, i.e. the primary hydroxy group is oxidised to an aldehyde using any convenient oxidising agent like for instance Dess-Martin periodinane, followed by a reductive amination reaction with the desired hydrazide derivative in the presence of a suitable reducing agent like Na(OAc)$_3$BH or the like. Alternatively, the hydrazide moiety can be introduced by a displacement reaction as described i.a. in scheme 10, i.e. the primary alcohol is transferred to a leaving group such as a mesylate or the like whereafter the leaving group is displaced by the desired hydrazide derivative. If desired, the hydroxy substituent of hydrazide (22g) can be converted to an amine or a fluoro substituent using any of the previously described strategies thus providing compounds according to general formula (I) wherein L is F, NH$_2$, NHC$_1$-C$_6$alkyl or N(C$_1$-C$_6$alkyl)$_2$, X is H, n is 2 and E is N.

As will be appreciated by a person skilled in the field of organic synthesis, the synthetic steps in the preparation of compounds according to formula I can be performed in another order where appropriate. For example, the substituent —CH$_2$—R$^2$ of the hydrazide nitrogen of compounds wherein E is N, can be introduced by using a substituted hydrazide derivative as illustrated in scheme 1, or alternatively an unsubstituted or optionally temporarily N-protected hydrazide derivative can be used and the N-substituent introduced afterwards as illustrated in scheme 8. It should also be realized that the introduction of the amino and acid derivatives e.g. in scheme 18 and 19 can be performed in the reversed order, i.e. the acid A"-COOH is coupled prior to the amine A'-NH$_2$.

Any functional groups present on any of the constituent compounds used in the preparation of the compounds of the invention are appropriately protected where necessary. For example functionalities on the natural or non-natural amino acids are typically protected as is appropriate in peptide synthesis. Those skilled in the art will appreciate that the selection and use of appropriate protecting groups depend upon the reaction conditions. Suitable protecting groups are described in Greene, "Protective Groups in Organic Synthesis", John Wiley & Sons, New York (1981) and "The Peptides: Analysis, Synthesis, Biology", Vol. 3, Academic Press, New York (1981), the disclosure of which are hereby incorporated by reference.

DETAILED DESCRIPTION

Various embodiments of the compounds of the invention and key intermediates towards such compounds will now be described by way of illustration only with reference to the accompanying non-limiting chemistry and biology examples.

Chemistry. General Information. Analytical RP-LC-MS was performed on a Gilson HPLC system with a Finnigan AQA quadropole mass spectrometer using a Chromolith Performance RP-18e 4.6×100 mm (Merck KGaA) column, with MeCN in 0.05% aqueous HCOOH as mobile phase at a flow rate of 4 mL/min. Preparative RP-LC-MS was performed on a Gilson HPLC system with a Finnigan AQA quadropole mass spectrometer using a Zorbax SB-C8, 5 µm 21.2×150 mm (Agilent technologies) column, with MeCN in 0.05% aqueous HCOOH as mobile phase at a flow rate of 15 mL/min. Optical rotations were obtained on a Perkin-Elmer 241 polarimeter, specific rotations ([α]D) are reported in deg/dm and the concentration (c) is given in g/100 mL in the specified solvent. $^1$H and $^{13}$C NMR spectra were recorded on Varian Mercury Plus instruments at 300 and 75.45 MHz or 399.78 and 100.53 MHz respectively. Chemical shifts are reported as δ values (ppm) indirectly referenced to TMS via the solvent residual signal. Flash column chromatography was performed on Merck silica gel 60 (40-63 µm) or Merck silica gel 60 RP-18 (40-63 µm). Analytical thin layer chromatography was done using aluminum sheets precoated with silica gel 60 F$_{254}$. UV light and an ethanolic solution of

Example 1

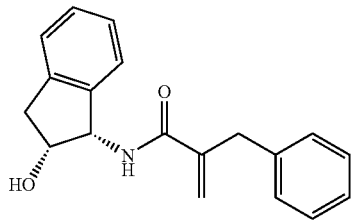

2-Benzyl-N-[(1S,2R)-2-hydroxy-indan-1-yl]-acryl amide (1)

2-Benzyl acrylic acid (J. Organomet., Chem. 646, 212-222, 2002) (2.72 g, 16.8 mmol) was dissolved in EtOAc (50 mL) and EDAC (3.54 g, 18.5 mmol), HOBT (2.49 g, 18.4 mmol) and NMM (2.21 mL, 20.1 mmol) were added. The reaction mixture was stirred at room temperature for 30 min and then (1S,2R)-1-amino-2-indanol (2.75 g, 18.4 mmol) was added and the stirring was continued over night. Washing with saturated NaHCO$_3$ (aq.) and brine followed by drying (Na$_2$SO$_4$) and evaporation of the organic solvent afforded the crude product, which were subjected to column chromatography (silica, EtOAc/pentane, 40:60-50:50) yielding 2 (3.34 g, 68%) as a white solid.

$[\alpha]_D^{22}$+23.9° (c 0.77, MeOH); $^1$H NMR (CDCl$_3$) δ 7.40-7.11 (m, 8H), 6.97 (m, 1H), 6.42 (d, J=8.27 Hz, 1H), 5.87 (s, 1H), 5.35 (m, 2H), 4.55 (m, 1H), 3.77 (d, J=15.6 Hz, 1H), 3.70 (d, J=15.6 Hz, 1H), 3.14 (dd, J=5.21, 16.6 Hz, 1H), 2.89 (dd, J=1.89, 16.6 Hz, 1H), 2.18 (d, J=4.90 Hz, 1H); $^{13}$C NMR (CDCl$_3$) δ 168.9, 144.3, 140.7, 140.1, 138.5, 129.2, 128.9, 128.4, 127.4, 126.9, 125.5, 124.6, 120.5, 73.7, 57.9, 40.0, 39.2. MS (m/z 294, M+H$^+$, 587); Anal. (C$_{19}$H$_{19}$NO$_2$) C, H, N.

Example 2

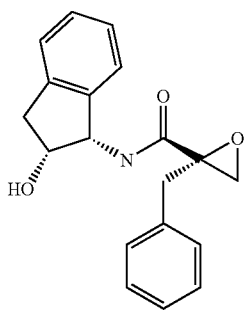

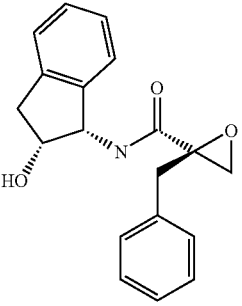

(2S)-2-Benzyl-oxirane-N-[(1S,2R)-2-hydroxy-indan-1-yl]-2-carboxylic acid amide((S)-3) (2a) and (2R)-2-Benzyl-oxirane-N-[(1S,2R)-2-hydroxy-indan-1-yl]-2-carboxylic acid amide((R)-3) (2b)

Compound 1 (1.57 g, 5.36 mmol) was dissolved in CH$_2$Cl$_2$ (30 mL) and mCPBA (77%, 2.40 g, 10.7 mmol) was added. The reaction mixture was heated to reflux for 48 h, cooled and washed with 10% Na$_2$S$_2$O$_3$ (aq.), saturated NaHCO$_3$ (aq.) and brine. The organic phase was dried (Na$_2$SO$_4$), filtered and evaporated, and then the crude product was purified by column chromatography (silica, EtOAc/pentane, 40:60-100:0) yielding the two diastereomeric epoxides; 2a (0.414 g) as a pale yellow solid and 2b (0.460 g) as a white solid in a total yield of 53%.

2a: R$_f$=0.58 (EtOAc/pentane 50:50); $[\alpha]_D^{19}$−60.1° (c 1.00, CHCl$_3$); $^1$H NMR (CD$_3$OD) δ 7.35-7.11 (m, 8H), 7.07 (m, 1H), 5.18 (d, J=5.12 Hz, 1H), 4.42 (ddd, J=1.50, 4.97, 5.12 Hz, 1H), 3.63 (d, J=14.8 Hz, 1H), 3.11 (dd, J=4.97, 16.5, 1H), 2.97 (d, J=14.8 Hz, 1H), 2.91 (d, J=4.99 Hz, 1H), 2.87 (dd, J=1.50, 16.5, 1H), 2.85 (d, J=4.99 Hz, 1H); $^{13}$C NMR (CDCl$_3$) δ 170.4, 140.4, 140.0, 136.0, 130.1, 128.7, 128.6, 127.38, 127.39, 125.6, 124.2, 73.4, 60.4, 57.5, 53.0, 39.6, 37.2; MS (m/z 310, M+H$^+$, 619); Anal. (C$_{19}$H$_{19}$NO$_3$) C, H, N.

2b R$_f$=0.13 (EtOAc/pentane 50:50); $[\alpha]_D^{19}$+73.3° (c 1.00, CHCl$_3$);

$^1$H NMR (CD$_3$OD/CDCl$_3$ 1:1+2 drops of D$_2$O) δ 7.37-7.08 (m, 7H), 6.98 (m, 1H), 6.41 (m, 1H), 5.16 (ddd, J=1.14, 5.04, 9.23 Hz, 1H), 4.43 (ddd, J=1.33, 4.97, 5.04 Hz, 1H), 3.73 (d, J=14.5 Hz, 1H), 3.07 (m, 1H), 3.00 (d, J=5.09 Hz, 1H), 2.93 (d, J=5.09 Hz, 1H), 2.84 (m, 1H), 2.75 (d, J=14.5 Hz, 1H); $^{13}$C NMR (CD$_3$OD/CDCl$_3$ 1:1+2 drops of D$_2$O) δ 171.3, 141.1, 140.6, 136.7, 130.5, 129.0, 128.5, 127.6, 127.5, 125.6, 124.7, 73.3, 60.8, 57.4, 53.4, 40.5, 37.8; MS (m/z 310, M+H$^+$, 619); Anal. (C$_{19}$H$_{19}$NO$_3$) C, H, N.

General Procedure for the Preparation of Hydrazides

Benzylhydrazine×2HCl and Et$_3$N in EtOAc (20 mL) were allowed to stir for 30 min at room temperature and then added to a solution of N-functionalised amino acid (below), EDAC, HOBT and NMM in EtOAc (40 mL) after which the reaction mixture was allowed to stir overnight at room temperature. Dilution with EtOAc, washing with saturated NaHCO$_3$ (aq.), H$_2$O and brine followed by drying (Na$_2$SO$_4$), filtration and concentration of the organic phase under vacuum afforded the crude product which was purified by column chromatography (silica, CHCl$_3$/MeOH, 100:0-95:5).

Example 3

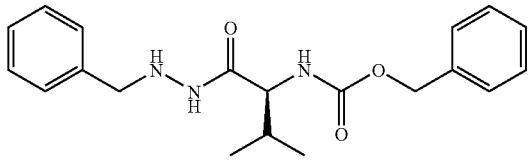

[(1S)-1-(N'-Benzyl-hydrazinocarbonyl)-2-methyl-propyl]-carbamic acid benzyl ester (3)

The general procedure for the preparation of hydrazides described above was followed using Cbz-(L)-valine (0.540 g, 2.15 mmol), EDAC (0.450 g, 2.35 mmol), HOBT (0.320 g, 2.37 mmol), NMM (0.260 mL, 2.36 mmol), benzylhydrazine×2HCl (0.500 g, 2.56 mmol) and Et$_3$N (0.710 mL, 5.09 mmol) which gave the title compound (0.502 g, 66%) as a white solid.

$[\alpha]_D^{21}$ −41.7° (c 0.35, MeOH/CH$_2$Cl$_2$ 50:50); $^1$H NMR (DMSO-d$_6$ +2 drops of D$_2$O) δ 7.42-7.18 (m, 10H), 5.01 (s, 2H), 3.82 (s, 2H), 3.72 (d, J=7.61, 1H), 1.83 (m, 1H), 0.78 (d, J=6.86, 3H), 0.76 (d, J=6.86, 3H); $^{13}$C NMR (DMSO-d$_6$+2 drops of D$_2$O) δ 170.8, 156.7, 139.2, 137.7, 129.1, 129.0, 128.8, 128.5, 128.3, 127.6, 66.1, 59.5, 55.0, 30.9, 19.7, 19.0; MS (m/z 356, M+H$^+$); Anal. (C$_{20}$H$_{25}$N$_3$O$_3$) C, H, N.

Example 4

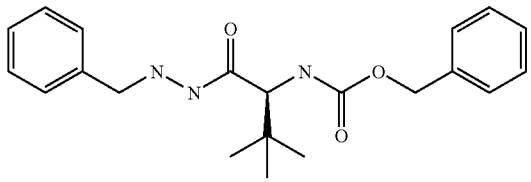

[(1S)-1-(N'-Benzyl-hydrazinocarbonyl)-2,2-dimethyl-propyl]-carbamic acid benzyl ester (4)

The general procedure for the preparation of hydrazides described above was followed using Cbz-(L)-tert-leucine (2.00 g, 4.48 mmol), EDAC (0.969 g, 5.05 mmol), HOBT (0.669 g, 4.95 mmol), NMM (0.542 mL, 4.93 mmol), benzylhydrazine×2HCl (0.962 g, 4.93 mmol) and Et$_3$N (1.38 mL, 9.85 mmol) which gave the title compound (1.11 g, 67%) as a low melting solid.

$[\alpha]_D^{19}$ −17.5° (c 1.0, CHCl$_3$); $^1$H NMR (CD$_3$OD) δ 7.38-7.15 (m, 10H), 5.05 (d, J=12.3 Hz, 1H), 4.99 (d, J=12.3 Hz, 1H), 3.99 (s, 1H), 3.90 (s, 2H), 0.92 (s, 9H); $^{13}$C NMR (CD$_3$OD) δ 171.3, 158.0, 138.6, 137.9, 129.8, 129.3, 129.2, 128.9, 128.7, 128.3, 67.6, 62.5, 56.2, 35.2, 27.0; MS (m/z 370, M+H$^+$); Anal. (C$_{21}$H$_{27}$N$_3$O$_3$) C, H, N.

Example 5

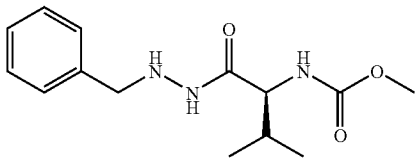

[(1S)-1-(N'-Benzyl-hydrazinocarbonyl)-2-methyl-propyl]-carbamic acid methyl ester (5)

The general procedure for the preparation of hydrazides described above was followed using N-(methoxycarbonyl)-(L)-valine (J. Med. Chem., 39, 3203-3216, 1996) (2.11 g, 12.0 mmol), EDAC (2.41 g, 12.6 mmol), HOBT (1.70 g, 12.6 mmol), NMM (1.38 mL, 12.6 mmol), benzylhydrazine× 2HCl (2.45 g, 12.6 mmol) and Et$_3$N (3.52 mL, 25.0 mmol), which gave the title compound (2.08 g, 65%) as a light yellow solid.

$[\alpha]_D^{19}$ −45.5° (c 1.0, CHCl$_3$); $^1$H NMR (CDCl$_3$) δ 8.00 (s, 1H) 7.40-7.25 (m, 5H), 5.50 (d, J=9.04 Hz, 1H), 4.85 (s, 1H), 3.96 (s, 2H), 3.89 (dd, J=7.04, 9.04, 1H), 3.64 (s, 3H), 2.05 (m, 1H), 0.94 (d, J=4.94 Hz, 3H), 0.92 (d, J=4.94 Hz, 3H); $^{13}$C NMR (CDCl$_3$) δ 171.2, 157.3, 137.5, 129.2, 128.7, 127.9, 59.4, 56.1, 52.6, 31.2, 19.4, 18.2; MS (m/z 280, M+H$^+$, 559); Anal. (C$_{14}$H$_{21}$N$_3$O$_3$) C, H, N.

Example 6

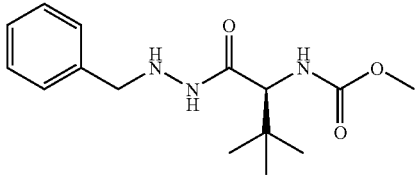

[(1S)-1-(N'-Benzyl-hydrazinocarbonyl)-2,2-dimethyl-propyl]-carbamic acid methyl ester (6)

The general procedure for the preparation of hydrazides described above was followed using N-(methoxycarbonyl)-(L)-tert-leucine (J. Med. Chem., 41, 3387-3401, 1998) (1.56 g, 8.24 mmol), EDAC (1.74 g, 9.08 mmol), HOBT (1.22 g, 9.03 mmol), NMM (0.995 mL, 9.05 mmol), benzylhydrazine×2HCl (1.61 g, 8.25 mmol) and Et$_3$N (2.53 mL, 18.0 mmol) which gave the title compound (1.21 g, 50%) as a light yellow solid.

$[\alpha]_D^{19}$ −40.7° (c 0.98, CHCl$_3$); $^1$H NMR (CDCl$_3$) δ 8.07 (s, 1H) 7.38-7.24 (m, 5H), 5.63 (d, J=9.64 Hz, 1H), 4.95 (s, 1H), 4.00 (d, J=12.4 Hz, 1H), 3.95 (d, J=12.4 Hz, 1H), 3.92 (d, J=9.64 Hz, 1H), 3.68 (s, 3H), 0.98 (s, 9H); $^{13}$C NMR (CDCl$_3$) δ170.2, 157.1, 137.3, 128.9, 128.4, 127.6, 61.1, 55.8, 52.3, 34.5, 26.4; MS (m/z 294, M+H$^+$); Anal. (C$_{15}$H$_{23}$N$_3$O$_3$) C, H, N.

Example 7

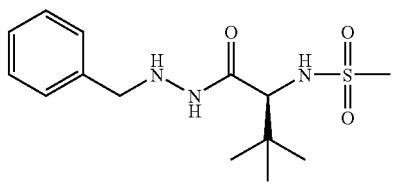

N-[(1S)-1-(N'-Benzyl-hydrazinocarbonyl)-2,2-dimethyl-propyl]-methane sulfonamide (7)

A solution of methanesulfonyl chloride (0.593 mL, 7.62 mmol) in 1M NaOH (7.60 mL, 15.2 mmol) and THF (10 mL) was added drop wise to a stirred mixture of (L)-tert-leucine (1.0 g, 7.6 mmol), dissolved in THF (7.6 mL) and $H_2O$ (12 mL) at 0° C. The reaction mixture was stirred at 0° C. for 3 h and then at room temperature overnight. The mixture was acidified with 4M HCl and extracted with EtOAc. The organic phase was separated, dried ($Na_2SO_4$), filtered and concentrated under reduced pressure to give (2S)-2-methanesulphonylamino-3,3-dimethyl-butyric acid (0.486 g, 30%), which was analyzed by NMR and then used without further purification. The general procedure for the preparation of hydrazides described above was then followed using the crude (2S)-2-methanesulfonylamino-3,3-dimethyl-butyric acid (0.476 g, 2.27 mmol), EDAC (0.481 g, 2.51 mmol), HOBT (0.338 g, 2.50 mmol), NMM (0.275 mL, 2.50 mmol), benzylhydrazine×2HCl (0.489 g, 2.51 mmol) and $Et_3N$ (0.700 mL, 4.98 mmol) which gave the title compound (0.416 g, 58%) as a white solid.

$[\alpha]_D^{21}$ +24.4° (c 1.02, $CHCl_3$); $^1H$ NMR ($CD_3OD$) δ 7.44-7.20 (m, 5H), 4.01 (d, J=13.1 Hz, 1H), 3.95 (d, J=13.1 Hz, 1H), 3.47 (s, 1H), 2.71 (s, 3H), 0.94 (s, 9H); $^{13}C$ NMR ($CD_3OD$) δ 171.1, 139.0, 129.9, 129.5, 128.5, 64.5, 56.1, 40.8, 35.3, 27.0; MS (m/z 314, M+H$^+$); Anal. ($C_{14}H_{23}N_3O_3S$) C, H, N.

Example 8

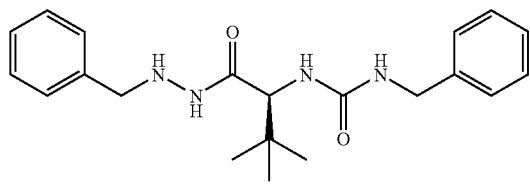

1-Benzyl-3-[(1S)-1-(N'-benzyl-hydrazinocarbonyl)-2,2-dimethyl-propyl]-urea (8)

(L)-tert-Leucine (0.500 g, 3.81 mmol) was dissolved in dioxane (23 mL) and 2M NaOH (6.3 mL, 12.6 mmol) was added. After stirring for 10 min, phenylisocyanate (0.900 mL, 7.29 mmol) was added drop wise to yield a clear solution. The reaction mixture was stirred at room temperature for 18 h and then made acidic by addition of concentrated HCl and thereafter extracted with EtOAc. The organic phase was dried and evaporated to afford (2S)-2-(3-benzyl-ureido)-3,3-dimethyl-butyric acid (0.36 g, 36% yield), which was analysed by NMR and then used without further purification. The general procedure for the preparation of hydrazides described above was then followed using the crude (2S)-2-(3-benzyl-ureido)-3,3-dimethyl-butyric acid (0.646 g, 2.44 mmol), EDAC (0.515 g, 2.67 mmol), HOBT (0.363 g, 2.69 mmol), NMM (0.300 mL, 2.73 mmol), benzylhydrazine×2HCl (0.528 g, 2.71 mmol) and $Et_3N$ (0.753 mL, 5.38 mmol). The product was filtered through a short silica column ($CHCl_3$/MeOH, 100:0-95:5) and then used without further purification in the next step.

Example 9

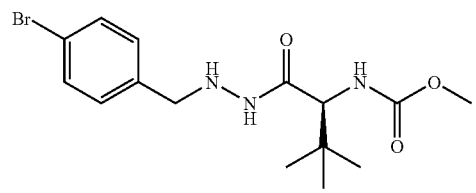

{(1S)-1-[N'-(4-Bromo-benzyl)-hydrazinocarbonyl]-2,2-dimethyl-propyl}-carbamic acid methyl ester (9)

N-(Methoxycarbonyl)-(L)-tert-leucine (J. Med. Chem., 41, 3387-3401, 1998) (1.74 g, 9.20 mmol) was dissolved in EtOAc (50 mL) and EDAC (1.94 g, 10.1 mmol), HOBT (1.37 g, 10.1 mmol), and NMM (1.11 mL, 10.1 mmol) were added. The reaction mixture was stirred at room temperature for 30 min and then 4-bromo-benzylhydrazine (prepared as described in Zh. Org. Khim., 28, 43-50, 1992) (2.31 g, 11.5 mmol) in EtOAc (20 mL) was added and the stirring was continued over night. The reaction mixture was washed with saturated $NaHCO_3$ (aq.), $H_2O$ and brine and then the organic phase was dried ($Na_2SO_4$), filtered and evaporated. The crude product was purified by column chromatography (silica, $CHCl_3$/MeOH, 100:0-96:4) yielding the title compound (1.85 g, 54%) as a white solid.

$[\alpha]_D^{22}$ −26.4° (c 0.84, MeOH); $^1H$ NMR ($CD_3OD$) δ 7.45 (m, 2H), 7.29 (m, 2H), 3.90 (s, 2H), 3.81 (s, 1H), 3.64 (s, 3H), 0.90 (s, 9H); $^{13}C$ NMR ($CD_3OD$) δ 170.5, 157.9, 137.2, 131.3, 130.8, 121.0, 61.7, 54.2, 51.5, 33.9, 25.8; MS (m/z 372, M+H$^+$, 374, M+H$^+$); Anal. ($C_{15}H_{22}BrN_3O_3$) C, H, N.

Example 10

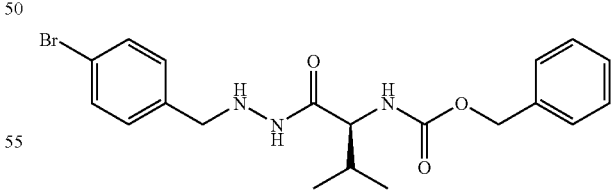

{(1S)-1-[N'-(4-Bromo-benzyl)-hydrazinocarbonyl]-2-methyl-propyl}-carbamic acid benzyl ester (10)

Cbz-(L)-Valine (1.04 g, 4.14 mmol) was dissolved in EtOAc (50 mL) and EDAC (0.870 g, 4.54 mmol), HOBT (0.610 g, 4.51 mmol), and NMM (0.500 mL, 4.55 mmol) were added. The reaction mixture was stirred at room temperature for 30 min and then 4-bromo-benzylhydrazine (1.00 g, 4.97 mmol) in EtOAc (5 mL) was added and the stirring was continued for 2 h. After evaporation of the solvent, CHCl₃ was added and the solution was washed with saturated NaHCO₃ (aq.) and brine followed by drying (Na₂SO₄), filtration and evaporation of the organic solvent. The crude product was purified by column chromatography (silica, CHCl₃/MeOH, 100:0-95:5) yielding the title compound (1.42 g, 79%) as a white solid.

$[\alpha]_D^{21}$ +6.2° (c 0.47, DMF); ¹H NMR (DMSO-d₆ +2 drops of D₂O) δ 7.53-7.18 (m, 9H), 4.98 (s, 2H), 3.79 (s, 2H), 3.69 (d, J=7.65 Hz, 1H), 1.80 (m, 1H), 0.75 (d, J=6.92 Hz, 3H), 0.72 (d, J=6.92 Hz, 3H); ¹³C NMR (DMSO-d₆ +2 drops of D₂O) δ 170.8, 156.6, 138.8, 137.7, 131.6, 131.4, 129.0, 128.5, 128.3, 120.6, 66.1, 59.5, 54.2, 30.8, 19.7, 19.0; MS (m/z 434, M+H⁺, 436, M+H⁺); Anal. (C₂₀H₂₄BrN₃O₃) C, H, N.

General Procedures for Synthesis of Inhibitors

Method A. Epoxide 2a or 2b and hydrazide were dissolved in iPrOH (6 mL) and the reaction mixture was stirred at 80° C. for the time indicated. Evaporation of the solvent afforded the crude product, which was subjected to purification as stated below.

Method B. Epoxide 2a or 2b and hydrazide was dissolved in dry THF (30 mL) and Ti(OiPr)₄ was added under N₂-atmosphere. Stirring in room temperature for 2.5 h and then at 40° C. for 30 min was followed by addition of saturated NaHCO₃ (aq.) and Et₂O and the resulting mixture was stirred in room temperature for 10 min. Filtration and separation of the two phases, drying of the organic phase (Na₂SO₄) and evaporation yielded the crude product which was purified by column chromatography (RP-silica, MeCN/H₂O, 50:50-90:10).

Example 11

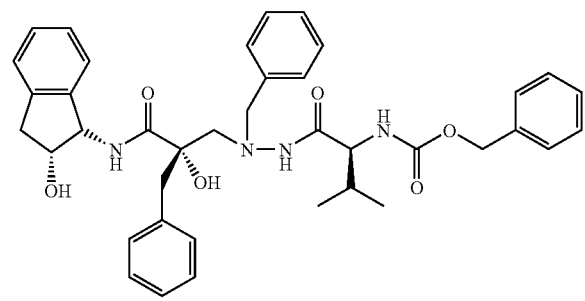

{(1S)-1-[N'-Benzyl-N'-((2S)-2-hydroxy-2-((1S,2R)-2-hydroxy-indan-1-ylcarbamoyl)-3-phenyl-propyl)-hydrazinocarbonyl]-2-methyl-propyl}-carbamic acid benzyl ester (11)

The title compound was prepared according to Method A by heating epoxide 2a (0.0950 g, 0.307 mmol) and hydrazide 3 (0.218 g, 0.614 mmol) for 90 h. Purification by column chromatography (silica, EtOAc/pentane 30:70-100:0) gave the product (0.112 g, 55%) as a white solid.

$[\alpha]_D^{19}$ −10.8° (c 0.94, DMF); ¹H NMR (CD₃OD) δ 7.38-6.97 (m, 18H), 6.81 (m, 1H), 5.04 (s, 2H), 4.99 (d, J=4.92 Hz, 1H), 4.20 (d, J=14.0 Hz, 1H), 4.11 (m, 1H), 4.02 (d, J=14.0 Hz, 1H), 3.87 (d, J=14.0 Hz, 1H), 3.61 (d, J=7.18 Hz, 1H), 3.08-2.76 (m, 5H), 1.61 (m, 1H), 0.60 (d, J=6.81 Hz, 3H), 0.46 (d, J=6.81, 3H); ¹³C NMR (CD₃OD) δ 177.5, 173.2, 158.4, 142.1, 141.4, 138.6, 138.2, 137.6, 131.6, 129.8, 129.5, 129.2, 129.0, 128.9, 128.8, 128.7, 128.4, 127.7, 127.6, 126.0, 125.6, 79.3, 73.9, 68.1, 67.7, 62.9, 60.8, 58.5, 44.5, 40.8, 31.7, 19.2, 18.4; MS (m/z 665, M+H⁺); Anal. (C₃₉H₄₄N₄O₆×0.25H₂O) C, H, N: calcd, 70.03, 6.71, 8.38; found, 69.98, 6.56, 8.15.

Example 12

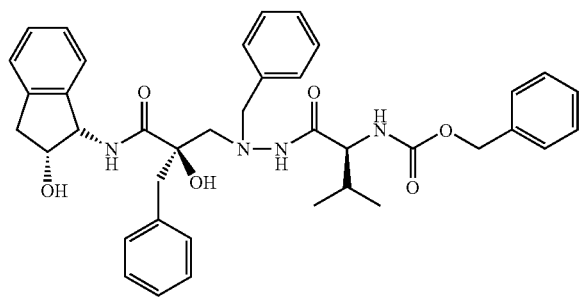

{(1S)-1-[N'-Benzyl-N'-((2R)-2-hydroxy-2-((1S,2R)-2-hydroxy-indan-1-ylcarbamoyl)-3-phenyl-propyl)-hydrazinocarbonyl]-2-methyl-propyl}-carbamic acid benzyl ester (12)

The title compound was prepared according to Method A by heating epoxide 2b (0.104 g, 0.336 mmol) and hydrazide 3 (0.240 g, 0.676 mmol) for 120 h. Purification of 0.170 g of the crude product by RP-LC-MS (30 min gradient of 20-80% CH₃CN in 0.05% aqueous formic acid) gave the product (44 mg, 39%) as a white solid.

$[\alpha]_D^{19}$ +10.8° (c 0.58, DMF);

¹H NMR (CD₃OD) δ 7.42-7.07 (m, 17H), 6.97 (m, 1H), 6.25 (m, 1H), 5.04 (d, J=5.22, 1H), 5.01 (s, 2H), 4.37 (m, 1H), 4.05 (s, 2H), 3.68 (m, 2H), 3.10-2.72 (m, 5H), 1.78 (m, 1H), 0.70 (d, J=6.74 Hz, 3H), 0.67 (d, J=6.74 Hz, 3H);

¹³C NMR (DMSO-d₆) δ 174.2, 171.1, 156.6, 142.7, 140.9, 138.5, 137.7, 137.4, 131.3, 129.2, 130.0, 128.6, 128.44, 128.39, 128.3, 127.7, 127.6, 126.8, 126.7, 125.3, 124.7, 78.4, 72.7, 72.6, 68.0, 66.1, 61.7, 59.5, 56.8, 43.3, 30.9, 19.5, 18.6;

MS (m/z 664, M+H⁺); Anal. (C₃₉H₄₄N₄O₆) C, H, N.

Example 13

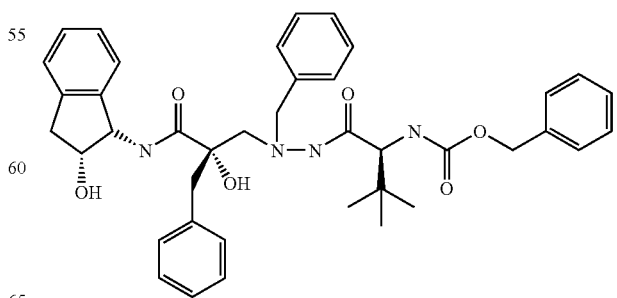

{(1S)-1-[N'-Benzyl-N'-((2S)-2-hydroxy-2-((1S,2R)-2-hydroxy-indan-1-ylcarbamoyl)-3-phenyl-propyl)-hydrazinocarbonyl]-2,2-dimethyl-propyl}-carbamic acid benzyl ester (13)

The title compound was prepared according to Method A, using epoxide 2a (0.0996 g, 0.322 mmol) and hydrazide 4 (0.143 g, 0.387 mmol) by heating for 96 h. Purification by column chromatography (silica, EtOAc/pentane, 40:60-100:0) followed by RP-LC-MS (30 min gradient of 20-100% CH$_3$CN in 0.05% aqueous HCOOH) gave the product (0.0880 g, 40%) as a white solid.

$[\alpha]_D^{19}$ −61.6° (c 1.01, CHCl$_3$); $^1$H NMR (CD$_3$OD) δ 7.38-7.02 (m, 17H), 6.95 (m, 1H), 6.75 (m, 1H), 5.03 (s, 2H), 4.97 (d, J=5.01 Hz, 1H), 4.22 (d, J=14.3 Hz, 1H), 4.09 (ddd, J=1.50, 4.96, 5.01 Hz, 1H), 4.03 (d, J=14.3 Hz, 1H), 3.87 (d, J=13.8 Hz, 1H), 3.64 (s, 1H), 3.04-2.73 (m, 5H), 0.57 (s, 9H); $^{13}$C NMR (CD$_3$OD) δ 177.5, 172.3, 158.3, 142.0, 141.4, 138.8, 138.2, 137.6, 131.6, 129.6, 129.5, 129.3, 129.0, 128.9, 128.8, 128.7, 128.4, 127.7, 127.5, 126.0, 125.6, 79.2, 73.9, 68.4, 67.7, 63.0, 62.8, 58.5, 44.4, 40.1, 34.9, 26.6; MS (m/z 679, M+H$^+$); Anal. (C$_{40}$H$_{46}$N$_4$O$_6$) C, H, N.

Example 14

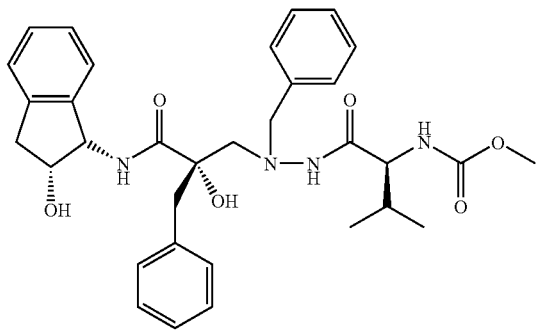

{(1S)-1-[N'-Benzyl-N'-((2S)-2-hydroxy-2-((1S,2R)-2-hydroxy-indan-1-ylcarbamoyl)-3-phenyl-propyl)-hydrazinocarbonyl]-2-methyl-propyl}-carbamic acid methyl ester (14)

The title compound was prepared according to Method A using epoxide 2a (0.100 g, 0.323 mmol) and hydrazide 5 (0.117 g, 0.419 mmol), heating for 96 h. Purification by column chromatography (silica, EtOAc/pentane, 40:60-100:0) followed by RP-LC-MS (30 min gradient of 20-100% CH$_3$CN in 0.05% aqueous HCOOH) gave the product (0.0358 g, 19%) as a white solid.

$[\alpha]_D^{19}$ −50.9° (c 0.99, CHCl$_3$); $^1$H NMR (CDCl$_3$) δ 7.59 (s, 1H), 7.44-7.00 (m, 14H), 6.36 (s, 1H), 5.17 (m, 2H), 4.30 (d, J=13.0 Hz, 1H), 4.14 (m, 1H), 4.06 (d, J=7.38 Hz, 1H), 4.02 (d, J=7.38 Hz, 1H), 3.78-3.62 (m, 4H), 3.06-2.74 (m, 5H), 1.81 (m, 1H), 1.72 (s, 1H), 0.66-0.52 (m, 7H); $^{13}$C NMR (CDCl$_3$) δ 174.8, 171.4, 157.2, 140.6, 140.2, 136.8, 136.6, 130.9, 128.8, 128.7, 128.3, 128.1, 128.0, 127.2, 127.0, 125.3, 124.1, 78.3, 73.4, 67.1, 62.5, 59.3, 58.0, 52.8, 43.9, 39.1, 30.8, 18.9, 17.7; MS (m/z 589, M+H$^+$); Anal. (C$_{33}$H$_{40}$N$_4$O$_6$) C, H, N.

Example 15

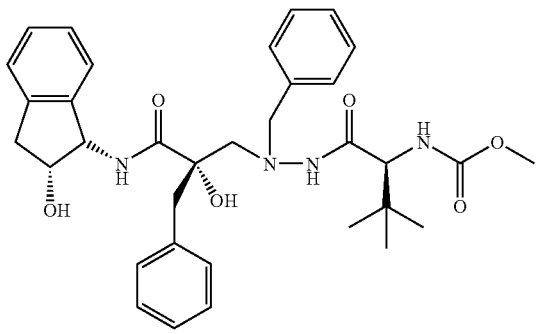

{(1S)-1-[N'-Benzyl-N'-((2S)-2-hydroxy-2-((1S,2R)-2-hydroxy-indan-1-ylcarbamoyl)-3-phenyl-propyl)-hydrazinocarbonyl]-2,2-dimethyl-propyl}-carbamic acid methyl ester (15)

The title compound was prepared according to Method A from epoxide 2a (0.101 g, 0.326 mmol) and hydrazide 6 (0.125 g, 0.426 mmol) by heating for 96 h. Column chromatography (silica, EtOAc/pentane, 40:60-100:0) followed by RP-LC-MS (30 min gradient of 20-100% CH$_3$CN in 0.05% aqueous HCOOH) gave the product (0.0919 g, 46%) as a white solid.

$[\alpha]_D^{21}$ −44.8° (c 1.01, CHCl$_3$); $^1$H NMR (CDCl$_3$) δ 7.53 (s, 1H), 7.44-6.98 (m, 14H), 6.52 (s, 1H), 5.43 (d, J=9.04 Hz, 1H), 5.15 (dd, J=4.64, 9.04 Hz, 1H), 4.35 (d, J=14.7 Hz, 1H), 4.09 (m, 2H), 4.02 (d, J=14.7 Hz, 1H), 3.71 (m, 4H), 3.05-2.74 (m, 5H), 1.76 (s, 1H), 0.69 (s, 9H), 0.52 (m, 1H); $^{13}$C NMR (CDCl$_3$) δ 174.8, 170.8, 157.3, 140.6, 140.2, 136.8, 136.7, 131.0, 128.8, 128.6, 128.2, 128.1, 128.0, 127.2, 127.0, 125.2, 124.3, 78.3, 73.4, 67.6, 62.2, 61.6, 57.8, 52.9, 43.9, 39.1, 34.6, 26.2; MS (m/z 603, M+H$^+$); Anal. (C$_{34}$H$_{42}$N$_4$O$_6$) C, H, N.

Example 16

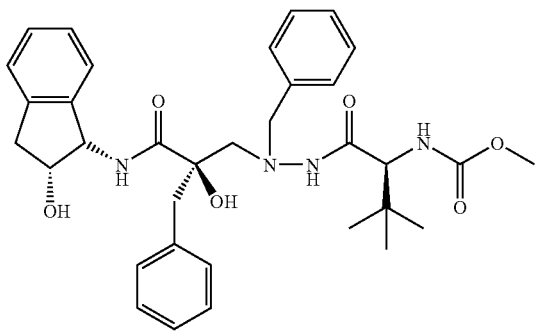

{(1S)-1-[N'-Benzyl-N'-((2R)-2-hydroxy-2-((1S,2R)-2-hydroxy-indan-1-ylcarbamoyl)-3-phenyl-propyl)-hydrazinocarbonyl]-2,2-dimethyl-propyl}-carbamic acid methyl ester (16)

The title compound was prepared according to Method A from epoxide 2b (0.100 g, 0.323 mmol) and hydrazide 6 (0.147 g, 0.501 mmol) by heating for 96 h. Purification by RP-LC-MS (30 min gradient of 20-100% CH$_3$CN in 0.05% aqueous HCOOH) gave the product as a white solid (0.103 g, 53%).

$[\alpha]_D^{21}$ −6.06° (c 0.99, CHCl$_3$); $^1$H NMR (CD$_3$OD) δ 7.44-7.05 (m, 11H), 6.97 (m, 2H), 6.25 (d, J=7.44 Hz, 1H), 5.08 (m, 1H), 4.40 (m, 1H), 4.09 (d, J=13.8 Hz, 1H), 4.02 (d, J=13.8 Hz, 1H), 3.70 (m, 2H), 3.56 (s, 3H), 3.10-2.77 (m, 5H), 0.76 (s, 9H); $^{13}$C NMR (CD$_3$OD) δ 176.5, 172.1, 158.8, 141.9, 141.2, 138.5, 137.6, 131.9, 130.0, 129.2, 129.0, 128.7, 128.4, 127.61, 127.56, 125.8, 125.4, 79.4, 74.1, 67.8, 63.1, 62.9, 58.2, 52.7, 44.1, 40.8, 35.1, 26.8; MS (m/z 603, M+H$^+$); Anal. (C$_{34}$H$_{42}$N$_4$O$_6$) C, H, N.

Example 17

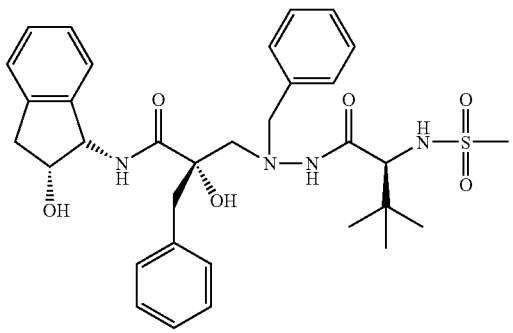

(2S)-2-Benzyl-3-[N-benzyl-N'-((2S)-2-methanesulfonylamino-3,3-dimethyl-butyryl)-hydrazino]-2-hydroxy-N-((1S,2R)-2-hydroxy-indan-1-yl)-propionamide (17)

The title compound was prepared according to Method A using epoxide 2a (0.100 g, 0.323 mmol) and hydrazide 7 (0.131 g, 0.418 mmol) by heating for 96 h. Purification by column chromatography (silica, EtOAc/pentane, 40:60-100:0) followed by RP-LC-MS (30 min gradient of 20-100% CH$_3$CN in 0.05% aqueous HCOOH) gave the product (0.0864 g, 43%) as a white solid.

$[\alpha]_D^{21}$ −8.70° (c 1.0, CHCl$_3$); $^1$H NMR (CD$_3$OD/CDCl$_3$, 1:1) δ 7.36-7.02 (m, 13H), 6.84 (m, 1H), 5.12 (d, J=5.04 Hz, 1H), 4.29 (ddd, J=5.11, 5.04, 1.94 Hz, 1H), 4.24 (d, J=14.5 Hz, 1H), 4.00 (d, J=14.5 Hz, 1H), 3.93 (d, J=14.1 Hz, 1H), 3.15 (s, 1H), 3.07-3.96 (m, 2H), 2.90-2.83 (m, 2H), 2.74 (d, J=14.4 Hz, 1H), 2.42 (s, 3H), 0.51 (s, 9H); $^{13}$C NMR (CDCl$_3$) δ 174.7, 170.2, 140.3, 139.9, 136.4, 136.2, 130.8, 128.5, 128.4, 128.3, 128.0, 127.9, 127.0, 126.8, 125.1, 124.1, 77.8, 73.1, 67.2, 63.6, 62.3, 57.4, 43.4, 40.9, 39.0, 34.2, 26.0; MS (m/z 623, M+H$^+$). Anal. (C$_{33}$H$_{42}$N$_4$O$_6$S) C, H, N.

Example 18

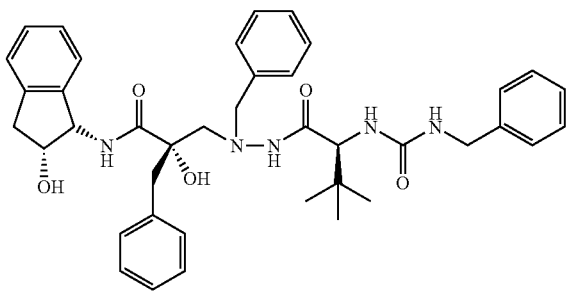

(2S)-2-Benzyl-3-{N-Benzyl-N'-[(2S)-2-(3-benzyl-ureido)-3,3-dimethyl-butyryl]-hydrazino}-2-hydroxy-N-((1S,2R)-2-hydroxy-indan-1-yl)-propionamide (18)

The title compound was prepared according to Method A from epoxide 2a (0.0655 g, 0.212 mmol) and hydrazide 8 (0.102 g, 0.277 mmol) by heating for 72 h. Purification by RP-LC-MS (30 min gradient of 0-90% CH$_3$CN in 0.05% aqueous HCOOH) gave the product (0.0353 g, 25%) as a white solid.

$[\alpha]_D^{21}$ +30.7° (c 0.45, CHCl$_3$/MeOH, 2:1); $^1$H NMR (CD$_3$OD) δ 7.38-7.02 (m, 17H), 6.96 (m, 1H), 6.77 (m, 1H), 4.98 (d, J=4.98 Hz, 1H), 4.28 (s, 2H), 4.25 (d, J=19.1 Hz, 1H), 4.05 (m, 2H), 3.90 (d, J=14.1 Hz, 1H), 3.76 (m, 1H), 3.05-2.76 (m, 5H), 0.58 (s, 9H); $^{13}$C NMR (CD$_3$OD) δ 177.5, 173.0, 160.3, 142.0, 141.4, 141.1, 138.9, 137.6, 131.6, 129.6, 129.5, 129.3, 128.9, 128.7, 128.4, 128.2, 128.0, 127.6, 127.5, 126.0, 125.6, 79.3, 73.9, 68.5, 62.8, 61.3, 58.5, 44.7, 44.5, 40.8, 34.9, 26.7; MS (m/z 678, M+H$^+$); Anal. (C$_{40}$H$_{47}$N$_5$O$_5$) C, H, N.

Example 19

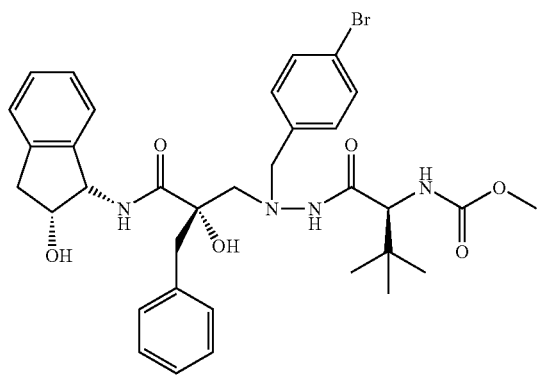

{(1S)-1-[N'-(4-Bromo-benzyl)-N'-((2S)-2-hydroxy-2-((1S,2R)-2-hydroxy-indan-1-ylcarbamoyl)-3-phenyl-propyl)-hydrazinocarbonyl]-2,2-dimethyl-propyl}-carbamic acid methyl ester (19)

The title compound was prepared according to Method B from epoxide 2a (0.250 g, 0.809 mmol) and hydrazide 9 (0.331 g, 0.889 mmol) which gave the product (0.304 g, 55%) as a white solid.

$[\alpha]_D^{19}$ +2.65° (c 0.72, DMF); $^1$H NMR (CD$_3$OD) δ 7.35-7.03 (m, 11H), 6.92 (m, 1H), 6.77 (m, 1H), 4.96 (d, J=4.97 Hz, 1H), 4.14 (d, J=14.7 Hz, 1H), 4.13 (m, 1H), 4.02 (d, J=14.7 Hz, 1H), 3.87 (d, J=13.9 Hz, 1H), 3.60 (m, 4H), 3.09-2.75 (m, 5H), 0.60 (s, 9H); $^{13}$C NMR (CD$_3$OD) δ 177.5, 172.4, 158.9, 142.1, 141.4, 138.2, 137.5, 132.3, 131.6, 131.4, 128.9, 128.8, 127.6, 127.4, 126.0, 125.6, 122.0, 79.2, 73.7, 68.4, 62.9, 62.0, 58.4, 52.7, 44.3, 40.7, 34.8, 26.6; MS (m/z 681, M+H$^+$, 683, M+H$^+$); Anal. (C$_{34}$H$_{41}$BrN$_4$O$_6$) C, H, N.

Example 20

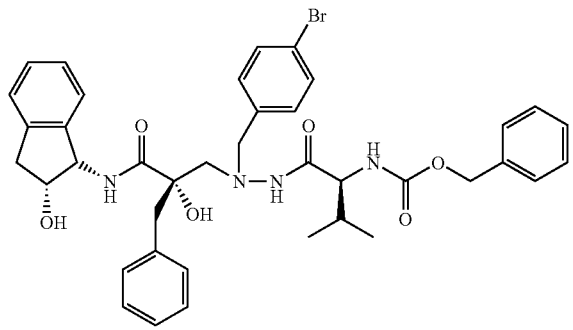

{(1S)-1-[N'-(4-Bromo-benzyl)-N'-((2S)-2-hydroxy-2-((1S,2R)-2-hydroxy-indan-1-ylcarbamoyl)-3-phenyl-propyl)-hydrazinocarbonyl]-2-methyl-propyl}-carbamic acid benzyl ester (20)

The title compound was prepared according to Method A from epoxide 2a (0.550 g, 0.178 mmol) and hydrazide 10 (0.0650 g, 0.150 mmol) by heating for 168 h. Purification by RP-LC-MS (25 min gradient of 30-80% CH$_3$CN in 0.05% aqueous HCOOH) gave the product (0.0172 g, 13%) as a white solid.

$[\alpha]_D^{22}$ −24.4° (c 0.88, MeOH/DMF 2:1); $^1$H NMR (DMSO-d$_6$ +2 drops of D$_2$O) δ 7.40-7.01 (m, 16H), 6.76 (m, 2H), 4.97 (d, J=12.9 Hz, 1H), 4.93 (d, J=12.9 Hz, 1H), 4.87 (d, J=4.99 Hz, 1H), 4.05 (m, 3H), 3.72 (d, J=14.3 Hz, 1H), 3.51 (m, 1H), 3.02-2.55 (m, 5H), 1.53 (m, 1H), 0.53 (d, J=6.70 Hz, 3H), 0.39 (d, J=6.70 Hz, 3H); $^{13}$C NMR (DMSO-d$_6$ +2 drops of D$_2$O) δ 175.2, 171.5, 156.6, 142.6, 141.1, 137.9, 137.6, 137.0, 131.3, 130.94, 130.86, 129.0, 128.5, 128.32, 128.27, 127.9, 126.9, 126.5, 125.5, 124.7, 120.6, 78.2, 72.3, 67.7, 66.1, 60.8, 59.5, 57.0, 43.4, 40.5, 30.5, 19.2, 18.6; MS (m/z 743, M+H$^+$, 745, M+H$^+$); Anal. (C$_{39}$H$_{43}$BrN$_4$O$_6$) C, H, N.

Example 21

Step a)

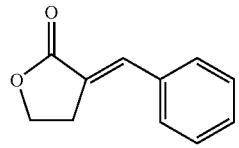

3-[1-Phenyl-meth-(E)-ylidene]-dihydro-furan-2-one (21a)

The title compound was prepared as described in Tetrahedron, 57, 25, 2000, p. 5353-5360.

Sep b)

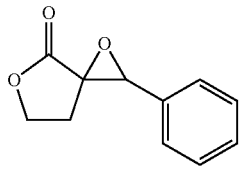

2-Phenyl-1,5-dioxa-spiro[2,4]heptan-4-one (21b)

To a solution of 3-[1-phenyl-meth-(E)-ylidene]-dihydro-furan-2-one (21a) (4.0 g, 22.9 mmol) and 3-chloroperoxybenzoic acid (6.18 g, 27.6 mmol) in 1,2-dichloroetheane (70 mL) was added catalytic amount of AIBN (50 mg) at 80° C. and refluxed in the dark for 6 h. The resulting solution was cooled and filtered, the solvent was removed under reduced pressure, and the residue dissolved in dichloromethane. The organic phase was washed consecutively with saturated aqueous solutions of NaHCO$_3$ (20 mL), KI (20 mL), Na$_2$S$_2$O$_3$ (20 mL), and NaHCO$_3$ (20 mL) then dried over anhydrous MgSO$_4$ and evaporated under reduced pressure. Product was purified by silica gel flash chromatography using ethyl acetate:petroleum ether (1:4) gave 2.62 g in 60% yield of the title compound.

MS (ESI$^+$): m/z: 191 (M$^+$+1) $^1$H NMR (CDCl$_3$, 400 MHz): δ 7.39 (m, 3H), 7.26 (m, 2H), 4.54 (dt, J=9.5 Hz, 3.3 Hz, 1H), 4.39 (s, 1H), 4.29 (m, 1H), 2.49 (m, 1H), 2.07 (m, 1H); $^{13}$C NMR (CDCl$_3$, 100 MHz): δ 173.2, 133.1, 129.1, 128.8, 126.4, 64.8, 62.4, 61.7, 22.7

Step c)

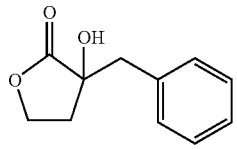

3-Benzyl-3-hydroxy-dihydro-furan-2-one (21c)

Method A: Platinum (IV) oxide (0.1 g) was added to a solution of 2-phenyl-1,5-dioxa-spiro[2.4]heptan-4-one (21b) (2.0 g, 10.5 mmol) in ethyl acetate (40 mL) and placed in Parr hydrogenation set-up at 50 Psi for 3 h. Catalyst was filtered, and filtrate was evaporated and purified by silica gel flash chromatography using petroleum ether:ethyl acetate as eluent to give the title compound (1.3 g, 64% yield).

Method B: To a mixture of 2-phenyl-1,5-dioxa-spiro[2.4]heptan-4-one (21b) (1.903 g, 10 mmol) and Pd/C (Degussa type E101 NE/W, 0.530 g, 2.5 mol % Pd) and 20 mL EtOAc in a reaction tube was added formic acid (0.604 mL, 16 mmol) and triethylamine (2.09 mL, 15 mmol). The tube was sealed with a screw cap and heated at 80° C. for 3 h. The reaction mixture was allowed to cool to room temperature, the catalyst was filtered off and volatiles were evaporated under reduced pressure. The residue was purified by flash column chromatography on silica gel (Hex/EtOAc 1:1) which gave the title compound as a colorless solid (1.851 g, 9.627 mmol, 96%).

MS (ESI$^+$): m/z: 192 (M$^+$) $^1$H NMR (CDCl$_3$, 400 MHz): δ 7.34-7.23 (m, 5H), 4.26 (m, 1H), 3.75 (m, 1H), 3.05 (s, 2H), 3.04 (s, 1H), 2.39-2.24 (m, 2H); $^{13}$C NMR (CDCl$_3$, 100 MHz): δ 178.9, 134.2, 130.1, 128.7, 128.5, 127.5, 75.5, 65.3, 43.4, 34.0

Step d)

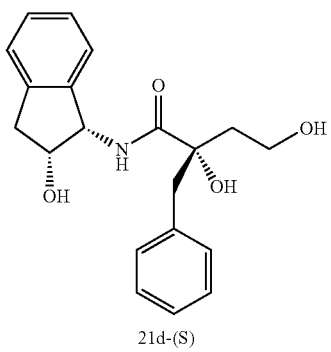

21d-(S)

-continued

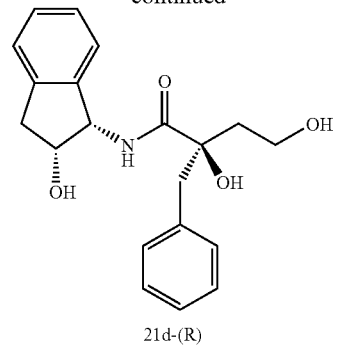

21d-(R)

(S)-2-Benzyl-2,4-dihydroxy-N-((1S,2R)-2-hydroxy-indan-1-yl)-butyramide (21d-(S)) and (R)-2-Benzyl-2,4-dihydroxy-N-((1S,2R)-2-hydroxy-indan-1-yl)-butyramide (21d-(S))

3-Benzyl-3-hydroxy-dihydro-furan-2-one (21c) (0.5 g, 2.6 mmol) and 2-hyroxypyridine (0.27 g, 2.8 mmol) in dry dichloromethane (15 mL) was added (1S,2R)-(-)-cis-1-amino-2-indanol (0.43 g, 2.8 mmol). The reaction mixture was stirred at 50° C. for 24 h and then evaporated. The residue was dissolved in ethyl acetate (80 mL) and washed with 1M HCl (20 mL), followed by saturated aqueous NaHCO$_3$ (20 mL), and thereafter dried, filtered, and concentrated. The residue purified by silica gel flash chromatography using petroleum ether:acetone (3:1) gave 0.26 g of first eluted (compound 21d-(S)) and 0.33 g of second eluted (compound 21d-(R)) together in 66% yield of the title compounds.

21d-(S): MS (ESI$^+$): m/z: 342 (M$^+$+1)
$^1$H NMR (DMSO-d$_6$, 400 MHz): δ 7.64 (m, 1H), 7.31-7.10 (m, 9H), 5.52 (s, 1H), 5.05 (m, 2H), 4.73 (s, 1H), 4.16 (m, 1H), 3.61 (m, 2H), 3.05-3.00 (m, 2H), 2.86 (d, J=13.36 Hz, 1H), 2.76 (d, J=16.48 Hz, 1H), 2.14 (m, 1H), 1.73 (m, 1H); $^{13}$C NMR (DMSO-d$_6$, 100 MHz): δ 174.8, 143.0, 141.0, 137.4, 130.9, 128.1, 127.7, 126.8, 126.6, 125.5, 124.5, 77.8, 72.4, 57.8, 56.9, 45.8, 41.4, 40.5 (hidden in DMSO)

21d-(R): MS (ESI$^+$): m/z: 342 (M$^+$+1)
$^1$H NMR (CD$_3$OD, 400 MHz): δ 7.61 (d, J=8.79 Hz, 1H), 7.33-7.24 (m, 5H), 7.17-7.10 (m, 2H), 6.97 (m, 1H), 6.25 (d, J=7.32 Hz, 1H), 5.10 (m, 1H), 4.46 (m, 1H), 3.77 (m, 2H), 3.16 (d, J=13.36 Hz, 1H), 3.07 (dd, J=16.48, 4.94 Hz, 1H), 2.91 (d, J=13.36 Hz, 1H), 2.82 (d, J=16.48 Hz, 1H), 2.28 (m, 1H), 1.91 (m, 1H); $^{13}$C NMR (CD$_3$OD, 100 MHz): δ 175.6, 140.4, 140.0, 136.5, 130.5, 127.6, 127.5, 126.2, 124.6, 123.8, 77.9, 72.7, 57.8, 56.9, 56.8, 45.5, 41.3, 39.3

Step e)

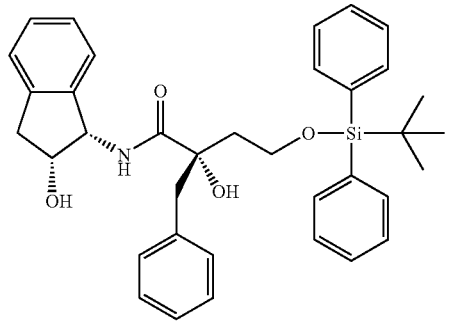

(S)-2-Benzyl-4-(tert-butyl-diphenyl-silanyloxy)-2-hydroxy-N-((1S,2R)-2-hydroxy-indan-1-yl)-butyramide (21e)

To a stirred solution of (S)-2-benzyl-2,4-dihydroxy-N-((1S,2R)-2-hydroxy-indan-1-yl)-butyramide(21d-(S)) (0.245 g, 0.72 mmol) and imidazole (0.73 g, 1.08 mmol) in dry dichloromethane (25 mL) was added TBDPS-Cl (0.2 g, 0.75 mmol) and left overnight. The reaction mixture was diluted, washed with water, dried, evaporated and purified over silica gel flash chromatography to yield 0.334 g (80%) of the title compound.

MS (ESI$^+$): m/z: 580 (M$^+$) $^1$H NMR (CDCl$_3$, 400 MHz): δ 7.71-7.66 (m, 4H), 7.48-7.36 (m, 8H), 7.34-7.24 (m, 4H), 7.22-7.18 (m, 2H), 7.12-7.04 (m, 2H), 5.37 (s, 1H), 5.24 (m, 1H), 4.17 (m, 1H), 4.15 (dd, J=10.4 Hz, 2.4 Hz, 1H), 4.10 (m, 1H), 3.10 (d, J=13.6 Hz, 1H), 3.05 (m, 2H), 2.81 (d, J=16.4 Hz, 1H), 2.40 (m, 1H), 2.15 (m, 1H), 1.09 (s, 9H); $^{13}$C NMR (CDCl$_3$, 100 MHz): δ 174.6, 140.5, 137.5, 135.7, 135.6, 132.4, 131.0, 130.4, 128.3, 128.2, 128.1, 127.1, 126.9, 125.3, 124.0, 80.9, 73.4, 63.5, 57.4, 46.0, 39.0, 38.8, 30.0, 27.0

Step f)

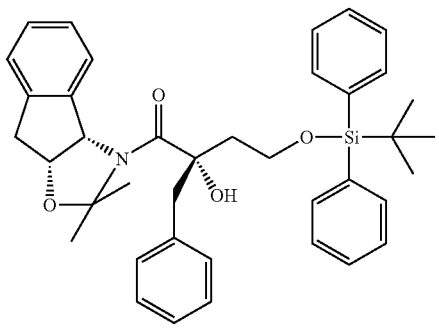

(S)-2-Benzyl-4-(tert-butyl-diphenyl-silanyloxy)-1-((3aS,8aR)-2,2-dimethyl-8,8a-dihydro-3 aH-indeno[1,2-d]oxazol-3-yl)-2-hydroxy-butan-1-one (21f)

To a cooled (0° C.) solution of (S)-2-benzyl-4-(tert-butyl-diphenyl-silanyloxy)-2-hydroxy-N-((1S,2R)-2-hydroxy-indan-1-yl)-butyramide (21e) (0.325 g, 0.56 mmol) and pyridinium p-toluenesulphonic acid (15 mg, 0.05 mmol) in dry dichloromethane (20 mL), 2-methoxypropene (0.4 g, 5.6 mmol) was added and stirred for 6 h at the same temperature. Saturated NaHCO$_3$ solution was added, organic layer and washed with sat. NaHCO$_3$, brine, dried over anhydrous MgSO$_4$ and evaporated under reduced pressure. The crude title product [(0.33 g), MS (ESI$^+$): 620 (M$^+$)] was used as such for the next reaction.

Step g)

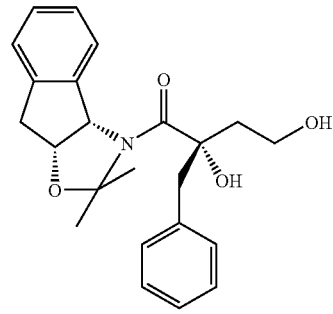

(S)-2-Benzyl-1-((3aS,8aR)-2,2-dimethyl-8,8a-dihydro-3aH-indeno[1,2-d]oxazol-3-yl)-2,4-dihydroxy-butan-1-one (21g)

TBAF (0.278 g, 1.06 mmol, 1M in THF) was added to a solution of (S)-2-benzyl-4-(tert-butyl-diphenyl-silanyloxy)-1-((3aS,8aR)-2,2-dimethyl-8,8a-dihydro-3 aH-indeno[1,2-d]oxazol-3-yl)-2-hydroxy-butan-1-one (21f) (0.33 g, 0.53 mmol) in THF (20 mL) at room temperature and stirred for 3 h. Solvent was evaporated and the residue dissolved in dichloromethane and washed with water, brine, dried and evaporated. The product purified by flash chromatography using petroleum ether:acetone (4:1) to get 0.145 g of the title product in 69% yield from two steps.

MS (ESI$^+$): m/z: 382 (M$^+$+1) $^1$H NMR (CDCl$_3$, 400 MHz): δ 7.34-7.25 (m, 4H), 7.20-7.09 (m, 5H), 5.25 (m, 1H), 4.23 (m, 1H), 4.10-4.00 (m, 2H), 3.15 (d, J=12.8 Hz, 1H), 3.06 (dd, J=16.4 Hz, 5.6 Hz, 1H), 2.96 (d, J=13.2 Hz, 1H), 2.83 (d, J=16.4 Hz, 1H), 2.40 (m, 1H), 2.16 (s, 6H), 2.10 (m, 1H); $^{13}$C NMR (CDCl$_3$, 100 MHz): δ 175.4, 140.6, 140.4, 136.7, 130.9, 128.2, 128.0, 127.3, 127.2, 127.1, 125.4, 123.9, 80.2, 73.3, 61.2, 57.5, 46.2, 39.3, 39.2, 31.1, 29.4

Step h)

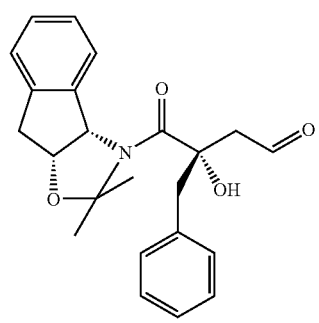

(S)-3-Benzyl-4-((3aS,8aR)-2,2-dimethyl-8,8a-dihydro-3aH-indeno[1,2-d]oxazol-3-yl)-3-hydroxy-4-oxo-butyraldehyde (21h)

A solution of (S)-2-benzyl-1-((3aS,8aR)-2,2-dimethyl-8,8a-dihydro-3aH-indeno[1,2-d]oxazol-3-yl)-2,4-dihydroxybutan-1-one (21g) (0.13 g, 0.34 mmol) in dry CH$_2$Cl$_2$ (5 mL) was added over 1 min to a stirred solution of Dess-Martin periodinate (0.16 g, 0.37 mmol) in dry CH$_2$Cl$_2$ (10 mL). After 30 min the homogeneous mixture was diluted with ether and poured into cold saturated NaHCO$_3$ (10 mL) containing Na$_2$S$_2$O$_3$ (2.2 g). Organic layers were washed with aqueous saturated NaHCO$_3$, brine and dried (MgSO$_4$). The solvents were evaporated below 20° C. to give the title compound (0.082 g, 64%). The residue [MS (ESI$^+$): 380 (M$^+$+1)] was immediately used for the next step.

Step i)

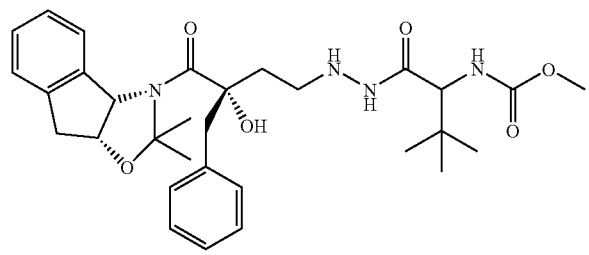

((S)-1-{N'-[(S)-3-Benzyl-4-((3aS,8aR)-2,2-dimethyl-8,8a-dihydro-3aH-indeno[1,2-d]oxazol-3-yl)-3-hydroxy-4-oxo-butyl]-hydrazinocarbonyl}-2,2-dimethyl-propyl)-carbamic acid methyl ester (21i)

(S)-3-Benzyl-4-((3aS,8aR)-2,2-dimethyl-8,8a-dihydro-3aH-indeno[1,2-d]oxazol-3-yl)-3-hydroxy-4-oxo-butyraldehyde (21h) (0.082 g, 0.21 mmol) and [N-(methoxycarbony)-L-tert-leucinyl]hydrazine (0.048 g, 0.23 mmol, prepared as reported JMC, 41, 3387, 1998) in dry THF (10 mL) was stirred for 3 h and [the LCMS (ESI$^+$) shows 565 (M$^+$)], then Na(OAc)$_3$BH (0.137 g, 0.64 mmol) was added and stirred overnight. The reaction mixture was quenched with water and evaporated. The residue was dissolved in dichloromethane and washed with water, brine and dried. The crude product was analysed by LCMS (ESI$^+$) which showed 567 (M$^+$) the title compound with a minor quantity of the compound lacking the protection group on the indanol moiety [MS (ESI$^+$): 527 (M$^+$)]. This mixture was alkylated by the next step without purification.

Step j)

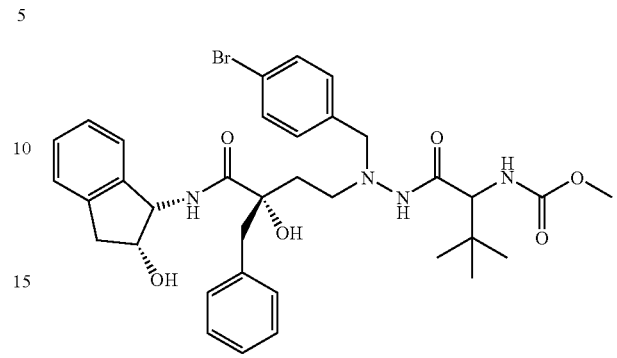

((R)-(1-{N'-(4-Bromo-benzyl)-N'-[(R)-3-hydroxy-3-((1S,2R)-2-hydroxy-indan-1-ylcarbamoyl)-4-phenyl-butyl]-hydrazinocarbonyl}-2,2-dimethyl-propyl)-carbamic acid methyl ester (22)

Compound 21i (0.105 g) was dissolved in 2-butanone (10 mL) and added K$_2$CO$_3$ (0.045 g, 0.32 mmol), and 4-bromobenzyl bromide (0.054 g, 0.21 mmol) and stirred at 80° C. for 3 h. Solvent was evaporated and the residue was dissolved in dichloromethane (15 mL), washed with water, brine and cooled to 0° C. TFA (1.0 mL) was added slowly and stirred for 30 min then evaporated. Residue dissolved in dichloromethane (10 mL) and washed with NaHCO$_3$ solution, water, brine and dried. Residue was purified by analytical preparative LCMS to yield 0.023 g (15% overall yield) of the title compound.

MS (ESI$^+$): m/z: 695, 697 (M$^+$) $^1$H NMR (CDCl$_3$, 400 MHz): δ 7.40-7.12 (m, 1H), 7.04-6.98 (m, 2H), 6.42 (s, 1H), 6.08 (s, 1H), 5.18 (m, 2H), 4.16 (m, 1H), 3.97 (d, J=14.0 Hz, 1H), 3.77 (d, J=13.2 Hz, 1H), 3.66 (s, 3H), 3.56 (d, J=9.6 Hz, 1H), 3.12-3.01 (m, 4H), 2.82 (m, 2H), 2.32 (m, 1H), 1.94 (m, 1H), 0.79 (s, 9H)

Example 22

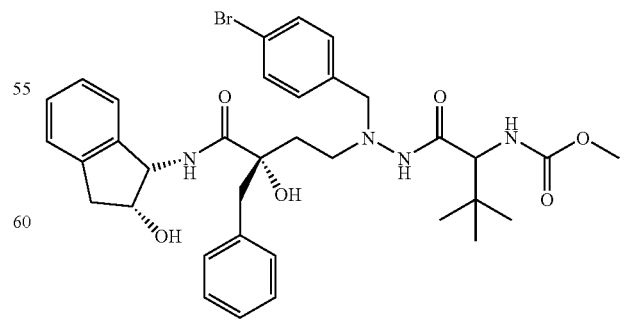

((R)-(1-{N'-(4-Bromo-benzyl)-N'-[(S)-3-hydroxy-3-((1S,2R)-2-hydroxy-indan-1-ylcarbamoyl)-4-phenyl-butyl]-hydrazinocarbonyl}-2,2-dimethyl-propyl)-carbamic acid methyl ester (22)

Compound 22d-(R) was taken through the steps a-j of example 21 as described for compound 22-(S) which gave the title compound Example 23

Step a)

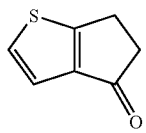

5,6-Dihydro-cyclopenta[b]thiophen-4-one (23a)

Over a period of 10 minutes a solution of triflic anhydride (84.7 g, 0.30 mol) in DCE (300 mL) was added to a cold solution of N,N-dimethylacrylamide (29.8 g, 0.30 mol) in DCE (2700 mL). The mixture was stirred for 15 minutes at 0° C. A solution of thiophene (25.3 g, 0.30 mol) was added and the mixture was refluxed for seven hours. A solution of potassium carbonate (150 g in 200 mL of water) was added. The mixture was extracted two times with DCM dried over sodium sulphate and evaporated under reduced pressure. The compound was purified by silica gel chromatography with ethyl acetate/hexane.

Yield: 36.8 g=53%

$^1$H-NMR CDCl$_3$ 7.32 (dd, 1H), 7.14 (dd, 1H), 3.20 (m, 2H), 3.00 (m, 2H)

Step b

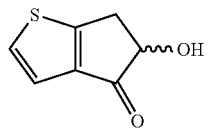

5-Hydroxy-5,6-dihydro-cyclopenta[b]thiophen-4-one (23b)

5,6-dihydro-cyclopenta[b]thiophen-4-one (36.8 g, 0.266 mol) in MeOH (1000 mL) was added at about 5° C. to a solution of potassium hydroxide 85% (52.7 g, 0.798 mol) in MeOH (500 mL). Between 0° C. and 5° C. iodobenzene diacetate (94.4 g, 0.293 mol) was added in portions and the mixture was allowed to come to room temperature. The mixture was stirred overnight at room temperature. The mixture was evaporated and a 20% solution of potassium carbonate (500 mL) was added. The mixture was extracted for times with DCM dried with sodium sulphate and evaporated under reduced pressure. The residue was dissolved in 1,4-dioxane (400 mL) and water (150 mL) and concentrated hydrochloric acid (150 mL) was added. The mixture was stirred for two hours at room temperature. The mixture was neutralized by the addition of potassium carbonate and extracted four times with dichloromethane. The organic phase was dried with sodium sulphate and evaporated under reduced pressure. The product was crystallized with ether ethyl acetate and the mother liquid was purified by silica gel chromatography with toluene and acetone. Yield: 33.5 g=81.6%.

$^1$H-NMR CDCl$_3$ δ 7.36 (dd, 1H), 7.18 (d, 1H), 4.76 (m, 1H), 3.64 (m, 2H), 3.10 (m, 1H)

Step c)

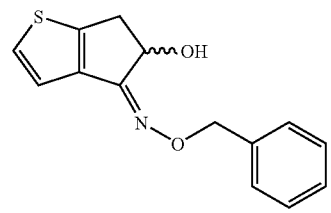

5-Hydroxy-5,6-dihydro-cyclopenta[b]thiophen-4-one O-benzyl-oxime (23c)

To a solution of 5-hydroxy-5,6-dihydro-cyclopenta[b]thiophen-4-one (33.4 g, 0.216 mol) in pyridine (300 mL) was added O-benzylhydroxylamine hydrochloride (38.3 g, 0.240 mol) and the mixture was stirred at room temperature over weekend. The mixture was evaporated under reduced pressure and co-evaporated two times with toluene. Ethyl acetate was added and the organic phase was washed with 5% citric acid and brine. The organic phase was dried with sodium sulphate and evaporated under reduced pressure. Yield. 55.1 g=98%

$^1$H-NMR CDCl$_3$ δ 7.40-7.20 (m, 7H), 5.20 (m, 3H), 3.45 (m, 2H), 3.0 (m, 1H)

Step d)

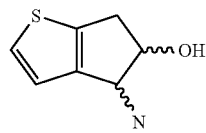

cis-4-Amino-5,6-dihydro-4H-cyclopenta[b]thiophene-5-ol (racemate) (23d)

A solution of 5-hydroxy-5,6-dihydro-cyclopenta[b]thiophen-4-one O-benzyl-oxime (55.1 g, 0.212 mol) was added drop wise at about 5° C. to 1.0 M solution of borane in THF (650 mL) and the mixture was stirred at room temperature overnight. The mixture was refluxed for two hours and cooled to about 5° C. Water (70 mL) and 20% potassium hydroxide solution (80 mL) was added dropwise. The mixture was refluxed for two hours and cooled. Brine was added and the THF removed under reduced pressure. The mixture was extracted five times with DCM, dried with sodium sulphate and evaporated under reduced pressure. The product was purified by silica gel chromatography with DCM and 10% methanol. Yield: 17.8 g=54%

$^1$H-NMR DMSO-d$_6$ δ 7.30 (d, 1H), 6.92 (d, 1H), 4.46 (m, 1H), 4.20 (m, 1H) 3.99-3.84 (dd, 2H)

Example 24

Separation of the Enantiomeres from Example 23

Step a)

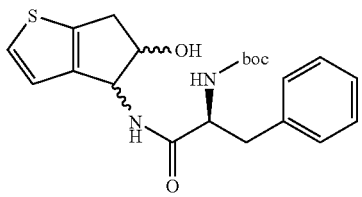

[1-(5-Hydroxy-5,6-dihydro-4H-cyclopenta[b]
thiophen-4-ylcarbamoyl)-2-phenyl-ethyl]-carbamic
acid tert-butyl ester (24a)

To a mixture of the racemic cis-4-amino-5,6-dihydro-4H-cyclopenta[b]thiophen-5-ol (17.5 g, 0.112 mol) in dry DMF (400 mL) was added Boc-L-phenylalanin (30.51 g, 0.115 mol) HOBT (15.6 g, 0.115 mol) and EDAC (22.0 g, 0.115 mol). To the stirred mixture was added TEA (16 mL, 0.115 mol) and the mixture was stirred at room temperature overnight. The mixture was added to 5% citric acid and extracted three times with ethyl acetate. The organic phase was washed with brine and saturated sodium hydrogen carbonate (two times). The organic phase was dried with sodium sulphate and evaporated under reduced pressure. Yield: 43 g=95%

Step b)

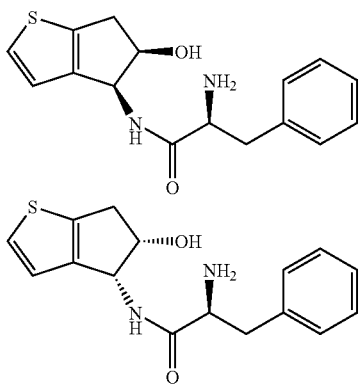

2-Amino-N-(5-hydroxy-5,6-dihydro-4H-cyclopenta
[b]thiophen-4-yl)-3-phenyl-propionamide (24b)

Compound 24a was dissolved in chloroform (400 mL) and TFA (100 mL) was added and the mixture was stirred for three hours at room temperature. The organic phase was washed two times with 15% ammonia solution (300 mL) and with brine. The organic phase was dried over sodium sulphate and evaporated. The product was purified by silica gel chromatography with DCM with three to ten percent methanol.

Yield A 12.5 g first diastereomere=40%
Yield B 12.5 g second diastereomere=40%

Step c)

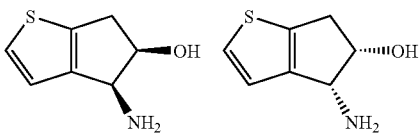

4-Amino-5,6-dihydro-4H-cyclopenta[b]thiophen-5-ol
(24c)

The first diastereomere (12.4 g, 41 mmol) was dissolved in EtOH (400 mL) and a solution of sodium hydroxide (21.0 g, 525 mmol) water (300 mL) was added. The mixture was refluxed overnight. The ethanol was removed and the alkaline phase was extracted six times with DCM. The organic phase was washed with brine, dried with sodium sulphate and evaporated under reduced pressure. Yield: 6.2 g=97%.

$^1$H-NMR DMSO-$d_6$ δ 7.30 (d, 1H), 6.92 (d, 1H), 4.46 (m, 1H), 4.20 (m, 1H), 3.99-3.84 (dd, 2H).

Example 25

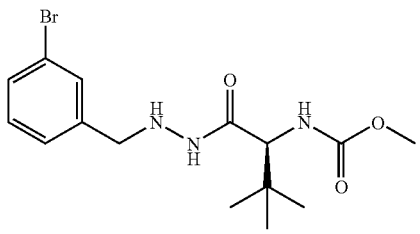

{(1S)-1-[N'-(3-Bromo-benzyl)-hydrazinocarbonyl]-
2,2-dimethyl-propyl}-carbamic acid methyl ester
(25)

N-(Methoxycarbonyl)-(L)-tert-leucine (3.25 g, 17.1 mmol) was dissolved in EtOAc (40 mL) and HOBT (2.55 g, 18.9 mmol), EDAC (3.62 g, 18.9 mmol) and NMM (2.08 mL, 18.9 mmol) were added subsequently. 3-Bromo-benzylhydrazine (4.14 g, 20.6 mmol), dissolved in EtOAc (20 mL) was added to the reaction mixture, which thereafter was stirred at room temperature over night. The organic phase was washed with saturated NaHCO$_3$ (aq., 50 mL), H$_2$O (50 mL) and brine (50 mL). The combined aqueous phases were extracted with EtOAc (3×50 mL). The combined organic phases were dried (Na$_2$SO$_4$), filtered and concentrated under reduced pressure. The crude product was purified by column chromatography (silica, CHCl$_3$/MeOH, 100:0-95:5) to afford 2 (4.88 g, 76%). RP-LC-MS (35 min gradient of 35-80% CH$_3$CN in 0.05% aqueous formic acid) was performed on a small fraction of the residue to obtain a sample of higher purity for characterization and the product was isolated as a white solid.

[α]$_D^{20}$ –28.0° (c 1.2, CH$_3$OH);

$^1$H NMR (CD$_3$OD) δ 7.56 (m, 1H), 7.40 (m, 1H), 7.32 (m, 1H), 7.22 (m, 1H), 3.93 (s, 2H), 3.81 (s, 1H), 3.63 (s, 3H), 0.89 (s, 9H); $^{13}$C NMR (CD$_3$OD) δ 171.7, 159.0, 141.8, 132.9, 131.5, 131.1, 128.8, 123.3, 62.9, 55.5, 52.7, 35.1, 26.9;

MS (m/z 372, M+H$^+$, 374, M+H$^+$).

Example 26

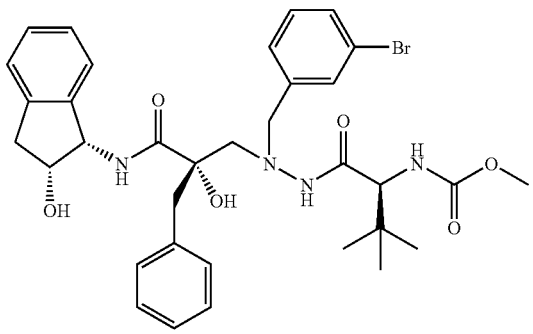

{(1S)-1-[N'-(3-Bromo-benzyl)-N'-[(2S)-2-hydroxy-2-((1S,2R)-2-hydroxy-indan-1-ylcarbamoyl)-3-phenyl-propyl]-hydrazinocarbonyl]-2,2-dimethyl-propyl}-carbamic acid methyl ester (26)

(2S)-2-Benzyl-oxirane-N-[(1S,2R)-2-hydroxy-indan-1-yl]-2-carboxylic acid amide (0.930 g, 3.01 mmol) and compound 25 (1.23 g, 3.31 mmol) were dissolved in dry THF (40 mL), Ti(OiPr)$_4$ (1.79 mL, 6.02 mmol) was added and the mixture was stirred at 40° C. for 2 h. Et$_2$O (100 mL) and saturated NaHCO$_3$ (aq., 100 mL) was added to the reaction mixture and the phases were separated. The organic phase was then washed with H$_2$O (2×200 mL). All water phases were reextracted with CHCl$_3$ (100 mL), and the combined organic phases were dried (Na$_2$SO$_4$), filtered and concentrated under reduced pressure. The crude product was purified by flash chromatography (RP-silica, CH$_3$CN/H$_2$O, 50:50-70:30) affording 3 (0.95 g, 46%) as a light yellow solid.

$[\alpha]_D^9$ −55.2° (c 0.95, CH$_3$OH);

$^1$H NMR (CD$_3$OD) δ 7.50 (m, 1H), 7.36-7.16 (m, 7H), 7.13-6.93 (m, 4H), 6.80 (m, 1H), 4.96 (d, J=4.82 Hz, 1H), 4.17 (d, J=14.7 Hz, 1H), 4.14 (m, 1H), 4.00 (d, J=14.7 Hz, 1H), 3.88 (d, J=13.9 Hz, 1H), 3.60 (m, 4H), 3.07-2.77 (m, 5H), 0.60 (s, 9H); $^{13}$C NMR (CD$_3$OD) δ 177.5, 172.4, 159.0, 142.0, 141.6, 141.4, 137.5, 132.2, 131.6, 131.5, 131.0, 128.9, 128.8, 128.2, 127.71, 127.67, 126.0, 125.5, 123.5, 79.2, 73.8, 68.6, 62.9, 62.0, 58.4, 52.7, 44.3, 40.7, 34.9, 26.6;

MS (m/z 681, M+H$^+$, 683, M+H$^+$).

General Procedures for the Pd-Catalyzed Reactions:

Method A. Aryl bromide 19 or 26, tin reagent, Pd(PPh$_3$)Cl$_2$, CuO and DMF (2 mL) were stirred in a heavy-walled Smith process vial at 130° C. for 20 min in the microwave cavity. CH$_2$Cl$_2$ (30 mL) was added to the mixture followed by washing with saturated NaHCO$_3$ (aq., 3×20 mL). The organic phase was dried (Na$_2$SO$_4$), filtered and evaporated. The residue was redissolved in CH$_3$CN (70 mL) and washed with isohexane (3×20 mL) after which the CH$_3$CN phase was evaporated and the crude product was purified using RP-LC-MS.

Method B. Aryl bromide 19 or 26, boronic acid, Pd(PPh$_3$)Cl$_2$, 2 M Na$_2$CO$_3$ (aq.), EtOH and DME were stirred in a heavy-walled Smith process vial at 120° C. for 30 min in the microwave cavity. Five drops of formic acid were added to the mixture and then the solvent was evaporated. The residue was redissolved in CH$_3$CN/H$_2$O/DMF and filtered before purification by RP-LC-MS.

Method C. Aryl bromide 26, acetylene, Et$_2$NH, Pd(PPh$_3$)$_2$Cl$_2$, CuI and DMF were stirred in a heavy-walled Smith process vial at 140° C. for 30-40 min. Work up was performed by extracting the mixture with CH$_2$Cl$_2$ (2 mL) and H$_2$O (2×2 mL). The organic phase was filtered and evaporated before the product was purified by RP-LC-MS.

Method D. Aryl bromide 19, acetylene, Et$_3$N, Pd(PPh$_3$)$_2$Cl$_2$, CuI and DMF were stirred in a heavy-walled Smith process vial at 130° C. for 60 min. Filtration and evaporation of most of the solvent yielded the crude product which was purified by RP-LC-MS.

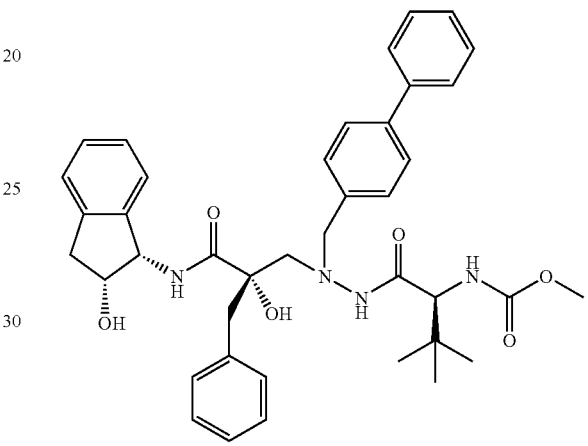

{(1S)-1-[N'-(Biphenyl-4-yl-methyl)-N'-[(2S)-2-hydroxy-2-((1S,2R)-2-hydroxy-indan-1-ylcarbamoyl)-3-phenyl-propyl]-hydrazinocarbonyl]-2,2-dimethyl-propyl}-carbamic acid methyl ester (27)

The title compound was prepared according to Method B, using compound 19 (90.0 mg, 0.132 mmol), phenylboronic acid (80.5 mg, 0.660 mmol), Pd(PPh$_3$)$_3$Cl$_2$ (4.60 mg, 0.0065 mmol), 2 M Na$_2$CO$_3$ (aq., 0.198 mL, 0.396 mmol), EtOH (0.6 mL) and DME (2.4 mL). Purification by RP-LC-MS (40 min gradient of 10-100% CH$_3$CN in 0.05% aqueous formic acid) afforded the product (33.7 mg, 38%) as a white solid.

$[\alpha]_D^{20}$ −59.3° (c 1.4, CHCl$_3$);

$^1$H NMR (CD$_3$OD/CDCl$_3$, 1:1) δ 7.55-7.16 (m, 14H), 7.13-6.92 (m, 3H), 6.82 (m, 1H), 5.05 (d, J=4.80 Hz, 1H), 4.24 (d, J=14.3 Hz, 1H), 4.09 (m, 1H), 4.05 (d, J=14.3 Hz, 1H), 3.92 (d, J=14.0 Hz, 1H), 3.58 (m, 4H), 3.04-2.71 (m, 5H), 0.56 (s, 9H); $^{13}$C NMR (CD$_3$OD/CDCl$_3$, 1:1) δ 176.2, 171.3, 157.9, 141.5, 141.0, 140.6, 140.5, 136.81, 136.78, 131.0, 129.3, 129.2, 128.4, 128.3, 127.6, 127.4, 127.3, 127.2, 127.1, 125.4, 124.8, 78.5, 73.3, 67.6, 61.9, 61.7, 57.8, 52.6, 43.8, 39.6, 34.6, 26.2;

MS (m/z 679, M+H$^+$).

Example 28

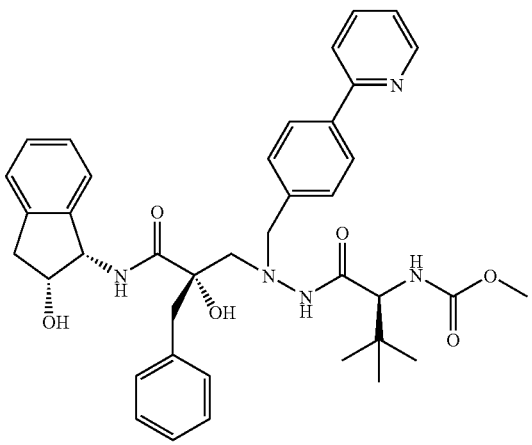

{(1S)-1-[N'-[(2S)-2-Hydroxy-2-((1S,2R)-2-hydroxy-indan-1-ylcarbamoyl)-3-phenyl-propyl]-N'-[4-(pyridin-2-yl)-benzyl]-hydrazinocarbonyl]-2,2-dimethyl-propyl}-carbamic acid methyl ester (28)

The title compound was prepared according to Method A, using compound 19 (100 mg, 0.147 mmol), 2-(1,1,1-tributylstannyl)pyridine (220 mg, 0.598 mmol), Pd(PPh)$_3$Cl$_2$ (5.12 mg, 0.0072 mmol) and CuO (11.7 mg, 0.147 mmol). Purification by RP-LC-MS (40 min gradient of 10-100% CH$_3$CN in 0.05% aqueous formic acid) gave the product (17.2 mg, 17%) as a white solid.

$[\alpha]_D^{19}$ −28.8° (c 0.99, CH$_3$OH);

$^1$H NMR (CD$_3$OD) δ 8.57 (m, 1H), 7.94-6.93 (m, 15H), 6.75 (m, 1H), 4.99 (m, 1H), 4.27 (d, J=14.3 Hz, 1H), 4.14 (m, 1H), 4.12 (d, J=14.3 Hz, 1H), 3.90 (d, J=14.9, 1H), 3.68-3.52 (m, 4H), 3.08-2.74 (m, 5H), 0.59 (s, 9H); $^{13}$C NMR (CD$_3$OD) δ 176.4, 171, 2, 157.8, 157.5, 149.1, 140.9, 140.2, 138.9, 138.3, 137.7, 136.4, 130.5, 128.9, 127.7, 127.6, 126.8, 126.5, 126.4, 124.8, 124.5, 122.5, 121.2, 78.1, 72.7, 67.2, 61.8, 61.3, 57.3, 51.5, 43.2, 39.6, 33.7, 25.4; HRMS (M+H$^+$): 680.3450, C$_{39}$H$_{46}$N$_5$O$_6$ required 680.3448.

Example 29

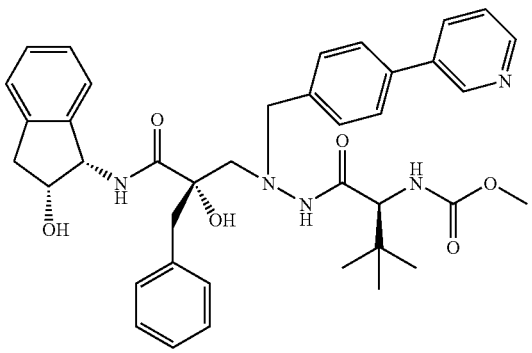

{(1S)-1-[N'-[(2S)-2-Hydroxy-2-((1S,2R)-2-hydroxy-indan-1-ylcarbamoyl)-3-phenyl-propyl]-N'-[4-(pyridin-3-yl)-benzyl]-hydrazinocarbonyl]-2,2-dimethyl-propyl}-carbamic acid methyl ester (29)

The title compound was prepared according to Method A, using compound 19 (90.0 mg, 0.132 mmol), 3-(1,1,1-tributylstannyl)pyridine (194 mg, 0.527 mmol), Pd(PPh)$_3$Cl$_2$ (4.63 mg, 0.0065 mmol) and CuO (10.5 mg, 0.132 mmol). The product (24.0 mg, 27%) was afforded as a white solid after purification by RP-LC-MS (40 min gradient of 10-100% CH$_3$CN in 0.05% aqueous formic acid).

$[\alpha]_D^{19}$ −37.5° (c 1.4, CH$_3$OH);

$^1$H NMR (CD$_3$OD) δ 8.70 (m, 1H), 8.49 (m 1H), 7.99 (m, 1H), 7.56-7.42 (m, 5H), 7.34-7.18 (m, 5H), 7.15-6.94 (m, 3H), 6.72 (m, 1H), 4.99 (m, 1H), 4.27 (d, J=14.5 Hz, 1H), 4.13 (m, 1H), 4.11 (d, J=14.5 Hz, 1H), 3.91 (m, 1H), 3.66-3.53 (m, 4H), 3.07-2.76 (m, 5H), 0.59 (s, 9H); $^{13}$C NMR (CD$_3$OD) δ 176.4, 171, 2, 157.8, 147.5, 147.0, 140.9, 140.3, 138.2, 137.3, 136.5, 136.4, 135.2, 130.5, 129.3, 127.7, 127.6, 126.8, 126.5, 126.2, 124.8, 124.5, 124.3, 78.1, 72.6, 67.2, 61.7, 61.2, 57.3, 51.5, 43.2, 39.6, 33.7, 25.4;

HRMS (M+H$^+$): 680.3465, C$_{39}$H$_{46}$N$_5$O$_6$ required 680.3448.

Example 30

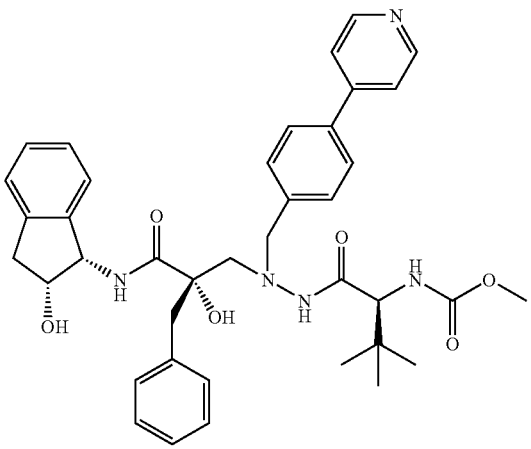

{(1S)-1-[N'-[(2S)-2-Hydroxy-2-((1S,2R)-2-hydroxy-indan-1-ylcarbamoyl)-3-phenyl-propyl]-N'-[4-(pyridin-4-yl)-benzyl]-hydrazinocarbonyl]-2,2-dimethyl-propyl}-carbamic acid methyl ester (30)

The title compound was prepared according to Method B, using compound 19 (90.0 mg, 0.132 mmol), pyridine-4-boronic acid (81.0 mg, 0.659 mmol), Pd(PPh)$_3$Cl$_2$ (4.60 mg, 0.0065 mmol), 2 M Na$_2$CO$_3$ (aq., 0.198 mL, 0.396 mmol), EtOH (0.4 mL) and DME (1.6 mL). Purification by RP-LC- MS (40 min gradient of 0-80% CH$_3$CN in 0.05% aqueous formic acid) yielded the product (15.6 mg, 17%) as a white solid.

$[\alpha]_D^{20}$ −41.5° (c 0.47, CH$_3$OH);

$^1$H NMR (CD$_3$OD) δ 8.55 (m, 2H), 7.68-6.91 (m, 14H), 6.70 (m, 1H), 4.97 (d, J=5.15, 1H), 4.26 (d, J=14.6 Hz, 1H), 4.14 (m, 1H), 4.12 (d, J=14.6 Hz, 1H), 3.90 (m, 1H), 3.64-3.51 (m, 4H), 3.07-2.75 (m, 5H), 0.58 (s, 9H); $^{13}$C NMR (CD$_3$OD) δ 176.4, 171, 2, 157.8, 149.4, 149.3, 140.9, 140.3, 139.4, 136.7, 136.4, 130.4, 129.3, 127.7, 127.6, 126.8, 126.5, 126.2, 124.8, 124.5, 121.8, 78.1, 72.6, 67.3, 61.7, 61.2, 57.3, 51.5, 43.2, 39.6, 33.7, 25.4; HRMS (M+H$^+$): 680.3432, C$_{39}$H$_{46}$N$_5$O$_6$ required 680.3448.

Example 31

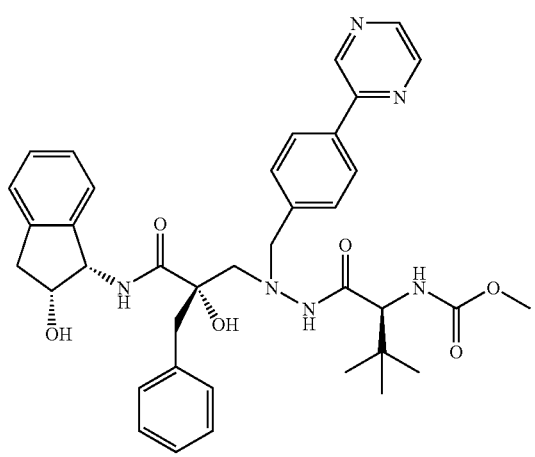

{(1S)-1-[N'-[(2S)-2-Hydroxy-2-((1S,2R)-2-hydroxy-indan-1-ylcarbamoyl)-3-phenyl-propyl]-N'-[4-(pyrazin-2-yl)-benzyl]-hydrazinocarbonyl]-2,2-dimethyl-propyl}-carbamic acid methyl ester (31)

The title compound was prepared according to Method A, using compound 19 (91.3 mg, 0.134 mmol), 2-(1,1,1-tributylstannyl)pyrazine (198 mg, 0.537 mmol), Pd(PPh$_3$)$_3$Cl$_2$ (4.70 mg, 0.0067 mmol) and CuO (10.7 mg, 0.134 mmol). Purification by RP-LC-MS (35 min gradient of 20-90% CH$_3$CN in 0.05% aqueous formic acid) yielded the product (17.3 mg, 19%) as a white solid.

$[\alpha]_D^{20}$ −26.5 (c 0.87, MeOH);

$^1$H NMR (CD$_3$OD) δ 9.00 (m, 1H), 8.65 (m, 1H), 8.49 (m, 1H), 7.88 (m, 2H), 7.47 (m, 2H), 7.34-6.91 (m, 8H), 6.72 (m, 1H), 4.97 (d, J=5.00, 1H), 4.27 (d, J=14.5 Hz, 1H), 4.14 (d, J=14.5 Hz, 1H), 4.13 (m, 1H), 3.90 (d, 1H), 3.63 (s, 1H), 3.57 (s, 3H), 3.05-2.77 (m, 5H), 0.59 (s, 9H); $^{13}$C NMR (CD$_3$OD) δ 177.5, 172.4 159.0, 154.1, 145.7, 143.9, 142.9, 142.1, 141.4, 141.2, 137.6, 136.6, 131.6, 130.3, 128.9, 128.8, 127.9, 127.7, 127.5, 126.0, 125.7, 79.3, 73.8, 68.4, 62.9, 62.5, 58.5, 52.7, 44.4, 40.8, 34.9, 26.6; HRMS (M+H$^+$): 681.3385, C$_{38}$H$_{44}$N$_6$O$_6$ requires 681.3401.

Example 32

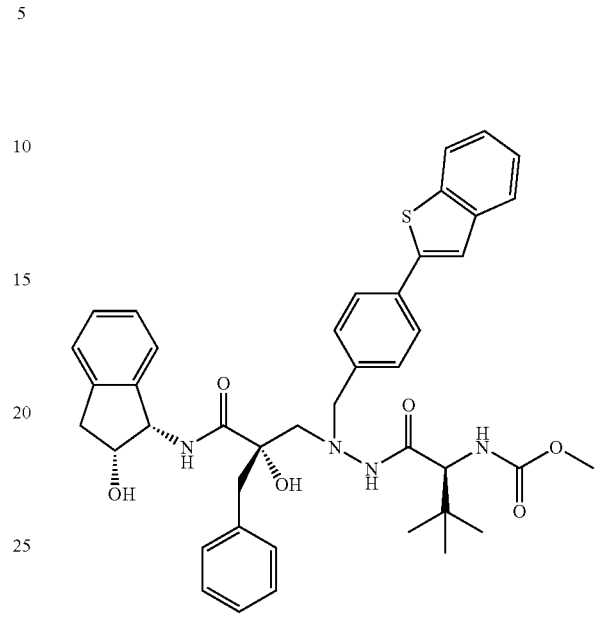

{(1S)-1-[N'-[(2S)-2-Hydroxy-2-((1S,2R)-2-hydroxy-indan-1-ylcarbamoyl)-3-phenyl-propyl]-N'-[4-(benzo[b]thiophen-2-yl)-benzyl]-hydrazinocarbonyl]-2,2-dimethyl-propyl}-carbamic acid methyl ester (32)

The title compound was prepared according to Method B, using 19 (83.4 mg, 0.123 mmol), benzo[b]thiophene-2-boronic acid (109 mg, 0.613 mmol), Pd(PPh$_3$)$_3$Cl$_2$ (4.32 mg, 0.00615 mmol), 2 M Na$_2$CO$_3$ (aq., 0.185 mL, 0.369 mmol), EtOH (0.4 mL) and DME (1.6 mL). Purification by RP-LC-MS (35 min gradient of 20-100% CH$_3$CN in 0.05% aqueous formic acid) afforded the product (56.4 mg, 62%) as a white solid.

$[\alpha]_D^{19}$ −68.5° (c 1.0, CHCl$_3$);

$^1$H NMR (CD$_3$OD/CDCl$_3$ 2:1) δ 7.82-7.67 (m, 3H), 7.58-7.06 (m, 11H), 7.10 (m, 1H), 7.03 (m, 1H), 6.95 (m, 1H), 6.80 (m, 1H), 4.96 (d, J=5.04 Hz, 1H), 4.17 (d, J=14.5 Hz, 1H), 4.06 (m, 1H), 4.01 (d, J=14.5 Hz, 1H), 3.85 (d, J=13.9 Hz, 1H), 3.55 (s, 1H), 3.53 (s, 3H), 3.05-2.72 (m, 5H), 0.53 (s, 9H); $^{13}$C NMR (DMSO-d$_6$, 60° C. due to presence of rotamers at room temperature) δ 174.4, 169.8, 156.1, 143.2, 141.8, 140.3, 140.1, 138.3, 138.2, 136.3, 132.0, 130.0, 128.6, 127.3, 126.8, 125.8, 125.6, 125.3, 124.4, 124.2, 123.9, 123.3, 122.1, 119.3, 119.2, 77.3, 71.6, 66.7, 61.1, 60.4, 56.4, 56.3, 51.1, 42.7, 33.2, 25.9; MS (m/z 735, M+H$^+$).

Example 33

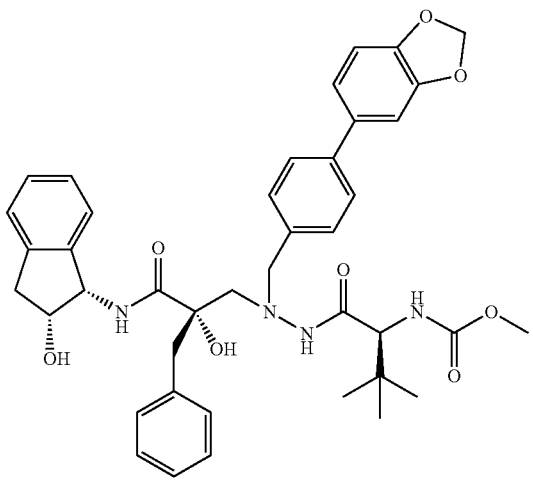

{(1S)-1-[N'-(4-Benzo[1,3]dioxol-5-yl-benzyl)-N'-[(2S)-2-hydroxy-2-((1S,2R)-2-hydroxy-indan-1-ylcarbamoyl)-3-phenyl-propyl]-hydrazinocarbonyl]-2,2-dimethyl-propyl}-carbamic acid methyl ester (33)

The title compound was prepared according to Method B, using compound 19 (91.9 mg, 0.135 mmol), 3,4-methylenedioxyphenylboronic acid (112 mg, 0.676 mmol), Pd(PPh)$_3$Cl$_2$ (4.70 mg, 0.0067 mmol), 2 M Na$_2$CO$_3$ (aq., 0.203 mL, 0.405 mmol), EtOH (0.4 mL) and DME (1.6 mL). Purification by RP-LC-MS (35 min gradient of 30-100% CH$_3$CN in 0.05% aqueous formic acid) afforded the product (47.7 mg, 49%) as a white solid.

$[\alpha]_D^{19}$ –62.3° (c 0.65, CHCl$_3$);

$^1$H NMR (CD$_3$OD/CDCl$_3$ 2:1) δ 7.36-7.15 (m, 9H), 7.12-6.90 (m, 5H), 6.85-6.73 (m, 2H), 5.93 (s, 2H), 5.01 (d, J=4.88 Hz, 1H), 4.22 (d, J=14.2 Hz, 1H), 4.10 (m, 1H), 4.04 (d, J=14.2 Hz, 1H), 3.90 (d, J=13.8 Hz, 1H), 3.58 (m, 4H), 3.07-2.72 (m, 5H), 0.56 (s, 9H); $^{13}$C NMR (CD$_3$OD/CDCl$_3$ 3:2) δ 176.7, 176.6, 171.6, 158.2, 148.9, 147.9, 141.02, 141.00, 140.9, 140.7, 136.9, 136.7, 136.1, 131.2, 129.5, 128.50, 128.46, 127.29, 127.25, 125.6, 125.1, 109.1, 107.9, 101.9, 78.7, 73.5, 67.8, 62.0, 58.05, 57.96, 52.7, 43.9, 40.0, 34.7, 26.3; MS (m/z 723, M+H$^+$).

Example 34

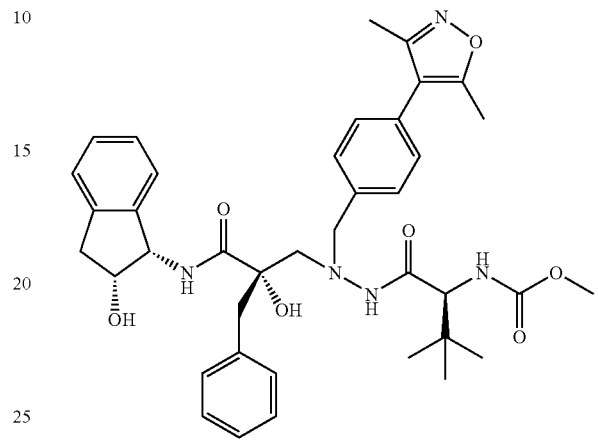

{(1S)-1-[N'-[4-(3,5-Dimethyl-isoxazol-4-yl)-benzyl]-N'-[(2S)-2-hydroxy-2-((1S,2R)-2-hydroxy-indan-1-ylcarbamoyl)-3-phenyl-propyl]-hydrazinocarbonyl]-2,2-dimethyl-propyl}-carbamic acid methyl ester (34)

The title compound was prepared according to Method B, using compound 19 (95.1 mg, 0.139 mmol), 3,5-dimethyl-isoxazole-4-boronic acid (98.5 mg, 0.699 mmol), Pd(PPh)$_3$Cl$_2$ (4.84 mg, 0.0069 mmol), 2 M Na$_2$CO$_3$ (aq., 0.210 mL, 0.419 mmol), EtOH (0.4 mL) and DME (1.6 mL). Purification by RP-LC-MS (35 min gradient of 20-90% CH$_3$CN in 0.05% aqueous formic acid) afforded the product (30.2 mg, 31%) as a white solid.

$[\alpha]_D^{20}$ –53.5° (c 0.72, CHCl$_3$);

$^1$H NMR (CD$_3$OD) δ 7.42 (m, 2H), 7.34-7.16 (m, 5H), 7.15-6.96 (m, 5H), 6.71 (m, 1H), 4.97 (d, J=5.11 Hz, 1H), 4.27 (d, J=14.5 Hz, 1H), 4.13 (m, 1H), 4.08 (d, J=14.5 Hz, 3.93 (d, J=13.9 Hz, 1H), 3.63 (s, 1H), 3.60 (s, 3H), 3.09-2.76 (m, 5H), 2.34 (s, 3H), 2.18 (s, 3H), 0.58 (s, 9H); $^{13}$C NMR (CD$_3$OD) δ 177.6, 172.3, 166.8, 159.9, 159.0, 142.2, 141.5, 138.7, 137.5, 131.6, 130.4, 130.13, 130.10, 128.9, 128.7, 127.7, 127.4, 126.0, 125.7, 117.8, 79.3, 73.8, 68.5, 62.9, 62.4, 58.5, 52.7, 44.3, 40.8, 34.9, 26.7, 11.4, 10.7; MS (m/z 698, M+H$^+$).

Example 35

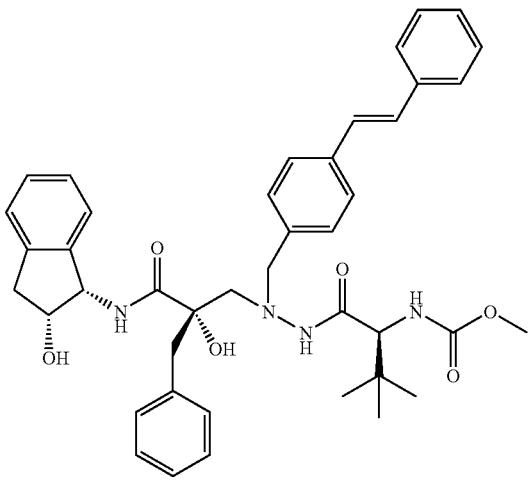

((1S)-1-{N'-[(2S)-2-Hydroxy-2-((1S,2R)-2-hydroxy-indan-1-ylcarbamoyl)-3-phenyl-propyl]-N'-[4-((E)-styryl)-benzyl]-hydrazinocarbonyl}-2,2-dimethyl-propyl)-carbamic acid methyl ester (35)

Compound 35 was prepared according to Method B, using compound 19 (89.5 mg, 0.132 mmol), trans-phenylethenyboronic acid (97.3 mg, 0.658 mmol), Pd(PPh$_3$)$_3$Cl$_2$ (4.56 mg, 0.0065 mmol), 2 M Na$_2$CO$_3$ (aq., 0.197 mL, 0.395 mmol), EtOH (0.4 mL) and DME (1.6 mL). Purification by RP-LC-MS (35 min gradient of 20-90% CH$_3$CN in 0.05% aqueous formic acid) afforded the product (54.4 mg, 59%) as a white solid.

[α]$_D^{20}$ −68.0° (c 0.81, CHCl$_3$);
$^1$H NMR (CD$_3$OD/CDCl$_3$ 2:1) δ 7.48 (m, 2H), 7.39-6.91 (m, 17H), 6.81 (m, 1H), 5.01 (d, J=4.97 Hz, 1H), 4.20 (d, J=14.5 Hz, 1H), 4.11 (m, 1H), 4.03 (d, J=14.5 Hz, 1H), 3.88 (d, J=14.0 Hz, 1H), 3.63 (s, 1H), 3.59 (s, 3H), 3.05-2.74 (m, 5H), 0.59 (s, 9H); $^{13}$C NMR (CD$_3$OD/CDCl$_3$ 2:1) δ 176.9, 171.8, 158.4, 141.3, 140.9, 138.2, 137.7, 137.6, 137.1, 131.3, 129.5, 129.4, 129.1, 129.0, 128.61, 128.56, 128.3, 127.4, 127.2, 127.1, 125.7, 125.2, 78.8, 73.6, 67.9, 62.4, 62.3, 58.1, 52.7, 44.1, 40.3, 34.7, 26.4; MS (m/z 705, M+H$^+$).

Example 36

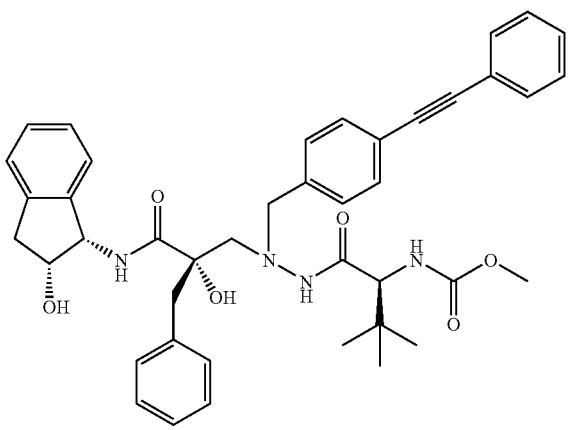

{(1S)-1-[N'-[(2S)-2-Hydroxy-2-((1S,2R)-2-hydroxy-indan-1-ylcarbamoyl)-3-phenyl-propyl]-N'-(4-phenylethynyl-benzyl)-hydrazinocarbonyl]-2,2-dimethyl-propyl}-carbamic acid methyl ester (36)

Compound 36 was prepared according to Method D, using compound 19 (88.4 mg, 0.130 mmol), phenylacetylene (0.0285 mL, 0.260 mmol), Et$_3$N (0.181 mL, 1.30 mmol), Pd(PPh$_3$)$_2$Cl$_2$ (4.49 mg, 0.0064 mmol), CuI (2.46 mg, 0.0129 mmol) and DMF (2.1 mL). RP-LC-MS (35 min gradient of 40-100% CH$_3$CN in 0.05% aqueous formic acid) afforded the title compound (20.4 mg, 22%) as a white solid.

[α]$_D^{19}$ −58.0° (c 1.3, CHCl$_3$);
$^1$H NMR (CD$_3$OD) δ 7.59-7.04 (m, 16H), 6.95 (m, 1H), 6.81 (m, 1H), 4.98 (d, J=4.97 Hz, 1H), 4.22 (d, J=14.5, 1H), 4.14 (m, 1H), 4.07 (d, J=14.5, 1H), 3.89 (d, J=14.0, 1H), 3.63 (s, 1H), 3.61 (s, 3H), 3.07-2.77 (m, 5H), 0.62 (s, 9H); $^{13}$C NMR (CD$_3$OD/CDCl$_3$ 2:1) δ 176.7, 171.7, 162.2, 141.1, 140.8, 138.5, 137.0, 132.17, 132.16, 132.07, 131.2, 129.1, 129.0, 128.9, 128.6, 128.5, 127.3, 125.6, 125.0, 124.0, 123.1, 89.7 (2 C), 78.6, 73.5, 68.0, 62.2, 62.1, 58.0, 52.7, 44.0, 40.1, 34.7, 26.4; MS (m/z 703, M+H$^+$).

Example 37

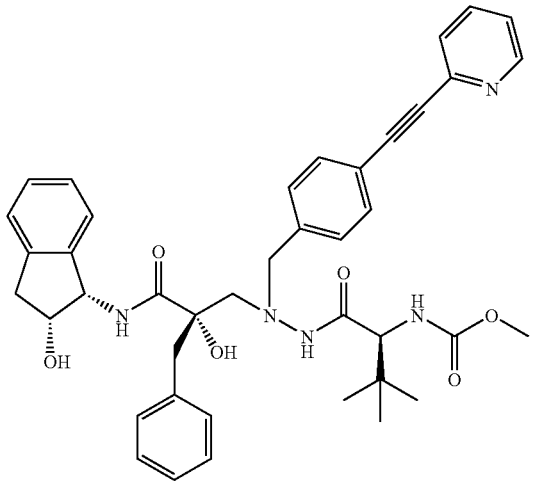

{(1S)-1-[N'-[(2S)-2-Hydroxy-2-((1S,2R)-2-hydroxy-indan-1-ylcarbamoyl)-3-phenyl-propyl]-N-(4-pyridin-2-ylethynyl-benzyl)-hydrazinocarbonyl]-2,2-dimethyl-propyl}-carbamic acid methyl ester (37)

Compound 37 was prepared according to Method D, using compound 19 (92.7 mg, 0.136 mmol), 2-(ethynyl)pyridine (0.0280 mL, 0.272 mmol), Et$_3$N (0.190 mL, 1.36 mmol), Pd(PPh$_3$)$_2$Cl$_2$ (4.80 mg, 0.0068 mmol), CuI (2.60 mg, 0.0136 mmol) and DMF (2.1 mL). RP-LC-MS (35 min gradient of 20-100% CH$_3$CN in 0.05% aqueous formic acid) afforded the title compound (34.2 mg, 34%) as a white solid.

[α]$_D^{19}$ −25.0° (c 0.56, CH$_3$OH);
$^1$H NMR (CD$_3$OD) δ 8.52 (m, 1H), 7.85 (m, 1H), 7.62 (m, 1H), 7.46-6.90 (m, 13H), 6.78 (m, 1H), 4.97 (d, J=5.10 Hz, 1H), 4.23 (d, J=14.8 Hz, 1H), 4.12 (m, 1H), 4.10 (d, J=14.8 Hz, 1H), 3.89 (d, J=14.1 Hz, 1H), 3.62 (s, 1H). 3.59 (s, 3H), 3.08-2.76 (m, 5H), 0.60 (s, 9H); $^{13}$C NMR (CD$_3$OD) δ 177.5, 172.4, 159.0, 150.6, 144.0, 142.1, 141.4, 140.7, 138.7, 137.5, 132.9, 131.6, 129.8, 128.92, 128.88, 128.7, 127.7, 126.1, 125.7, 124.7, 122.1, 90.7, 88.7, 79.3, 73.8, 68.5, 62.9, 62.5, 58.5, 52.7, 44.3, 40.8, 34.9, 26.6; MS (m/z 704, M+H$^+$).

Example 38

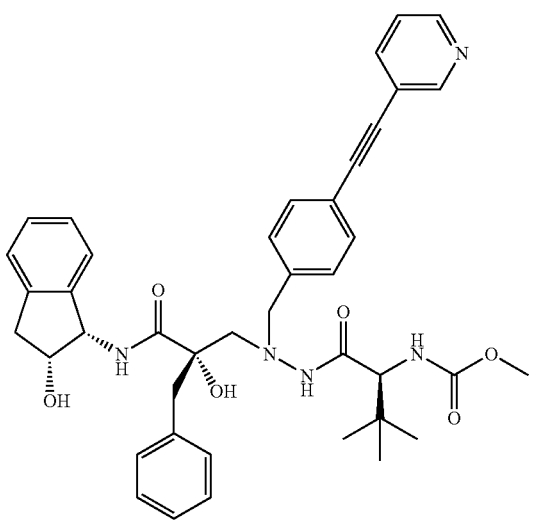

{(1S)-1-[N'-[(2S)-2-Hydroxy-2-((1S,2R)-2-hydroxy-indan-1-ylcarbamoyl)-3-phenyl-propyl]-N'-(4-pyridin-3-ylethynyl-benzyl)-hydrazinocarbonyl]-2,2-dimethyl-propyl}-carbamic acid methyl ester (38)

Compound 38 was prepared according to Method D, using compound 19 (85.8 mg, 0.126 mmol), 3-(ethynyl)pyridine (0.0260 mL, 0.252 mmol), Et$_3$N (0.176 mL, 1.26 mmol), Pd(PPh$_3$)$_2$Cl$_2$ (4.42 mg, 0.0063 mmol), CuI (2.40 mg, 0.0126 mmol) and DMF (2.1 mL). RP-LC-MS (35 min gradient of 25-100% CH$_3$CN in 0.05% aqueous formic acid) afforded the title compound (40.3 mg, 45%) as a white solid.

$[\alpha]_D^{18}$ −24.2° (c 0.94, CH$_3$OH);
$^1$H NMR (CD$_3$OD) δ 8.69 (m, 1H), 8.50 (m, 1H), 7.96 (m, 1H), 7.59-6.89 (m, 13H), 6.79 (m, 1H), 4.98 (d, J=5.05 Hz, 1H), 4.24 (d, J=14.6 Hz, 1H), 4.12 (m, 1H), 4.09 (d, J=14.6 Hz, 1H), 3.90 (d, J=14.1 Hz, 1H), 3.63 (s, 1H), 3.60 (s, 3H), 3.08-2.73 (m, 5H), 0.61 (s, 9H); $^{13}$C NMR (CD$_3$OD) δ 177.5, 172.4, 159.0, 152.4, 149.1, 142.1, 141.4, 140.5, 140.3, 137.5, 132.6, 131.6, 129.8, 128.92, 128.86, 127.7, 127.5, 126.1, 125.6, 122.6, 93.9, 86.1, 79.3, 73.8, 68.5, 62.9, 62.5, 58.4, 52.7, 44.4, 40.8, 34.9, 26.6 (two aromatic carbon signals overlapping with other signals); MS (m/z 704, M+H$^+$).

Example 39

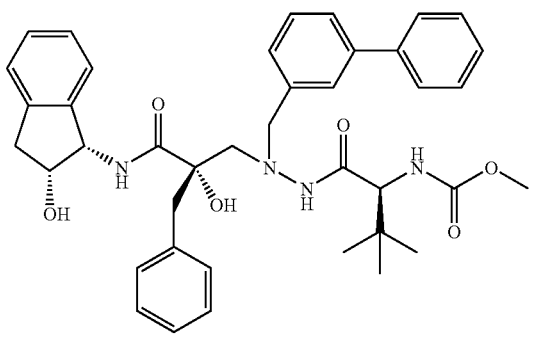

{(1S)-1-[N'-(Biphenyl-3-yl-methyl)-N'-[(2S)-2-hydroxy-2-((1S,2R)-2-hydroxy-indan-1-ylcarbamoyl)-3-phenyl-propyl]-hydrazinocarbonyl]-2,2-dimethyl-propyl}-carbamic acid methyl ester (39)

The title compound was prepared according to Method B using compound 26 (80.5 mg, 0.118 mmol), phenylboronic acid (72.5 mg, 0.595 mmol), Pd(PPh$_3$)$_2$Cl$_2$ (6.50 mg, 0.00926 mmol), 2 M Na$_2$CO$_3$ (aq., 0.177 mL, 0.354 mmol), DME (1.6 mL) and EtOH (0.4 mL) affording the product (21.2 mg, 26%) after RP-LC-MS (35 min gradient of 40-100% CH$_3$CN in 0.05% aqueous formic acid) as a white solid.

$[\alpha]_D^{19}$ −88.0° (c 0.96, CHCl$_3$);
$^1$H NMR (CD$_3$OD/CDCl$_3$, 4:1) δ 7.62 (m, 1H), 7.52-7.17 (m, 14H), 7.04-6.87 (m, 2H), 6.53 (m, 1H), 5.00 (d, J=4.68 Hz, 1H), 4.28 (d, J=14.45 Hz, 1H), 4.10 (m, 1H), 4.06 (d, J=14.5 Hz, 1H), 3.93 (d, J=14.1 Hz, 1H), 3.58 (m, 4H), 3.03-2.70 (m, 15H), 0.52 (s, 9H); $^{13}$C NMR (CD$_3$OD/CDCl$_3$, 4:1) δ 176.9, 171.8, 158.4, 142.1, 141.8, 141.1, 140.8, 138.7, 137.1, 131.3, 129.4, 128.6, 128.4, 128.1, 127.9, 127.77, 127.76, 127.72, 127.42, 127.41, 126.9, 125.6, 125.0, 78.7, 73.5, 68.1, 62.4, 62.3, 58.1, 52.7, 44.1, 40.1, 34.7, 26.4; MS (m/z 680, M+H$^+$).

Example 40

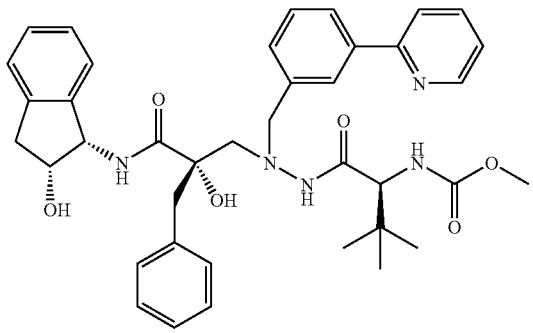

{(1S)-1-[N'-[(2S)-2-Hydroxy-2-((1S,2R)-2-hydroxy-indan-1-ylcarbamoyl)-3-phenyl-propyl]-N'-[3-(pyridin-2-yl)-benzyl)]-hydrazinocarbonyl]-2,2-dimethyl-propyl}-carbamic acid methyl ester (40)

The title compound was synthesized according to Method A using compound 26 (80.2 mg, 0.118 mmol), 2-(1,1,1-tributylstannyl)-pyridine (174 mg, 0.474 mmol), Pd(PPh$_3$)$_2$Cl$_2$ (4.50 mg, 0.00641 mmol), CuO (10.5 mg, 0.132 mmol) and DMF (2 mL). RP-LC-MS (35 min gradient of 20-80% CH$_3$CN in 0.05% aqueous formic acid) afforded the product (14.1 mg, 18%) as a white solid.

$[\alpha]_D^{19}$ −59.6° (c 0.94, CHCl$_3$);
$^1$H NMR (CD$_3$OD/CDCl$_3$, 1:1) δ 8.53 (m, 1H), 7.84 (m, 1H), 7.79-7.59 (m, 3H), 7.40-7.17 (m, 8H), 7.01 (m, 1H), 6.92

(m, 2H), 6.58 (m, 1H), 5.00 (d, J=5.08 Hz, 1H), 4.27 (d, J=14.5 Hz, 1H), 4.12 (d, J=14.5, 1H), 4.10 (m, 1H), 3.94 (d, J=14.1 Hz, 1H), 3.60 (s, 1H), 3.58 (s, 3H), 3.03-2.71 (m, 5H), 0.51 (s, 9H); $^{13}$C NMR (CD$_3$OD/CDCl$_3$, 1:1) δ 176.6, 171.7, 158.1, 149.5, 141.0, 140.7, 139.7, 138.7, 138.3, 137.0, 132.6, 131.2, 129.8, 129.5, 128.5, 128.3, 127.7, 127.3, 127.2, 126.9, 125.4, 124.9, 123.1, 122.4, 78.5, 73.4, 67.8, 62.11, 62.08, 57.9, 52.6, 43.9, 40.0, 34.6, 26.3; HRMS (M+H$^+$): 680.3428, C$_{39}$H$_{46}$N$_5$O$_6$ requires 680.3448.

Example 41

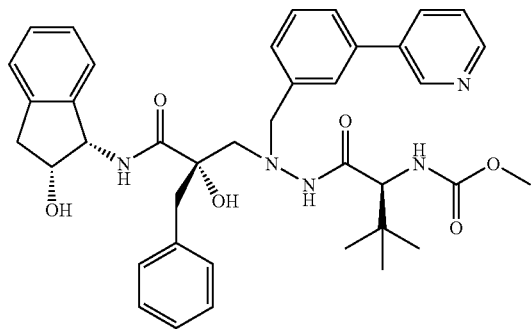

{(1S)-1-[N'-[(2S)-2-Hydroxy-2-((1S,2R)-2-hydroxy-indan-1-ylcarbamoyl)-3-phenyl-propyl]-N'-[3-(pyridin-3-yl)-benzyl)]-hydrazinocarbonyl]-2,2-dimethyl-propyl}-carbamic acid methyl ester (41)

The title compound was synthesized from compound 26 (79.1 mg, 0.116 mmol), 3-(1,1,1-tributylstannyl)-pyridine (175 mg, 0.476 mmol), Pd(PPh$_3$)$_2$Cl$_2$ (4.10 mg, 0.00584 mmol) and CuO (11.0 mg, 0.138 mmol) and DMF (2 mL) as described in Method A. The product (19.7 mg, 25%) was obtained after purification by RP-LC-MS (35 min gradient of 10-85% CH$_3$CN in 0.05% aqueous formic acid) as a white solid.

[α]$_D^{19}$ –72.8° (c 1.13, CHCl$_3$);

$^1$H NMR (CD$_3$OD/CDCl$_3$, 1:1) δ 8.58 (m, 1H), 8.40 (m, 1H), 7.83 (m, 2H), 7.67-7.16 (m, 9H), 6.98 (m, 1H), 6.85 (m, 2H), 6.45 (m, 1H), 4.96 (d, J=5.08 Hz, 1H), 4.29 (d, J=14.5 Hz, 1H), 4.10 (d, J=14.5, 1H), 4.08 (m, 1H), 3.95 (d, J=14.1 Hz, 1H), 3.58 (m, 4H), 3.03-2.71 (m, 5H), 0.48 (s, 9H); $^{13}$C NMR (CD$_3$OD/CDCl$_3$, 1:1) δ 176.9, 171.8, 158.3, 148.0, 147.9, 141.3, 140.8, 139.4, 138.0, 137.0, 136.1 (two carbons according to ghsqc), 131.2, 129.8, 129.1, 128.6, 128.3, 127.9, 127.4, 127.1, 126.7, 125.5, 125.0, 124.9, 78.8, 73.3, 68.1, 62.24, 62.21, 58.0, 52.7, 44.0, 40.2, 34.6, 26.3; HRMS (M+H$^+$): 680.3458, C$_{39}$H$_{46}$N$_5$O$_6$ requires 680.3448.

Example 42

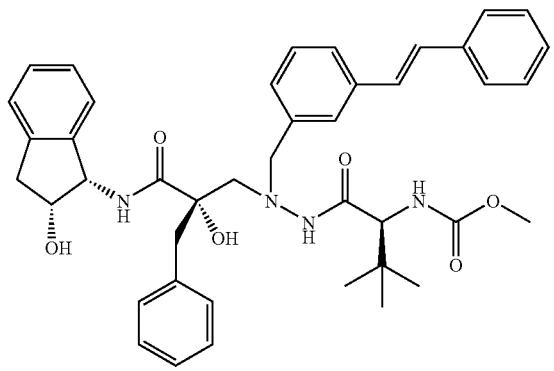

((1S)-1-{N'-[(2S)-2-Hydroxy-2-((1S,2R)-2-hydroxy-indan-1-ylcarbamoyl)-3-phenyl-propyl]-N'-[3-((E)-styryl)-benzyl]-hydrazinocarbonyl}-2,2-dimethyl-propyl)-carbamic acid methyl ester (42)

Synthesis of the title compound was performed according to Method B using compound 26 (80.0 mg, 0.117 mmol), trans-phenylethenyboronic acid (86.9 g, 0.587 mmol), Pd(PPh$_3$)$_2$Cl$_2$ (6.90 g, 0.00983 mmol), 2 M Na$_2$CO$_3$ (aq., 0.176 mL, 0.352 mmol), DME (1.6 mL) and EtOH (0.4 mL). RP-LC-MS (35 min gradient of 0-80% CH$_3$CN in 0.05% aqueous formic acid) afforded the product (39.7 mg, 48%) as a white solid.

[α]$_D^{18}$ –71.0° (c 1.17, CHCl$_3$);

$^1$H NMR (CD$_3$OD/CDCl$_3$, 5:2) δ 7.53 (m, 1H), 7.46-7.13 (m, 14H), 7.10-6.93 (m, 4H), 6.75 (m, 1H), 5.00 (d, J=4.69 Hz, 1H), 4.24 (d, J=14.5 Hz, 1H), 4.11 (m, 1H), 4.05 (d, J=14.5 Hz, 1H), 3.96 (d, J=14.1 Hz, 1H), 3.60 (m, 4H), 3.04-2.75 (m, 5H), 0.58 (s, 9H); $^{13}$C NMR (CD$_3$OD/CDCl$_3$, 5:2) δ 176.7, 171.7, 158.3, 141.0, 140.8, 138.5, 138.3, 138.1, 137.0, 131.3, 129.5, 129.23, 129.19, 129.1, 128.6, 128.5, 128.3, 128.1, 127.6, 127.4, 127.2, 127.1, 126.2, 125.5, 125.0, 73.5, 68.1, 62.3, 62.2, 58.0, 52.7, 44.0, 40.1, 34.7, 26.4 (one aliphatic carbon signal overlapping with other signal);

MS (m/z 706 μM+H$^+$).

Example 43

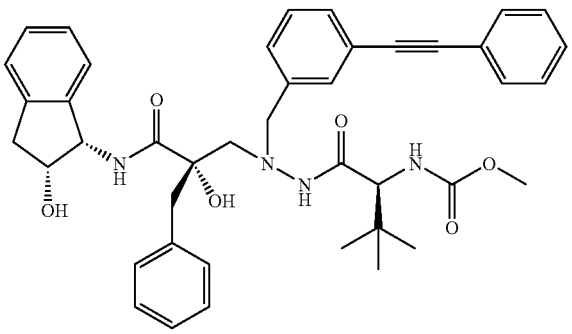

{(1S)-1-[N'-[(2S)-2-Hydroxy-2-((1S,2R)-2-hydroxy-indan-1-ylcarbamoyl)-3-phenyl-propyl]-N'-(3-phenylethynyl-benzyl)-hydrazinocarbonyl]-2,2-dimethyl-propyl}-carbamic acid methyl ester (43)

Method C was followed using compound 26 (79.2 mg, 0.116 mmol), phenylacetylene (0.0150 mL, 0.139 mmol), Et$_2$NH (0.110 mL, 1.01 mmol), Pd(PPh$_3$)$_2$Cl$_2$ (6.10 g, 0.00869 mmol), CuI (1.90 mg, 0.00998 mmol) and DMF (2 mL). RP-LC-MS (35 min gradient of 20-90% CH$_3$CN in 0.05% aqueous formic acid) afforded the title compound (22.2 mg, 27%) as a white solid.

$[\alpha]_D^{18}$ −96.6° (c 0.87, CHCl$_3$);

$^1$H NMR (CD$_3$OD/CDCl$_3$, 3:1) δ 7.49 (m, 1H), 7.45-7.14 (m, 13H), 7.08 (m, 1H), 7.00 (m, 2H), 6.83 (m, 1H), 5.01 (d, J=4.68 Hz, 1H), 4.22 (d, J=14.5 Hz, 1H), 4.13 (m, 1H), 4.04 (d, J=14.5 Hz, 1H), 3.91 (d, J=14.1 Hz, 1H), 3.61 (m, 4H), 3.05-2.78 (m, 5H), 0.61 (s, 9H); $^{13}$C NMR (CD$_3$OD/CDCl$_3$, 3:1) δ 177.1, 172.0, 158.6, 141.4, 140.9, 138.9, 137.2, 132.3, 132.0, 131.40, 131.38, 129.24, 129.18, 129.16, 129.1, 128.7, 128.6, 127.7, 127.5, 125.8, 125.3, 124.4, 124.3, 90.01, 90.03, 78.9, 73.6, 68.4, 62.5, 62.1, 58.1, 52.7, 44.1, 40.4, 34.8, 26.5; MS (m/z 704, M+H$^+$).

Example 44

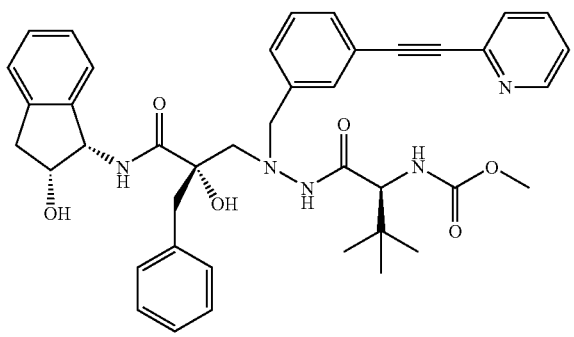

{(1S)-1-[N'-[(2S)-2-Hydroxy-2-((1S,2R)-2-hydroxy-indan-1-ylcarbamoyl)-3-phenyl-propyl]-N'-[3-(pyridin-2-ylethynyl)-benzyl]-hydrazinocarbonyl]-2,2-dimethyl-propyl}-carbamic acid methyl ester (44)

The title compound was synthesized according to Method C using compound 26 (79.4 mg, 0.117 mmol), 2-(ethynyl)pyridine (15.3 mg, 0.148 mmol), Et$_2$NH (0.105 mL, 1.01 mmol) Pd(PPh$_3$)$_2$Cl$_2$ (6.50 mg, 0.00926 mmol), CuI (1.50 mg, 0.00788 mmol) and DMF (2 mL). RP-LC-MS (35 min gradient of 0-100% CH$_3$CN in 0.05% aqueous formic acid) gave the product (15.9 mg, 19%) as a white solid.

$[\alpha]_D^{19}$ −367° (c 0.60, CHCl$_3$);

$^1$H NMR (CD$_3$OD/CDCl$_3$, 1:1) δ 8.48 (m, 1H), 7.73 (m, 1H), 7.56-7.15 (m, 1H), 7.08-6.92 (m, 3H), 6.82 (m, 1H), 5.01 (d, J=4.68 Hz, 1H), 4.19 (d, J=14.7 Hz, 1H), 4.09 (m, 1H), 4.02 (d, J=14.7 Hz, 1H), 3.92 (d, J=14.1 Hz, 1H), 3.60 (s, 3H), 3.59 (s, 1H), 3.00-2.74 (m, 5H), 0.59 (s, 9H); $^{13}$C NMR (CD$_3$OD/CDCl$_3$, 1:1) δ 176.3, 171.4, 158.0, 149.8, 143.4, 140.7, 140.5, 138.6, 137.6, 136.8, 132.2, 131.6, 131.8, 129.8, 129.0, 128.4, 128.3, 128.1, 127.3, 127.2, 125.4, 124.8, 123.8, 122.6, 90.4, 88.4, 78.6, 73.4, 68.0, 61.9, 61.6, 57.8, 52.7, 43.8, 39.7, 34.6, 26.2;

HRMS (M+H$^+$): 704.3438, C$_{41}$H$_{46}$N$_5$O$_6$ required 704.3448.

Example 45

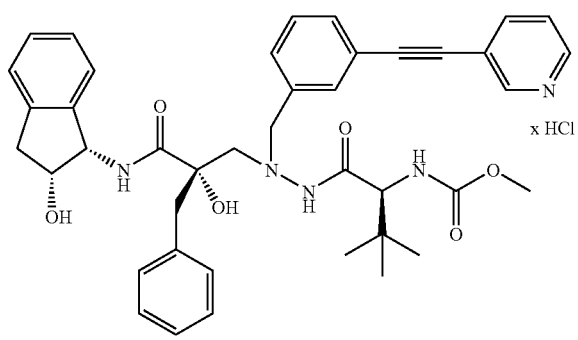

{(1S)-1-[N'-[(2S)-2-Hydroxy-2-((1S,2R)-2-hydroxy-indan-1-ylcarbamoyl)-3-phenyl-propyl]-N'-[3-(pyridin-3-ylethynyl)-benzyl]-hydrazinocarbonyl]-2,2-dimethyl-propyl}-carbamic acid methyl ester hydrochloride (45)

The title compound was synthesized according to Method C using compound 26 (89.5 mg, 0.131 mmol), 3-(ethynyl)pyridine (16.3 mg, 0.158 mmol), Et$_2$NH (0.118 mL, 1.14 mmol), Pd(PPh$_3$)$_2$Cl$_2$ (7.70 mg, 0.0110 mmol), CuI (1.80, 0.00945 mmol) and DMF (2 mL). The crude product was purified by RP-LC-MS (35 min gradient of 10-85% CH$_3$CN in 0.05% aqueous formic acid). The HCl-salt of the product was made by dissolving the product in CH$_2$Cl$_2$ followed by addition of HCl in ether until all product had precipitated. After evaporation the salt was dissolved in CH$_3$CN and H$_2$O, and subsequently freeze dried which gave the title compound (21.6 mg, 23%) as a white solid.

$[\alpha]D^{19}$ −65.7° (c 1.15, CHCl$_3$);

$^1$H NMR (CD$_3$OD/CDCl$_3$, 9:1) δ 8.25 (m, 1H), 7.61 (m, 1H), 7.52-7.17 (m, 11H), 7.10-6.91 (m, 3H), 6.74 (m, 1H), 5.00 (d, J=5.07 Hz, 1H), 4.23 (d, J=14.5 Hz, 1H), 4.14 (m, 1H), 4.08 (d, J=14.5 Hz, 1H), 3.93 (d, J=13.7 Hz, 1H), 3.62 (s, 1H), 3.60 (s, 3H), 3.05-2.77 (m, 5H), 0.59 (m, 9H); $^{13}$C NMR (DMSO-d$_6$) δ 174.6, 170.1, 156.5, 149.8, 147.2, 142.1, 140.5, 140.4, 138.7, 136.4, 130.9, 130.2, 130.1, 129.1, 128.3, 127.6, 127.0, 126.2, 125.9, 124.7, 124.0, 121.1, (2 aromatic carbon signals overlapping with other signals), 93.4, 85.1, 79.2, 77.5, 71.8, 67.6, 61.3, 60.7, 56.4, 51.5, 42.9, 33.5, 26.1;

HRMS (M+H$^+$): 704.3468, C$_{41}$H$_{46}$N$_5$O$_6$ required 704.3448.

Example 46

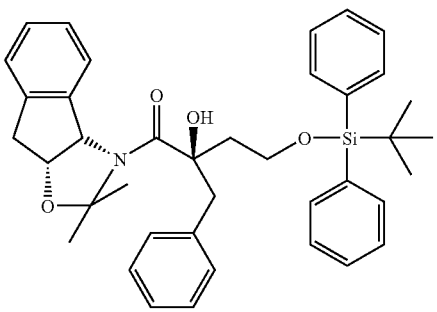

(R)-2-Benzyl-4-(tert-butyl-diphenyl-silanyloxy)-1-((3aS,8aR)-2,2-dimethyl-8,8a-dihydro-3 aH-indeno[1,2-d]oxazol-3-yl)-2-hydroxybutan-1-one (46)

To a cooled (0° C.) solution of (R)-2-benzyl-4-(tert-butyl-diphenyl-silanyloxy)-2-hydroxy-N-((1S,2R)-2-hydroxy-indan-1-yl)-butyramide (22) (0.4 g, 0.69 mmol) and pyridinium p-toluenesulphonic acid (15 mg, 0.059 mmol) in dry dichloromethane (25 mL), 2-methoxypropene (0.5 g, 6.9 mmol) was added and stirred for 6 h at the same temperature. Saturated NaHCO$_3$ solution was added and the organic layer was washed with sat. NaHCO$_3$, brine, dried over anhydrous MgSO$_4$ and evaporated under reduced pressure. The title compound (0.325 g) was used without further purification in the next step.

MS (ESI$^+$): 620 (M$^+$).

Example 47

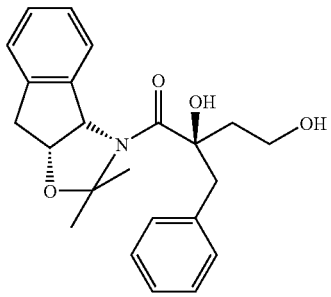

(R)-2-Benzyl-1-((3aS,8aR)-2,2-dimethyl-8,8a-dihydro-3aH-indeno[1,2-d]oxazol-3-yl)-2,4-dihydroxy-butan-1-one (47)

TBAF (0.274 g, 1.05 mmol, 1M in THF) was added to a solution of (R)-2-benzyl-4-(tert-butyl-diphenyl-silanyloxy)-1-((3aS,8aR)-2,2-dimethyl-8,8a-dihydro-3 aH-indeno[1,2-d]oxazol-3-yl)-2-hydroxy-butan-1-one (46) (0.325 g, 0.52 mmol) in THF (20 mL) at room temperature and stirred for 3 h. The solvent was evaporated and the residue dissolved in dichloromethane and washed with water and brine, dried and evaporated. The product was purified by flash chromatography using petroleum ether:acetone (4:1) which gave 0.140 g of the title compound in 53% yield from two steps.

MS (ESI$^+$): m/z: 382 (M$^+$+1);

$^1$H NMR (CD$_3$OD, 400 MHz): δ 7.62 (m, 1H), 7.34-7.28 (m, 5H), 7.16-7.12 (m, 3H), 5.20 (m, 1H), 4.02 (m, 1H), 3.91-3.85 (m, 2H), 3.12 (d, J=13.20 Hz, 1H), 2.98 (d, J=13.20 Hz, 1H), 2.82-2.68 (m, 2H), 2.58 (m, 1H), 2.00 (m, 1H), 1.56 (s, 3H), 1.13 (s, 3H); $^{13}$C NMR (CD$_3$OD, 100 MHz): δ 171.6, 142.4, 140.5, 136.6, 131.0, 127.8, 127.4, 126.8, 126.4, 126.2, 124.7, 98.0, 80.7, 79.6, 67.2, 59.0, 43.1, 35.1, 25.7, 23.9.

Example 48

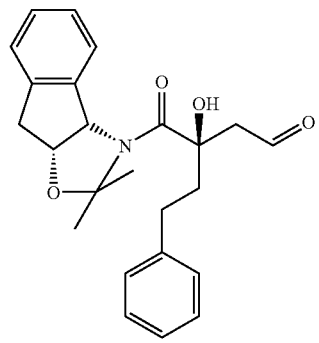

(R)-3-Benzyl-4-((3aS,8aR)-2,2-dimethyl-8,8a-dihydro-3 aH-indeno[1,2-d]oxazol-3-yl)-3-hydroxy-4-oxo-butyraldehyde (48)

A solution of (R)-2-benzyl-1-((3aS,8aR)-2,2-dimethyl-8,8a-dihydro-3 aH-indeno[1,2-d]oxazol-3-yl)-2,4-dihydroxybutan-1-one (47) (0.12 g, 0.31 mmol) in dry CH$_2$Cl$_2$ (5 mL) was added over 1 min to a stirred solution of Dess-Martin periodinate (0.146 g, 0.35 mmol) in dry CH$_2$Cl$_2$ (10 mL). After 30 min the homogeneous mixture was diluted with ether and poured into cold saturated NaHCO$_3$ (10 mL) containing Na$_2$S$_2$O$_3$ (2.2 g). The organic layer was washed with aqueous saturated NaHCO$_3$, brine and dried (MgSO$_4$). The solvents were evaporated below 20° C. to give the title compound (0.086 g, 72%). The residue was immediately used for the next step.

MS (ESI$^+$): 380 (M$^+$+1).

Example 49

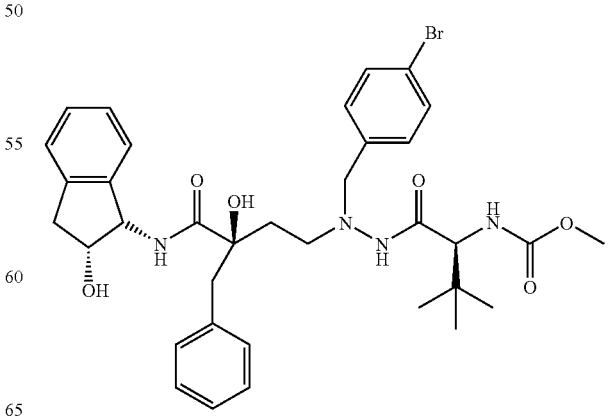

((S)-1-{N'-(4-Bromo-benzyl)-N'-[(R)-3-hydroxy-3-((1S,2R)-2-hydroxy-indan-1-ylcarbamoyl)-4-phenyl-butyl]-hydrazinocarbonyl}-2,2-dimethyl-propyl)-carbamic acid methyl ester (49)

Method B: (R)-3-Benzyl-4-((3aS,8aR)-2,2-dimethyl-8,8a-dihydro-3aH-indeno[1,2-d]oxazol-3-yl)-3-hydroxy-4-oxo-butyraldehyde (48) (0.086 g, 0.23 mmol) and {(S)-1-[N'-(4-Bromo-benzyl)-hydrazinocarbonyl]-2,2-dimethyl-propyl}-carbamic acid methyl ester (0.084 g, 0.23 mmol) in dry THF (10.0 mL) was added acetic acid (0.027 g, 0.45 mmol) and stirred for 10 min and then Na(OAc)₃BH (0.144 g, 0.68 mmol) was added and stirred overnight. The reaction mixture was quenched with water and evaporated. The residue was dissolved in dichloromethane (20.0 mL) and washed with water, brine and trifluoroacetic acid (1.0 mL) was added and stirred the organic layer for 20 min. The mixture was evaporated and washed successively with aqueous NaHCO₃, water, brine and dried. The product was purified on silica gel flash chromatography using acetone:pet.ether (1:3) to yield 0.057 g (36%) of the title compound.

MS (ESI⁺): m/z: 695, 697 (M⁺);

¹H NMR (CDCl₃, 400 MHz): δ 7.40-7.24 (m, 11H), 7.20-7.10 (m, 2H), 7.00 (m, 1H), 6.24 (m, 1H), 5.18 (m, 1H), 4.42 (m, 1H), 3.85 (s, 1H), 3.66 (s, 3H), 3.12-2.82 (m, 6H), 2.62 (s, 1H), 2.20 (m, 1H), 1.90 (m, 1H), 0.88 (s, 9H); ¹³C NMR (CD₃OD, 100 MHz): δ 176.2, 171.1, 159.0, 140.7, 140.2, 136.8, 131.5, 130.7, 127.8, 127.5, 124.7, 124.0, 121.2, 79.4, 73.1, 61.7, 57.0, 54.8, 51.6, 45.9, 39.5, 34.5, 33.4, 28.3, 25.6.

Example 50

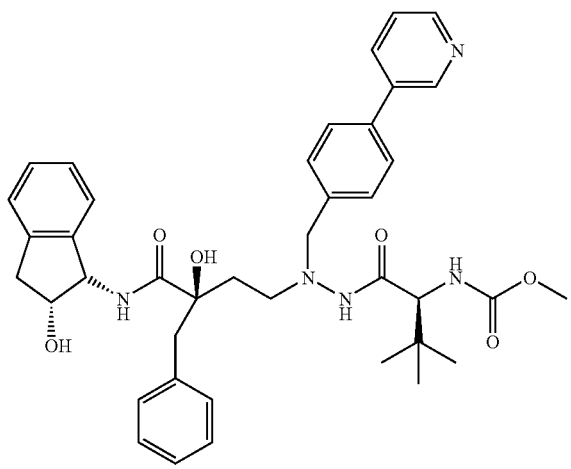

{(S)-1-[N'-[(S)-3-Hydroxy-3-((1S,2R)-2-hydroxy-indan-1-ylcarbamoyl)-4-phenyl-butyl]-N'-(4-pyridin-3-yl-benzyl)-hydrazinocarbonyl]-2,2-dimethyl-propyl}-carbamic acid methyl ester (50)

Pd(PPh₃)₂Cl₂ (3.84 mg, 0.0054 mmol) was added to a solution of ((S)-1-{N-(4-Bromo-benzyl)-N'-[(S)-3-hydroxy-3-((1S,2R)-2-hydroxy-indan-1-ylcarbamoyl)-4-phenyl-butyl]-hydrazinocarbonyl}-2,2-dimethyl-propyl)-carbamic acid methyl ester (22) (75 mg, 0.108 mmol), 3-(1,1,1-tri-n-butylstannyl)pyridine (159 mg, 0.431 mmol) and CuO (8.6 mg, 0.108 mmol) in DMF (2.0 mL) and stirred in a heavy-walled Smith process vial at 120° C. 50 min in the microwave cavity. The mixture was diluted with CH₂Cl₂ (20.0 mL) and washed with aq. saturated NaHCO₃ (3×15.0 mL). The organic layer was dried (MgSO₄) and evaporated. The residue was re-dissolved in CH₃CN (50.0 mL) and washed with iso-hexane (3×20.0 mL). The acetonitrile phase was evaporated and the crude product was purified using RP-LC-MS (45 min gradient of 15-70% CH₃CN in 0.05% aqueous formic acid) which gave the title product (23.1 mg, 31%) as a white solid.

MS (ESI⁺): m/z: 694 (M⁺);

¹H NMR (CD₃OD 400 MHz): δ 8.66 (m, 1H), 8.45 (m, 1H), 8.00 (m, 1H), 7.52-7.44 (m, 6H), 7.30-7.04 (m, 9H), 5.04 (m, 1H), 4.24 (m, 1H), 3.82 (m, 2H), 3.68 (s, 1H), 3.60 (s, 3H), 3.10-2.78 (m, 6H), 2.62 (s, 1H), 2.20 (m, 1H), 1.96 (m, 1H), 0.78 (s, 9H); ¹³C NMR (CD₃OD, 100 MHz): δ 176.9, 171.1, 157.8, 147.8, 147.0, 141.3, 140.3, 137.0, 136.8, 135.2, 130.5, 130.0, 127.6, 126.8, 126.5, 126.3, 124.9, 124.1, 78.7, 72.5, 61.9, 61.7, 57.2, 53.6, 51.5, 39.6, 34.3, 33.5, 28.3, 25.7

Example 51

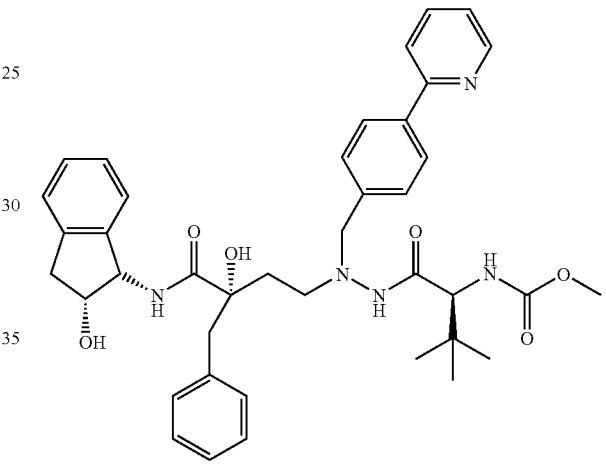

{(S)-1-[N'-[(S)-3-Hydroxy-3-((1S,2R)-2-hydroxy-indan-1-ylcarbamoyl)-4-phenyl-butyl]-N'-(4-pyridin-2-yl-benzyl)-hydrazinocarbonyl]-2,2-dimethyl-propyl}-carbamic acid methyl ester (51)

Pd(PPh₃)₂Cl₂ (4.61 mg, 0.0065 mmol) was added to a solution of ((S)-1-{N'-(4-Bromo-benzyl)-N'-[(S)-3-hydroxy-3-((1S,2R)-2-hydroxy-indan-1-ylcarbamoyl)-4-phenyl-butyl]-hydrazinocarbonyl}-2,2-dimethyl-propyl)-carbamic acid methyl ester (22) (90 mg, 0.129 mmol), 2-(1,1,1-tri-n-butylstannyl)pyridine (191 mg, 0.51 mmol) and CuO (10.3 mg, 0.129 mmol) in DMF (2.0 mL) and stirred in a heavy-walled Smith process vial at 120° C. 50 min in the microwave cavity. The mixture was diluted with CH₂Cl₂ (25.0 mL) and washed with aq. saturated NaHCO₃ (3×15.0 mL) The organic layer was dried (MgSO₄) and evaporated. The residue was re-dissolved in CH₃CN (60.0 mL) and washed with isohexane (3×20.0 mL). The acetonitrile phase was evaporated and the crude product was purified using RP-LC-MS (45 min gradient of 15-70% CH₃CN in 0.05% aqueous formic acid) which gave the title product (36.2 mg, 40%) as a white solid.

MS (ESI⁺): m/z: 694 (M⁺);

¹H NMR (CD₃OD 400 MHz): δ 8.56 (m, 1H), 7.82 (m, 1H), 7.72-7.60 (m, 4H), 7.54 (m, 1H), 7.44 (m, 1H), 7.34-7.16

(m, 6H), 7.06-7.00 (m, 3H), 6.96 (m, 1H), 4.96 (m, 1H), 4.16 (m, 1H), 3.82 (m, 2H), 3.70 (m, 1H), 3.60 (s, 3H), 3.08-2.78 (m, 6H), 2.10 (m, 1H), 1.94 (m, 1H), 0.78 (s, 9H); $^{13}$C NMR (CD$_3$OD, 100 MHz): δ 176.9, 171.5, 158.2, 157.7, 149.1, 141.5, 140.5, 138.6, 138.1, 138.0, 137.2, 132.9, 132.3, 132.2, 130.8, 129.9, 129.2, 129.1, 127.9, 127.3, 126.9, 126.6, 125.0, 124.5, 122.8, 121.7, 79.3, 73.1, 62.3, 57.7, 53.6, 51.9, 46.6, 39.8, 34.5, 33.9, 26.1.

Example 52

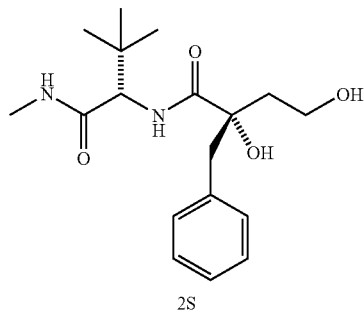

2S

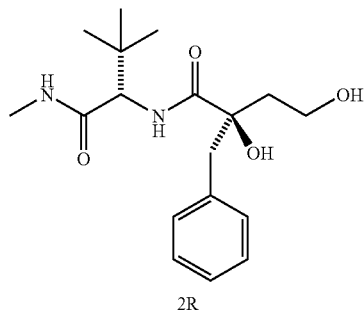

2R (2S)-2-Benzyl-N-((1S)-2,2-dimethyl-1-methylcarbamoyl-propyl)-2,4-dihydroxy-butyramide (52S)

3-Benzyl-3-hydroxy-dihydro-furan-2-one (21c) (0.961 g, 5.00 mmol), H-tLeu-NHMe (1.80 g, 12.5 mmol) and 2-pyridone (0.476 g, 5.0 mmol) was suspended in 10 mL 1,2-dichloroethane in a reaction tube. The vessel was sealed with a screw cap and heated in a metal heating block at 80° C. for 24 h. The solvent was evaporated and the residue was re-dissolved in the least amount of 25% acetonitrile in water and the mixture was purified and the diastereomers separated by column chromatography using RP(C-18)-silica and a manual 10-50% acetonitrile in water gradient (with 0.05% HCOOH). The resulting fractions were analyzed by analytical RP-LC-MS and pure fractions pooled together and the solvent was evaporated to give (2S)-2-Benzyl-N-((1S)-2,2-dimethyl-1-methylcarbamoyl-propyl)-2,4-dihydroxy-butyramide (0.424 g, 25%) and (2R)-2-Benzyl-N-((1S)-2,2-dimethyl-1-methyl-carbamoyl-propyl)-2,4-dihydroxy-butyramide (0.631 g, 38%).

MS (ESI$^+$): m/z 337 (M+H)$^+$;

$^1$H NMR (CD$_3$OD, 400 MHz): δ 7.20-7.14 (m, 5H), 4.05 (s, 1H), 3.82-3.68 (m, 2H), 3.03 (d, J=13.4 Hz, 1H), 2.85 (d, J=13.4 Hz, 1H), 2.85 (s, 3H), 2.29-2.21 (m, 2H), 1.98-1.89 (m, 2H), 0.93 (s, 9H). $^{13}$C NMR (CD$_3$OD, 100.5 MHz): δ 176.2, 172.2, 137.3, 131.3, 128.8, 127.4, 79.6, 61.5, 59.6, 47.1, 41.7, 35.7, 27.0, 26.0.

Example 53

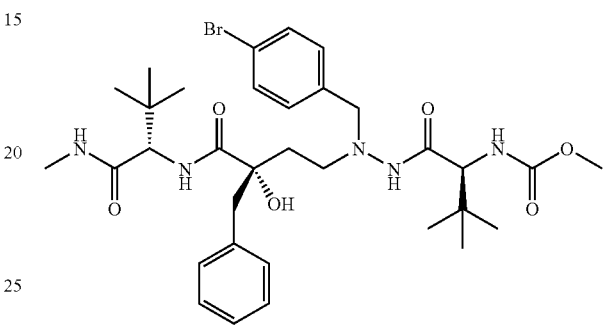

(1-{N'-(4-Bromobenzyl)-N'-[3-(2,2-dimethyl-1-methylcarbamoyl-propylcarbamoyl)-3-hydroxy-4-phenyl-butyl]-hydrazinocarbonyl}2,2-dimethylpropyl) carbamic acid methyl ester (53)

A mixture of (2S)-2-Benzyl-N-((1S)-2,2-dimethyl-1-methylcarbamoyl-propyl)-2,4-dihydroxy-butyramide (52S) (0.337 g, 1.00 mmol), IBX (0.560 g, 2.0 mmol) and 10 mL 1,2-dichloroethane in a reaction vial sealed with a screw cap was heated at 80° C. for 2 h. The resulting suspension was transferred to a 20 mL syringe and filtered through a syringe filter into a solution of hydrazide (9) (0.372 g, 1.00 mmol) in 15 mL DCE in a flame dried 50 mL round-bottom flask equipped with a septum. To this was added acetic acid (0.12 mL 2.0 mmol), mixture was stirred for 10 min and then sodium triacetoxyborohydride (0.636 g, 3.0 mmol) was added. The septum-sealed flask was flushed with nitrogen and the reaction was stirred at room temperature for 24 h. The reaction was quenched by addition of water and volatiles were evaporated. The residue was dissolved in 50% MeCN/water and purified by preparative RP-LC-MS (repeated 1 mL injections) to give 0.191 g of the title compound (28% yield).

MS (ESI$^+$): m/z 690, 692 (M+H)$^+$ $^1$H NMR (CD$_3$OD, 400 MHz): δ 7.47 (AA' of AA'XX' system, 2H), 7.33 (XX' of AA'XX' system, 2H), 7.19-7.16 (m, 5H), 4.02 (s, 1H), 3.85 (s, 2H), 3.75 (s, 1H), 3.68 (s, 3H), 3.04-2.87 (m, 3H), 2.77 (d, J=13.2 Hz, 1H), 2.61 (s, 3H), 2.23-2.13 (m, 1H), 2.02-1.90 (m, 1H), 0.89 (s, 9H), 0.80 (s, 9H).

$^{13}$C NMR (CD$_3$OD, 100.5 MHz): δ 176.5, 172.3, 172.1, 158.9, 137.5, 137.2, 132.3, 131.4, 128.7, 127.3, 122.4, 79.7, 63.0, 62.4, 61.5, 54.8, 52.8, 47.1, 35.7, 35.6, 34.7, 27.1, 26.9, 26.0.

Example 54

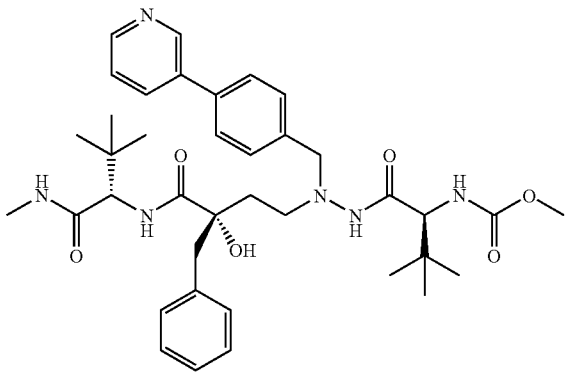

{1-[N'-(3-(2,2-Dimethyl-1-methylcarbamoyl-propyl-carbamoyl)-3-hydroxy-4-phenyl-butyl]-N'-(4-pyridin-3-yl-benzyl)-hydrazinocarbonyl]-2,2-dimethyl-propyl}carbamic acid methyl ester (54)

A mixture of compound (53) (69 mg, 0.10 mmol), 3-pyridylboronic acid (37 mg, 0.30 mmol), Pd(OAc)₂ (1.1 mg, 0.0050 mmol), [(t-Bu)₃PH]BF₄ (3.0 mg, 0.010 mmol) and K₂CO₃ (41.5 mg, 0.30 mmol), H₂O (0.30 mL) and 1,2-dimethoxyethane (1.0 mL) in a 2.0 mL microwave vial was irradiated to 80° C. for 20 min. The reaction mixture was filtered through celite and the solvent evaporated under reduced pressure. The residue was purified by preparative RP-LC-MS which gave 30.1 mg of the title compound (44% yield) as a colorless solid.

MS (ESI⁺): m/z 690 (M+H)⁺

¹H NMR (CD₃OD, 400 MHz): δ 8.78 (m, 1H), 8.54 (m, 1H), 8.07 (m, 1H), 7.65-7.51 (m, 5H), 7.27-7.15 (m, 5H), 4.03-3.89 (m, 3H), 3.77 (s, 1H), 3.62 (s, 3H), 3.08-2.92 (m, 3H), 2.76 (d, J=13.2 Hz, 1H), 2.61 (s, 3H), 2.24-2.15 (m, 1H), 2.04-1.93 (m, 1H), 0.89 (s, 9H), 0.79 (s, 9H). ¹³C NMR (CD₃OD, 100.5 MHz): δ 176.6, 172.3, 172.1, 159.0, 148.7, 148.2, 138.4, 138.3, 137.9, 137.6, 136.6, 136.5, 131.4, 128.7, 128.1, 127.3, 125.5, 79.8, 63.1, 62.9, 61.6, 54.8, 52.7, 47.0, 35.7, 35.6, 34.8, 27.1, 26.9, 26.0.

Example 55

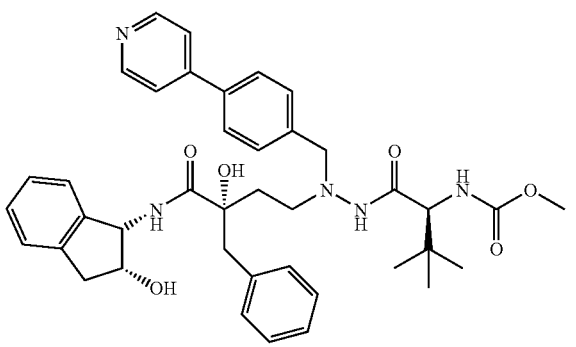

{1-[N'-[3-Hydroxy-3-(2-hydroxy-indan-1-ylcarbamoyl)-4-phenyl-butyl]-N'-(4-pyridin-3-yl-benzyl)-hydrazinocarbonyl]-2,2-dimethyl-propyl}-carbamic acid methyl ester (55)

Pd(PPh₃)₂Cl₂ (5.05 mg, 0.0072 mmol) was added to a solution of ((S)-1-{N'-(4-Bromo-benzyl)-N'-[(S)-3-hydroxy-3-((1S,2R)-2-hydroxy-indan-1-ylcarbamoyl)-4-phenyl-butyl]-hydrazinocarbonyl}-2,2-dimethyl-propyl)-carbamic acid methyl ester (12) (100 mg, 0.143 mmol), pyridine-4-boronic acid (71.0 mg, 0.575 mmol), 2 M aq.Na₂CO₃ (0.215 mL, 0.432 mmol), EtOH (0.4 mL) and DME (1.6 mL) and stirred in a heavy-walled Smith process vial at 120° C. for 30 min in the microwave cavity. Five drops of formic acid were added to the mixture and then the solvent was evaporated. The crude product was purified using RP-LC-MS (40 min gradient of 15-85% CH₃CN in 0.05% aqueous formic acid) yielded the product (35.3 mg, 35%) as a white solid MS (ESI⁺): m/z: 694 (M⁺)

¹H NMR (CD₃OD 400 MHz): δ 8.52 (m, 2H), 7.57 (m, 4H), 7.46 (m, 2H), 7.29-7.02 (m, 9H), 5.04 (d, J=14.6 Hz, 1H), 4.23 (m, 1H), 3.81 (m, 2H), 3.65 (m, 1H), 3.58 (s, 3H), 3.07-2.78 (m, 6H), 2.20 (m, 1H), 1.94 (m, 1H), 0.69 (s, 9H).

Example 56

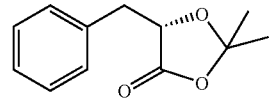

(S)-5-Benzyl-2,2-dimethyl-[1,3]dioxolan-4-one (56)

A solution of (S)-2-Hydroxy-3-phenyl-propionic acid (1.662 g, 10.0 mmol), 2,2-dimethoxypropane (8.328 g, 80.0 mmol) and PPTSA (1.257 g, 5.0 mmol) in chloroform was stirred at 70° C. for one hour, concentrated, dissolved in dichloromethane and purified on silica gel with 10% EtOAc-PE which gave the title compound (2.010 g, 97%) as a white solid.

¹H NMR (CDCl₃, 400 MHz) δ 1.37 (s, 3H), 1.50 (s, 3H), 3.05 (dd, J=14.4, 6.4 Hz, 1H), 3.20 (dd, J=14.4, 4.4 Hz, 1H), 4.66 (dd, J=6.4, 4.4 Hz, 1H), 7.20-7.40 (m, 5H); ¹³C NMR (CDCl₃, 100 MHz) δ 26.4, 27.2, 37.9, 75.3, 111.1, 127.3, 128.6, 130.1, 136.0, 172.7.

Example 57

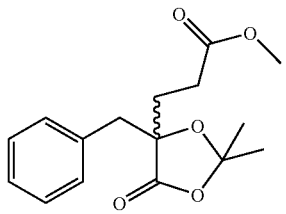

3-(4-Benzyl-2,2-dimethyl-5-oxo-[1,3]dioxolan-4-yl)-propionic acid methyl ester (57)

To a solution of compound 56 (3.180 g, 15.42 mmol) in THF was added 9.42 mL LDA (1.8 M in THF, 16.96 mmol) at −78° C. Methyl acrylate (1.460 g, 16.96 mmol) was added to the solution at −78° C. after 15 min. After 1 h the reaction was quenched with saturated NH₄Cl aqueous solution, extracted with EtOAc 3×30 mL, dried with MgSO₄ and purified on silica gel with 8-17% EtOAc-PE which gave the title compound (2.418 g, 54%) as colorless oil.

¹H NMR (CDCl₃, 400 MHz) δ 0.95 (s, 3H), 1.51 (s, 3H), 2.15 (t, J=8.0 Hz, 2H), 2.36-2.62 (m, 2H), 2.92 (d, J=13.6 Hz, 1H), 3.10 (d, J=13.6 Hz, 1H), 3.67 (s, 3H), 7.15-7.30 (m, 5H); ¹³C NMR (CDCl₃, 100 MHz) δ 27.7, 28.8, 28.9, 33.1, 42.5, 52.1, 83.3, 110.4, 127.5, 128.6, 131.1, 135.1, 173.1, 174.1.

Example 58

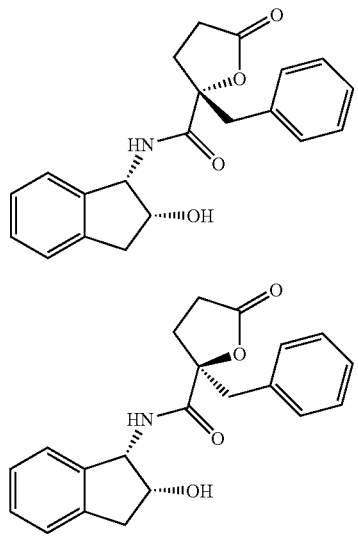

(R)-2-Benzyl-5-oxo-tetrahydro-furan-2-carboxylic acid ((1S,2R)-2-hydroxy-indan-1-yl)-amide (58a)

A solution of compound 57 (2.418 g, 8.272 mmol) in 6 mL TFA\H₂O (6:1) was stirred at 80° C. overnight. The solution was concentrated, dissolved in ethyl acetate and concentrated again for a couple times to get rid of TFA. The afforded residue was dried with vacuum until the raw product solidified. (1S,2R)-(−)-cis-1-Amino-2-indanol (1.234 g, 8.272 mmol), EDAC (1.744 g, 9.099 mmol), HOBt (1.229 g, 9.099 mmol) and 60 mL dry dichloromethane were added. The mixture was stirred for one hour at room temperature. The reaction was quenched with 30 mL water, filtered and extracted with 2×30 mL dichloromethane. The combined dichloromethane layers were concentrated and the residue was purified by column chromatography on silica gel eluted with MeOH—CH₂Cl₂ which gave the title compound (1.206 g, 41%) as a white solid. The other isomer (58b) eluted slower from the column. The absolute configuration of the title compound was confirmed by X-ray.

¹H NMR (CDCl₃, 400 MHz) δ 0.93 (d, J=4.4 Hz, 1H, OH), 2.32-2.48 (m, 2H), 2.50-2.64 (m, 1H), 2.76-2.86 (m, 2H), 3.04 (dd, J=16.4, 5.2 Hz, 1H), 3.13 (d, J=14.0 Hz, 1H), 3.36 (d, J=14.0 Hz, 1H), 4.18-4.26 (m, 1H), 5.23 (dd, J=8.8, 4.8 Hz, 1H), 6.68 (d, J=8.8 Hz, 1H), 7.02-7.08 (m, 1H), 7.14-7.24 (m, 3H), 7.28-7.38 (m, 5H); ¹³C NMR (CDCl₃, 100 MHz) δ 28.1, 31.0, 39.2, 44.2, 57.4, 73.0, 88.3, 123.7, 125.2, 127.1, 127.6, 128.3, 128.5, 130.5, 134.8, 139.4, 140.1, 171.4, 175.0.

Example 59

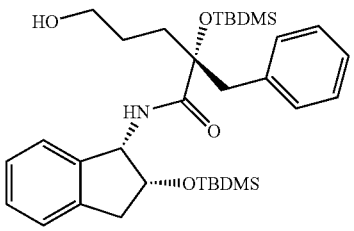

(R)-2-Benzyl-2-(tert-butyl-dimethyl-silanyloxy)-5-hydroxy-pentanoic acid [(1S,2R)-2-(tert-butyl-dimethyl-silanyloxy)-indan-1-yl]-amide (59)

To a solution of compound 58 (1.206 g, 3.432 mmol) and triethylamine (1.042 g, 10.30 mmol) in dichloromethane was added TBDMS-OTf (1.3606 g, 5.148 mmol) at 0° C. and the reaction mixture was stirred at room temperature for one hour. The solution was concentrated, extracted with diethyl ether\water. The ether layer was dried with MgSO₄, and filtered. LiBH₄ (223.8 mg, 10.30 mmol) was added to the ether solution at room temperature. After stirring for one hour, the reaction mixture was filtered and the resulting solution was concentrated which gave a crude intermediate. Pyridine (15 mL) and 0.845 mL PvCl (0.828 g, 6.864 mmol) were added to the afforded crude intermediate and the solution was stirred overnight. The reaction was quenched with saturated NH₄Cl aqueous solution, extracted with ether, dried with MgSO₄, concentrated, purified on silica gel eluted with EtOAc-PE. All fractions with MS 554 (M⁺+1) fragment were collected and concentrated which gave 1.243 g intermediate. The intermediate (1.243 g, 2.245 mmol), and 937.4 μL TEA (0.6815 g, 6.734 mmol) were dissolved in 15 mL DCM, and TBDMS-OTf (0.8899 g, 3.367 mmol) was added at 0° C. The solution was stirred for one hour at room temperature and then concentrated and extracted with diethyl ether\water. The ether layer was dried with MgSO₄, filtered and LiBH₄ (146.3 mg, 6.734 mmol) was added to the ether solution at room temperature. After another 1 h the mixture was filtered, concentrated and purified with 20%-50% EtOAc-PE which gave the title compound (783.2 mg, 39%) as colorless oil.

¹H NMR (CDCl₃, 400 MHz) δ 0.00 (s 3H), 0.01 (s, 3H), 0.05 (s, 3H), 0.08 (s, 3H), 0.75 (s, 9H), 0.81 (s, 9H), 1.04-1.28 (m, 1H), 1.48-1.64 (m, 2H), 1.75 (Br s, 1H), 1.92-2.06 (m, 1H), 2.83 (dd, J=15.6, 6.0 Hz, 1H), 2.91 (d, J=14.0 Hz, 1H), 2.99 (dd, J=15.6, 6.0 Hz, 1H), 3.12 (d, J=14.0 Hz, 1H), 3.26-3.42 (m, 2H), 4.54-4.62 (m, 1H), 5.13 (dd, J=8.0, 6.0 Hz, 1H), 7.05-7.20 (m, 8H), 7.30-7.40 (m, 2H); ¹³C NMR (CDCl₃, 100 MHz) δ 4.7, −4.3, −2.0, −1.5, 18.5, 18.7, 26.2, 26.4, 27.1, 35.0, 39.9, 47.5, 56.6, 62.3, 74.1, 82.6, 124.9, 125.7, 126.7, 126.9, 128.0, 128.2, 130.4, 136.5, 139.6, 141.8, 174.4.

Example 60

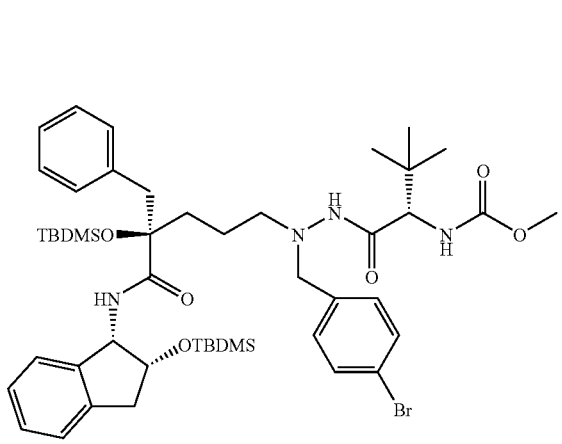

[(S)-1-(N'-(4-Bromo-benzyl)-N'-{(R)-4-(tert-butyl-dimethyl-silanyloxy)-4-[(1S,2R)-2-(tert-butyl-dimethyl-silanyloxy)-indan-1-ylcarbamoyl]-5-phenyl-pentyl}-hydrazinocarbonyl)-2,2-dimethyl-propyl]-carbamic acid methyl ester (60)

To a mixture of compound 59 (412.9 mg, 0.7070 mmol) and Dess-Martin periodinane (314.9 mg, 0.7424 mmol) was added 15 mL dry dichloromethane. The mixture was stirred at room temperature for 1 h, then concentrated, dissolved in 15 mL ether and washed with 15 mL water. The water phase was extracted with ether 2×15 mL. The ether layer was dried with MgSO$_4$, filtered and concentrated. The residue was dissolved in THF (20 ml) and {(S)-1-[N-(4-Bromo-benzyl)-hydrazinocarbonyl]-2,2-dimethyl-propyl}-carbamic acid methyl ester (263.2 mg, 0.7070 mmol) was added. To the solution was then added acetic acid (85.0 mg, 1.414 mmol) and the solution was stirred at room temperature. After 15 min, Na(OAc)$_3$BH (599.3 mg, 2.828 mmol) was added and the stirring was continued for another 2 h at room temperature. The reaction was quenched with saturated NH$_4$Cl aqueous solution, extracted with dichloromethane 3×20 mL, dried with MgSO$_4$, concentrated and purified on silica gel eluted with 20-40% EtOAc-PE which gave the title compound (300.0 mg, 45%) as white solid. 165 mg Of compound 59 was recovered.

$^1$H NMR (CDCl$_3$, 400 MHz) δ 0.05 (s 3H), 0.06 (s, 3H), 0.10 (s, 3H), 0.11 (s, 3H), 0.806 (s, 9H), 0.812 (s, 9H), 0.90 (s, 9H), 1.25-1.40 (m, 1H), 1.45-1.65 (m, 2H), 1.95-2.12 (m, 1H), 2.55-2.70 (m, 1H), 2.80-3.00 (m, 3H), 3.07 (dd, J=15.6, 6.0 Hz, 1H), 3.12 (d, J=13.6 Hz, 1H), 3.50-3.65 (m, 4H), 3.75-3.90 (m, 2H), 4.60-4.70 (m, 1H), 5.15-5.25 (m, 1H), 5.33 (d, J=9.2 Hz, 1H), 6.77 (s, 1H), 7.06-7.28 (m, 10H), 7.34-7.46 (m, 4H); $^{13}$C NMR (CDCl$_3$, 100 MHz) δ −4.7, −4.3, −1.9, −1.6, 18.5, 18.6, 21.8, 26.1, 26.3, 26.4, 34.4, 36.9, 39.9, 46.7, 52.4, 55.7, 56.5, 59.4, 61.2, 74.2, 82.7, 121.2, 124.9, 125.9, 126.6, 126.8, 128.0, 128.2, 130.4, 130.9, 131.3, 136.5, 136.6, 139.7, 141.9, 156.8, 169.7, 174.2.

Example 61

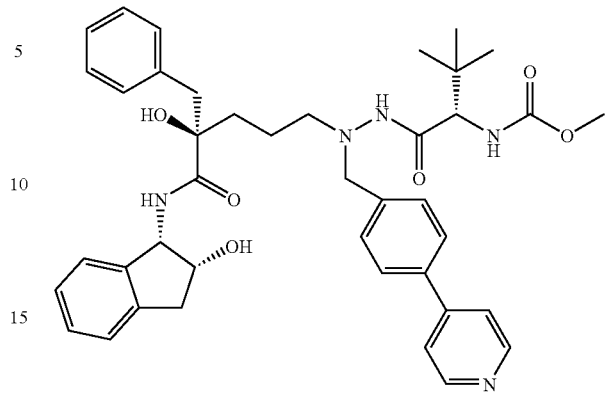

{(S)-1-[N'-[(R)-4-Hydroxy-4-((1S,2R)-2-hydroxy-indan-1-yl]carbamoyl)-5-phenyl-pentyl]-N'-(4-pyridin-4-yl-benzyl)-hydrazinocarbonyl]-2,2-dimethyl-propyl}-carbamic acid methyl ester (61)

Compound 60 (100.0 mg, 0.1066 mmol), 4-pyridinyl-bronic acid (39.2 mg, 0.3198 mmol), palladacycle (5.0 mg, 0.00533 mmol), HP(t-Bu)$_3$BF$_4$ (3.1 mg, 0.01066 mmol), K$_2$CO$_3$ (44.2 mg, 0.3198 mmol), DME (1.0 mL), H$_2$O (0.3 mL) were added to a 2-5 mL vial. The mixture was irradiated under microwaves at 120° C. for 20 min. The mixture was then extracted with ethyl acetate. The organic layer was dried with MgSO$_4$ and concentrated. To the afforded residue was added TBAF (1.06 mL) in THF (1.066 mmol) and the solution was stirred at room temperature overnight. Water (10 mL) was added to the solution which was then extracted with dichloromethane, and the organic phase was dried with MgSO$_4$ and concentrated. The residue was purified on silica gel with 1%-5% MeOH—CH$_2$Cl$_2$ which gave the title compound (52.9 mg, 70%) as a white solid.

$^1$H NMR (CD$_3$OD, 400 MHz) δ 0.75 (s, 9H), 1.56-1.70 (m, 1H), 1.70-1.86 (m, 2H), 2.03-2.16 (m, 1H), 2.74-2.94 (m, 4H), 3.01-3.14 (m, 2H), 3.46 (s, 3H), 3.70 (s, 1H), 3.88-4.00 (m, 2H), 4.16-4.22 (m, 1H), 5.09 (d, J=4.8 Hz, 1H), 7.10-7.30 (m, 9H), 7.50-7.70 (m, 6H), 8.50-8.60 (m, 2H); $^{13}$C NMR (CDCl$_3$, 100 MHz) δ 21.4, 25.7, 33.7, 36.6, 39.7, 45.8, 51.5, 57.1, 57.6, 61.2, 61.8, 72.8, 78.4, 105.0, 121.8, 124.2, 125.0, 126.3, 126.65, 126.68, 127.62, 127.67, 130.3, 130.5, 136.6, 137.0, 139.0, 140.4, 141.3, 149.4, 157.7, 170.7, 176.1.

Exaple 62

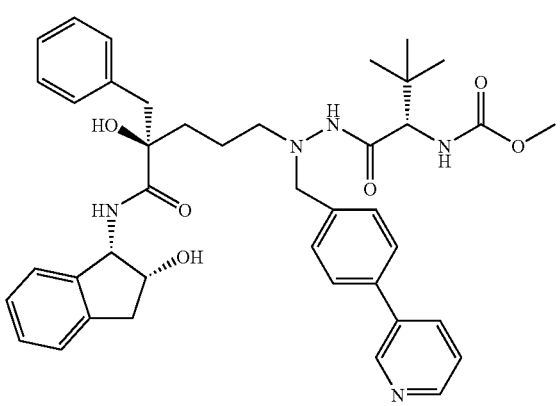

{(S)-1-[N'-[(R)-4-Hydroxy-4-((1S,2R)-2-hydroxy-indan-1-ylcarbamoyl)-5-phenyl-pentyl]-N'-(4-pyridin-3-yl-benzyl)-hydrazinocarbonyl]-2,2-dimethyl-propyl}-carbamic acid methyl ester (62) (AHA-625)

Compound 60 (100.0 mg, 0.1066 mmol), 3-pyridinyl-bronic acid (39.2 mg, 0.3198 mmol), palladacycle (5.0 mg, 0.00533 mmol), HP(t-Bu)$_3$BF$_4$ (3.1 mg, 0.01066 mmol), K$_2$CO$_3$ (44.2 mg, 0.3198 mmol), 1.0 mL DME, 0.3 mL H$_2$O were added to a 2-5 mL vial. The mixture was irradiated under microwaves at 120° C. for 20 min. The mixture was then extracted with ethyl acetate. The organic layer was dried with MgSO$_4$ and concentrated.

To the afforded residue was added TBAF (1.06 mL) in THF (1.066 mmol) and the solution was stirred at room temperature overnight. Water (10 mL) was added to the solution which was then extracted with dichloromethane, and the organic phase was dried with MgSO$_4$ and concentrated. The residue was purified on silica gel with 1%-5% MeOH—CH$_2$Cl$_2$ which gave the title compound (60.5 mg, 80%) as a white solid.

$^1$H NMR (CD$_3$OD, 400 MHz) δ 0.76 (s, 9H), 1.56-1.71 (m, 1H), 1.71-1.86 (m, 2H), 2.04-2.16 (m, 1H), 2.74-2.95 (m, 4H), 3.00-3.14 (m, 2H), 3.46 (s, 3H), 3.71 (s, 1H), 3.88-3.98 (m, 2H), 4.16-4.22 (m, 1H), 5.10 (d, J=4.8 Hz, 1H), 7.10-7.30 (m, 9H), 7.46-7.56 (m, 5H), 7.98-8.06 (m, 1H), 8.49 (dd, J=4.8, 0.8 Hz, 1H), 8.74 (d, J=1.2 Hz, 1H); $^{13}$C NMR (CDCl$_3$, 100 MHz) δ 22.6, 26.9, 34.9, 37.8, 40.9, 47.0, 52.6, 58.3, 58.7, 62.4, 63.0, 73.9, 79.5, 125.3, 125.5, 126.2, 127.5, 127.9, 128.8, 128.85, 131.5, 131.6, 136.4, 137.6, 138.2, 138.4, 138.8, 141.6, 142.5, 148.3, 148.6, 158.9, 171.8, 177.3.

Biological Examples

Extensive guidance on the assay of test compounds at the enzyme level and in cell culture, including the isolation and/or selection of mutant HIV strains and mutant RT are found in DAIDS Virology Manual for HIV Laboratories complied by Division of AIDS, NIAID USA 1997. Resistance studies, including rational for various drug escape mutants is described in the HIV Resistance Collaborative Group Data Analysis Plan for Resistance Studies, revised 31 Aug. 1999 and subsequently.

Cellular Assay

Compounds of the invention are assayed for HIV activity, for example using multiple determinations with XTT in MT-4 cells (Weislow et al, J Nat Cancer Inst 1989, vol 81 no 8, 577 et seq), preferably including determinations in the presence of 40-50% human serum to indicate the contribution of protein binding. In short the XTT assay uses human T cell line MT4 cells grown in RPMI 1640 medium supplemented with 10% fetal calf serum (or 40-50% human serum as appropriate), penicillin and streptomycin seeded into 96 well microplates (2·10$^4$ cells/well) infected with 10-20 TCID$_{50}$ per well of HIV-1$_{IIIB}$ (wild type) or mutant virus, such as those bearing RT Ile 100, Cys 181 or Asn 103 mutations. Serially diluted test compounds are added to respective wells and the culture incubated at 37° C. in a CO$_2$ enriched atmosphere and the viability of cells is determined at day five or six with XTT vital dye. Results are typically presented as ED$_{50}$ μM.

Expression of HIV-1 protease suitable for enzyme determination is also described in Danielsson et al. Adv. Exp. Med. Biol., 1998, 436, 99-103. Fluorometric assays for Ki determinations are also described in Antimicrob. Agents Chemother., 1997, 41, 2383-2388. This journal also describes a cellular assay for ED50 using MT4 cells and a colorimetric XTT assay.

Time to Resistance

2×10$^4$ MT4 cells per well in a microtitre plate are infected with 5-10 TCID$_{50}$ of HIV-1$_{IIIB}$. The compounds being tested are added at concentrations around ED$_{50}$ using 8 duplicates per concentration. After 6 days of incubation the RT activity in 10 μL supernatant is measured.

The following procedure is followed at subsequent passages of the cultures once per week. Virus produced at the concentration of test compound showing >50% of the RT activity of untreated infected cells (SIC, Starting Inhibitory Concentration) are passaged to fresh MT4 cells. 15 μL supernatant from each of the eight duplicates are transferred to cells without the test compound (control) and to cells with test compound at the same concentration, and additionally two respectively fivefold higher concentrations. (See Table 2 below)

When viral growth is permitted at the highest non-toxic concentration (5-40 μM), 2-4 parallel wells are collected and expanded to give material for sequence analysis and crosswise resistance.

TABLE 2

Viral growth permitted
Virus production inhibited

| | | | | 125 × SIC |
|---|---|---|---|---|
| | | | 125 × SIC | 25 × SIC → |
| | | | 25 × SIC | 5 ×SIC |
| | | 25 × SIC | 5 × SIC → | No compound |
| | 25 × SIC | 5 × SIC → | No compound | |
| | 5 × SIC | SIC | | |
| | SIC → | No compound | | |
| SIC → | No compound | | | |
| Pass 1 | Pass 2 | Pass 3 | Pass 4 | Pass 5 |

P450 Metabolism

The metabolism of compounds of the invention through the main isoforms of the human cytochrome system P450 are conveniently determined in baculovirus infected insect cells transfected with human cytochrome P450 cDNA (supersomes) Gentest Corp. Woburn USA.

The test compounds at concentrations 0.5, 5 and 50 µM are incubated in duplicate in the presence of supersomes overexpressing various cytochrome P450 isoforms, including CYP1A2+P450 reductase, CYP2A6+P450 reductase, CYP2C9-Arg 144+P450 reductase, CYP2C19+P450 reductase, CYP2D6-Val 374+P450 reductase and CYP3A4+P 450 reductase. Incubates contain a fixed concentration of cytochrome P450 (eg 50 pmoles) and are conducted over 1 hour. The involvement of a given isoform in the metabolism of the test compound is determined by UV HPLC chromatographically measuring the disappearance of parent compound.

For example, the following table shows the $K_1$ and $ED_{50}$ figures for a representative selection of compounds according to the invention. Category A indicates a Ki of <10 nM inhibition, category B indicates 11-50 nM inhibition and category C indicates 50-100 nM inhibition, category D indicates an $ED_{50}$<2 µM, category E indicates 2-10 µM and category E indicates >10 µM:

TABLE 1

Enzyme Inhibition and Antiviral Activity in Cell Culture.[a]

| Compound | Structure | $K_i$ (nM) | $ED_{50}$ (µM) |
|---|---|---|---|
| 11 | 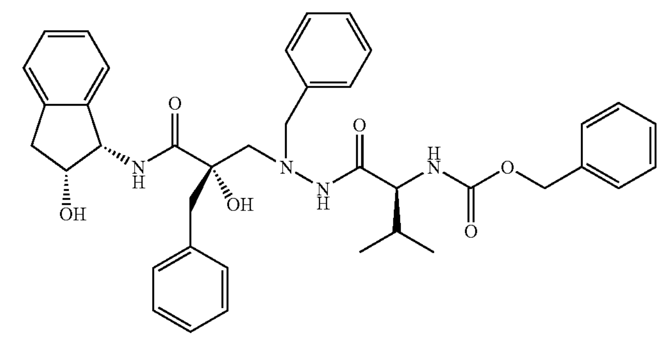 | B | F |
| 13 | 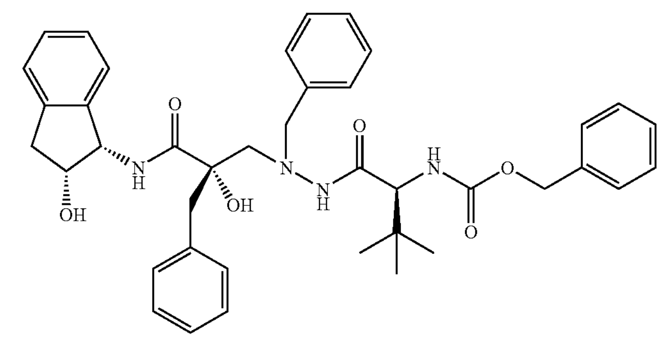 | B | F |
| 14 | 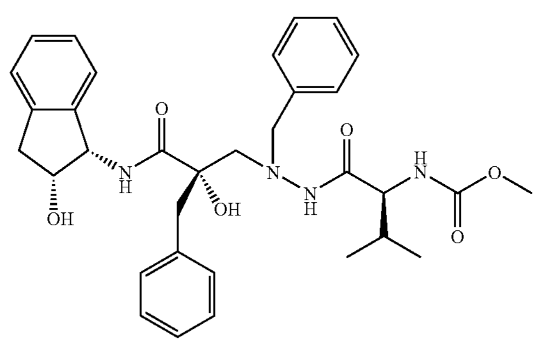 | A | E |

TABLE 1-continued

Enzyme Inhibition and Antiviral Activity in Cell Culture.[a]

| Compound | Structure | $K_i$ (nM) | $ED_{50}$ (μM) |
|---|---|---|---|
| 15 | 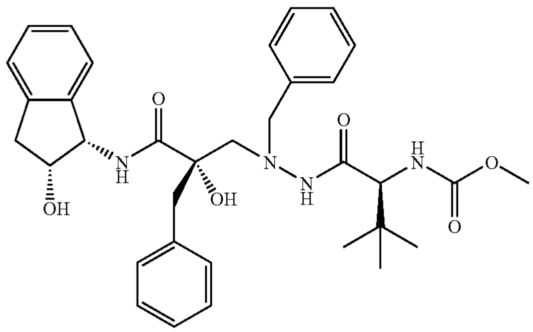 | A | E |
| 17 | 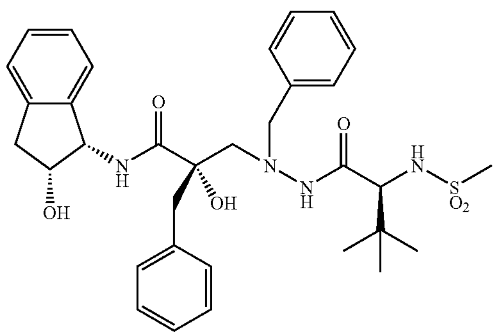 | C | F |
| 18 | 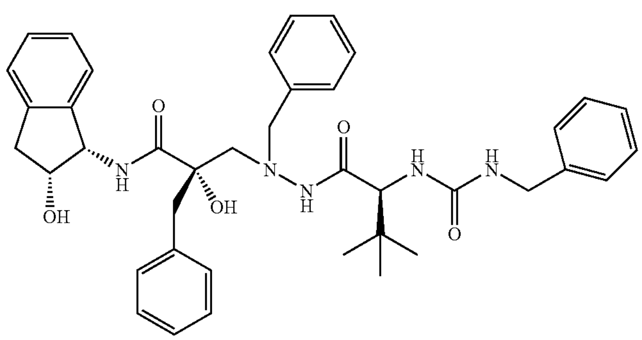 | B | F |
| 19 | 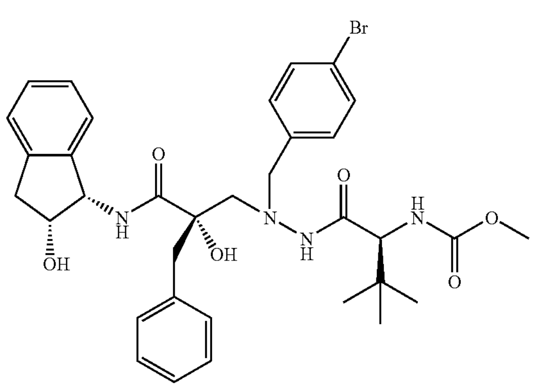 | A | D |

TABLE 1-continued

Enzyme Inhibition and Antiviral Activity in Cell Culture.[a]

| Compound | Structure | $K_i$ (nM) | $ED_{50}$ (µM) |
|---|---|---|---|
| 20 | 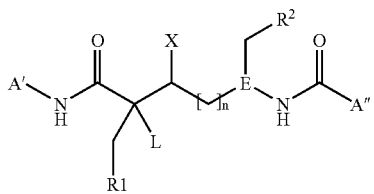 | B | F |

The invention claimed is:

1. A compound of the formula I:

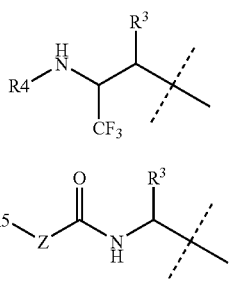

(I)

wherein $R^1$ is —$R^{1'}$, +$OR^{1'}$, —$SR^{1'}$, $R^{1'}$ is $C_1$-$C_6$Alk, $C_0$-$C_3$ alkanediylcarbocyclyl or $C_0$-$C_3$ alkanediylheterocyclyl, any of which is optionally substituted with up to 3 substituents independently selected from $R^{10}$;

$R^2$ is $C_1$-$C_6$Alk, $C_0$-$C_3$ alkanediylcarbocyclyl, $C_0$-$C_3$ alkanediylheterocyclyl, any of which is optionally substituted with up to 3 substituents independently selected from $R^{10}$;

X is H, F, OH, $C_1$-$C_3$Alk or $C_0$-$C_3$ alkanediyl-O—$C_1$-$C_3$ alkyl;

L is OH, F, $NH_2$, —$NHC_1$-$C_3$Alk; —$N(C_1$-$C_3$Alk$)_2$;

n is 0, 1 or 2;

E is N, CH;

A' is a bicyclic ring system comprising a first 5 or 6 membered saturated ring optionally containing an oxygen hetero atom and optionally substituted with hydroxy and/or methyl, having fused thereto a second 5 or 6 membered unsaturated ring optionally containing one or two hetero atoms selected from S, O and N, and optionally substituted with mono- or di-fluoro; or A' is a group of formula (II), (II'), (III) or (IV):

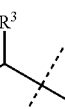

(II)

-continued

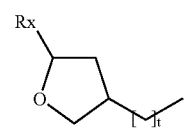

(II')

(III)

(IV)

wherein;

$R^3$ is H; or $R^3$ is $C_1$-$C_6$Alk, $C_0$-$C_3$ alkanediylcarbocyclyl, $C_0$-$C_3$ alkanediylheterocyclyl, any of which is optionally substituted with up to three substituents independently selected from $R^{11}$;

$R^4$ is $C_1$-$C_6$Alk, $C_0$-$C_3$ alkanediylcarbocyclyl, $C_0$-$C_3$ alkanediylheterocyclyl, any of which is optionally substituted with up to three substituents independently selected from $R^{10}$;

$R^5$ is $C_1$-$C_6$Alk, $C_0$-$C_3$alkanediylcarbocyclyl, $C_0$-$C_3$alkanediylheterocyclyl, any of which is optionally substituted with up to three substituents independently selected from $R^{10}$;

Z is bond, —NH—, —O—;

Rx is H, $C_1$-$C_3$alkyloxy, $C_1$-$C_3$ straight or branched alkyl optionally substituted with halo, hydroxy, $C_1$-$C_3$alkyloxy; or Rx, together with the adjacent carbon atom, defines a fused furanyl or pyranyl ring which is optionally substituted with halo or $C_1$-$C_3$Alk;

t is 0 or 1;

A" is a group of formula (V), (VI) (VII) or (VIII);

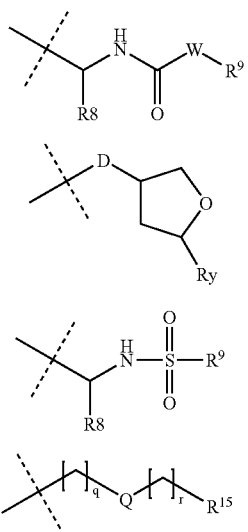

wherein;

$R^8$ is H; or $R^8$ is $C_1$-$C_6$Alk, $C_0$-$C_3$alkanediylcarbocyclyl, $C_0$-$C_3$alkanediylheterocyclyl, any which is optionally substituted with up to three substituents independently selected from $R^{11}$;

$R^9$ is $C_1$-$C_6$Alk, $C_0$-$C_3$alkanediylcarbocyclyl, $C_0$-$C_3$alkanediylheterocyclyl, any of which is optionally substituted with up to three substituents independently selected from $R^{10}$;

W is a bond, —$NR^{13}$— or —O—;

$R^{13}$ is H or $C_1$-$C_6$Alk, or $R^{13}$ and $R^9$ together with the N atom to which they are attached define a saturated, partially saturated or aromatic N-containing ring containing 5 or 6 ring atoms, which is optionally substituted with up to three substituents selected from $R^{10}$;

D is O or NH;

Ry is H or Ry, together with the adjacent C atom defines a fused furan or pyran ring;

Q is O, $CHR^8$ or a bond;

$R^{15}$ is carbocyclyl or heterocyclyl, any of which is optionally substituted with up to three substituents independently selected from $C_1$-$C_3$Alk, hydroxy, oxo, halo;

q and r are independently 0 or 1;

$R^{10}$ is halo, oxo, cyano, azido, nitro, $C_1$-$C_6$Alk, $C_0$-$C_3$alkanediylcarbocyclyl, $C_0$-$C_3$alkanediylheterocyclyl, Y—NRaRb, Y—O—Rb, Y—C(=O)Rb, Y—(C=O)NRaRb, Y—NRaC(=O)Rb, Y—NHSO$_p$Rb, Y—S(=O)$_p$Rb, Y—S(=O)$_p$N-RaRb, Y—C(=O)ORb or Y—NRaC(=O)ORb; wherein;

Y is a bond or $C_1$-$C_3$alkanediyl;

Ra is H or $C_1$-$C_3$Alk;

Rb is H or $C_1$-$C_6$Alk, $C_0$-$C_3$alkanediylcarbocyclyl or $C_0$-$C_3$alkanediylheterocyclyl;

p is 1 or 2;

$R^{11}$ is halo, oxo, cyano, azido, nitro, $C_1$-$C_3$Alk, Y—NRaRa', Y—O—Ra; wherein;

Ra' is H or $C_1$-$C_3$Alk; or Ra and Ra' and the nitrogen atom to which they are attached define pyrrolidine, morpholine, piperidine or piperazine which is optionally 4-substituted with methyl or acetyl;

$C_1$-$C_6$Alk is a straight or branched aliphatic carbon chain containing from 1 to 6 carbon atoms, optionally having at least one unsaturated bond;

$C_1$-$C_5$Alk is a straight or branched aliphatic carbon chain containing from 1 to 5 carbon atoms, optionally having at least one unsaturated bond;

$C_1$-$C_4$Alk is a straight or branched aliphatic carbon chain containing from 1 to 4 carbon atoms, optionally having at least one unsaturated bond;

$C_1$-$C_3$Alk is a straight or branched aliphatic carbon chain containing from 1 to 3 carbon atoms, optionally having at least one unsaturated bond;

or pharmaceutically acceptable salts thereof.

2. A compound according to claim 1 wherein $R^1$ is optionally substituted $C_0$-$C_3$alkanediylcarbocyclyl or $C_0$-$C_3$alkanediylheterocyclyl.

3. A compound according to claim 2, wherein $R^{1'}$ is optionally substituted carbocyclyl or heterocyclyl.

4. A compound according to claim 3, wherein the $R^{1'}$ carbocyclyl moiety is optionally substituted phenyl or the $R^{1'}$ heterocyclyl moiety is optionally substituted pyridyl, pyrazinyl, pyrimidinyl or pyridazinyl.

5. A compound according to claim 1, wherein at least one optional substituent to $R^{1'}$ is selected from halo, oxo, cyano, $C_1$-$C_6$Alk, $C_0$-$C_3$alkanediylcarbocyclyl, $C_0$-$C_3$alkanediylheterocyclyl, Y—NRaRb, and Y—O—Rb; where Y is a bond or $C_1$-$C_3$Alk, Ra is H or $C_1$-$C_3$Alk and Rb is H or $C_1$-$C_3$Alk.

6. A compound according to claim 5, wherein the optional substituent to $R^{1'}$ is selected from fluoro, $C_1$-$C_3$Alk, $C_0$-$C_1$alkanediylcarbocyclyl, or $C_0$-$C_1$alkanediylheterocyclyl.

7. A compound according to claim 4, wherein $R^{1'}$ is mono- or di-halo substituted phenyl.

8. A compound according to claim 7 wherein $R^{1'}$ is mono- or di-fluoro substituted phenyl.

9. A compound according to claim 4 wherein $R^{1'}$ is phenyl.

10. A compound according to claim 1, with the stereochemistry shown in the partial structure.

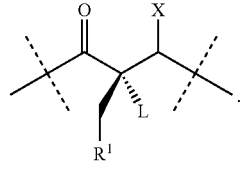

11. A compound according to claim 1 wherein $R^2$ is optionally substituted $C_0$-$C_3$alkanediylcarbocyclyl or $C_1$-$C_3$alkanediylheterocyclyl.

12. A compound according to claim 11, wherein $R^2$ is optionally substituted carbocyclyl or heterocyclyl.

13. A compound according to claim 12, wherein the $R^2$ carbocyclyl moiety is optionally substituted phenyl or the $R^2$ heterocyclyl moiety is optionally substituted pyridyl, pyrazinyl, pyrimidinyl or pyridazinyl.

14. A compound according to claim 1, wherein at least one optional substituent to $R^2$ is selected from halo, oxo, cyano, $C_1$-$C_6$Alk, $C_0$-$C_3$alkanediylcarbocyclyl, $C_0$-$C_3$alkanediylheterocyclyl, Y—NRaRb, and Y—O—Rb; where Y is a bond or $C_1$-$C_3$Alk, Ra is H or $C_1$-$C_3$Alk and Rb is H or $C_1$-$C_3$Alk.

15. A compound according to claim 14, wherein the optional substituent to $R^2$ is selected from fluoro, $C_1$-$C_3$Alk, $C_0$-$C_1$alkanediylcarbocyclyl, or $C_0$-$C_1$alkanediylheterocyclyl.

16. A compound according to claim 13, wherein R² is carbocyclyl or heterocyclyl substituted phenyl.

17. A compound according to claim 16, wherein R² is aryl or heteroaryl substituted phenyl.

18. A compound according to claim 17 wherein R² is pyridyl substituted phenyl.

19. A compound according to claim 1, wherein X is H or OH.

20. A compound according to claim 1, wherein n is 1.

21. A compound according to claim 1, wherein E is N.

22. A compound according to claim 1, wherein A' is a group of formula (II) or (IV).

23. A compound according to claim 22, wherein R³ is H, optionally substituted $C_1$-$C_6$Alk or optionally substituted $C_0$-$C_3$alkanediyiheterocyciyl.

24. A compound according to claim 23, wherein R³ is H or optionally substituted $C_1$-$C_6$Alk.

25. A compound according to claim 23, wherein R³ is $C_1$-$C_6$Alk optionally substituted with halo.

26. A compound according to claim 23, wherein the optional substituent to R³ is oxo, cyano or halo or Y—O—Ra, where Y is a bond or $C_1$-$C_3$Alk and Ra is H or $C_1$-$C_3$Alk.

27. A compound according to claim 1, wherein R⁴ is optionally substituted $C_1$-$C_6$Alk.

28. A compound according to claim 1, wherein the optional substituent to R⁴ is halo, oxo, cyano, azido, nitro, $C_1$-$C_6$Alk, $C_0$-$C_3$alkanediylcarbocyclyl, $C_0$-$C_3$alkanediylheterocyclyl, Y—NRaRb or Y—O—Rb wherein;

Y is a bond or $C_1$-$C_3$Alk;
Ra is H or $C_1$-$C_3$Alk;
Rb is H or $C_1$-$C_6$Alk, $0_1$-$C_3$alkanediylcarbocyclyl or $C_0$-$C_3$alkanediylheterocyclyl.

29. A compound according to claim 28 wherein the optional substituent is halo, oxo, $C_1$-$C_6$Alk, $C_0$-$C_3$alkanediylcarbocyclyl, $C_{10}$-$C_3$alkanediylheterocyclyl or Y—O—Rb.

30. A compound according to claim 29, wherein the optional substituent is halo or Y—O—Rb.

31. A compound according to claim 30, wherein R⁴ is methyl.

32. A compound according to claim 22, with the stereochemistry shown in the partial structure

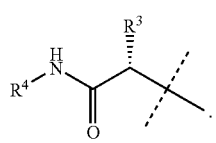

(II)

33. A compound according to claim 22, wherein Rx is hydroxymethyl, 1-hydroxyethyl, 1-hydroxypropyl, fluoromethyl, 1-fluoroethyl or 1-fluoropropyl.

34. A compound according to claim 22, wherein Rx is methoxymethyl, ethoxymethyl, 1-methoxyethyl, 1-ethoxyethyl, 1-methoxypropyl or 1-ethoxypropyl.

35. A compound according to claim 22, wherein A' is

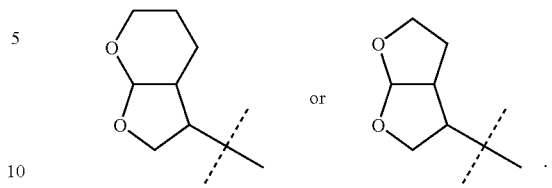

36. A compound according to claim 1, wherein A' is a bicyclic ring system comprising a first 5 or 6 membered saturated ring optionally containing an oxygen hetero atom, and optionally substituted with hydroxy or methyl, having fused thereto a second 5 or 6 membered unsaturated ring optionally containing one or two hetero atoms selected from S, O and N, and optionally mono- or di-fluoro substituted.

37. A compound according to claim 36, wherein the bond to the rest of the molecule extends from carbon 1 of said saturated ring.

38. A compound according to claim 37, wherein the optional hydroxy substituent is at carbon 2 of said saturated ring.

39. A compound according to claim 37, wherein the oxygen hetero atom is position 3 of a 5 membered saturated ring or position 4 of a 6 membered saturated ring.

40. A compound according to claim 36, wherein said second ring is 5-membered and comprises a sulphur hetero atom or an oxygen hetero atom.

41. A compound according to claim 36, wherein said second ring is optionally substituted phenyl.

42. A compound according to claim 41, wherein the substituent is mono- or di-fluoro.

43. A compound according to claim 36, wherein A' is:

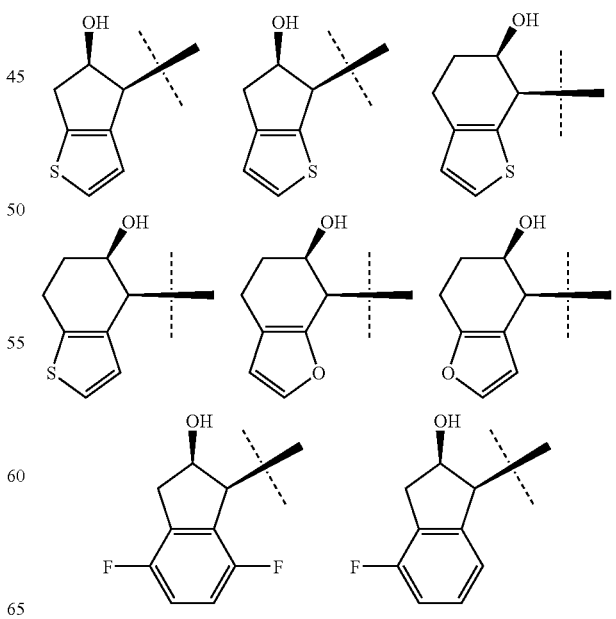

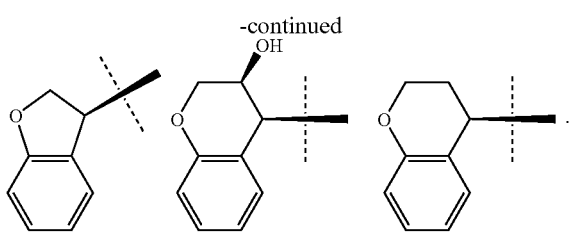

44. A compound according to claim 36, wherein A' is

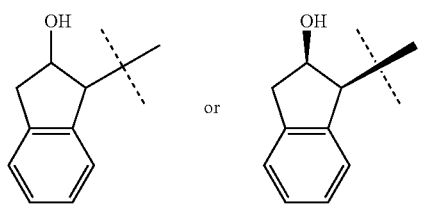

45. A compound according to claim 1, wherein A" is of the formula (V).

46. A compound according to claim 45, wherein $R^8$ is H, optionally substituted $C_1$-$C_6$Alk or optionally substituted $C_0$-$C_3$alkanediylcarbocyclyl.

47. A compound according to claim 46, wherein $R^8$ is H or optionally substituted $C_1$-$C_6$Alk.

48. A compound according to claim 45, wherein the optional substituent to $R^8$ is oxo, cyano, $C_1$-$C_3$Alk or halo or Y—O—Ra;
where Y is a bond or $C_1$-$C_3$Alk;
Ra is H or $C_1$-$C_3$Alk.

49. A compound according to claim 45, wherein $R^9$ is optionally substituted $C_1$-$C_6$Alk or $C_0$-$C_3$alkanediylcarbocyclyl.

50. A compound according to claim 49, wherein $R^9$ is optionally substituted methyl.

51. A compound according to claim 45, wherein the optional substituent to $R^9$ is halo, oxo, cyano, azido, nitro, $C_1$-$C_6$Alk, $C_0$-$C_3$alkanediylcarbocyclyl, $C_0$-$C_3$alkanediylheterocyclyl, Y—NRaRb or Y—O—Rb wherein;

Y is a bond or $C_1$-$C_3$Alk;
Ra is H or $C_1$-$C_3$Alk;
Rb is H or $C_1$-$C_6$Alk, $C_0$-$C_3$alkanediylcarbocyclyl or $C_0$-$C_3$alkanediylheterocyclyl.

52. A compound according to claim 51, wherein the optional substituent is halo, oxo, $C_1$-$C_6$Alk, $C_0$-$C_3$alkanediylcarbocyclyl, $C_0$-$C_3$alkanediylheterocyclyl or Y—O—Rb.

53. A compound according to claim 52, wherein $R^9$ is methyl.

54. A compound according to claim 45 wherein W is —O—.

55. A compound according to claim 45 with the stereochemistry shown in the partial structure:

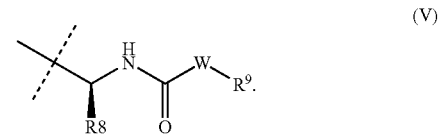

(V)

56. A pharmaceutical composition comprising a compound as defined in claim 1 and a pharmaceutically acceptable carrier or diluent therefore.

57. A pharmaceutical composition according to claim 56, further comprising 1 to 3 additional HIV antivirals.

58. A method of treatment for HIV infection comprising administering an effective amount of a compound as defined in claim 1 to an individual infected or threatened with HIV infection.

59. The compound according to claim 25 wherein $R^3$ is isopropyl or t-butyl.

60. The compound according to claim 26 wherein $R^3$ is Y—O—Ra.

61. The compound according to claim 27 wherein $R^4$ is methyl or optionally substituted methyl.

62. The compound according to claim 47 wherein $R^8$ is isopropyl or t-butyl.

63. The compound according to claim 48 wherein $R^8$ is Y—O—Ra or halo.

* * * * *